US010371609B2

(12) United States Patent
Kwon

(10) Patent No.: US 10,371,609 B2
(45) Date of Patent: Aug. 6, 2019

(54) DEVICES AND METHODS FOR OVERLAYING BLOOD OR CELLULAR SUSPENSIONS

(75) Inventor: Jae Go Kwon, Thousand Oaks, CA (US)

(73) Assignee: Jae Go Kwon, Thousand Oaks, CA (US)

( * ) Notice: Subject to any disclaimer, the term of this patent is extended or adjusted under 35 U.S.C. 154(b) by 1066 days.

(21) Appl. No.: 14/237,516

(22) PCT Filed: Aug. 9, 2012

(86) PCT No.: PCT/US2012/050192
§ 371 (c)(1),
(2), (4) Date: Aug. 15, 2014

(87) PCT Pub. No.: WO2013/023089
PCT Pub. Date: Feb. 14, 2013

(65) Prior Publication Data
US 2014/0356898 A1 Dec. 4, 2014

Related U.S. Application Data

(60) Provisional application No. 61/521,573, filed on Aug. 9, 2011.

(51) Int. Cl.
G01N 1/31 (2006.01)
B01L 3/00 (2006.01)
B01L 3/02 (2006.01)

(52) U.S. Cl.
CPC .............. *G01N 1/31* (2013.01); *B01L 3/5021* (2013.01); *B01L 3/0293* (2013.01);
(Continued)

(58) Field of Classification Search
CPC ....... B01L 2200/026; B01L 2200/0642; B01L 2300/046; B01L 2400/0457;
(Continued)

(56) References Cited

U.S. PATENT DOCUMENTS 4,469,151 A    9/1984  Wilson et al.
4,534,863 A *  8/1985  Bacon ................... B01D 29/01
                                                    210/232

(Continued)

FOREIGN PATENT DOCUMENTS

WO    WO 2010093840 A1 *  8/2010  .............. B01L 3/502

OTHER PUBLICATIONS

International Preliminary Report on Patentability; PCT Application No. PCT/US2012/050192; dated Feb. 11, 2014.

(Continued)

*Primary Examiner* — Dennis White
*Assistant Examiner* — Brian Kilpatrick
(74) *Attorney, Agent, or Firm* — Adler Pollock & Sheehan P.C.

(57) ABSTRACT

A device is described that overlays a first fluid, such as blood or a cellular suspension onto a base material, such as a density gradient. In some embodiments, the fluid layering device includes a cylindrical reservoir, a fluid barrier, a coupling extension, a plunger, and an exhaust vent. The fluid layering device can be coupled through its coupling extension to an open end of a container, such as a conical centrifuge tube, including the density gradient. Once attached, the plunger may be lowered to a position above the surface of the density gradient. A first fluid may flow from the reservoir into the conical tube across the plunger, so that a suitable overlay is formed without substantially disturbing a surface of the density gradient. The plunger may be buoyed upward by the first fluid during operation, providing a constant regulation of flow throughout overlaying, regardless of the care and skill of the user.

9 Claims, 53 Drawing Sheets

(52) U.S. Cl.
CPC . *B01L 2200/026* (2013.01); *B01L 2200/0642* (2013.01); *B01L 2300/046* (2013.01); *B01L 2400/0457* (2013.01); *B01L 2400/086* (2013.01)

(58) Field of Classification Search
CPC ............ B01L 2400/086; B01L 3/0293; B01L 3/5021; G01N 1/31
See application file for complete search history.

(56) References Cited

U.S. PATENT DOCUMENTS

| | | |
|---|---|---|
| 5,663,051 A | 9/1997 | Vlasselaer |
| 7,211,433 B1 | 5/2007 | Dahm et al. |
| 7,837,884 B2 | 11/2010 | Dorian et al. |
| 2011/0008908 A1* | 1/2011 | Biesbrouck ............ B01L 3/502 436/501 |

OTHER PUBLICATIONS

International Search Report and Written Opinion; PCT Application No. PCT/US2012/050192; dated Nov. 2, 2012.

* cited by examiner

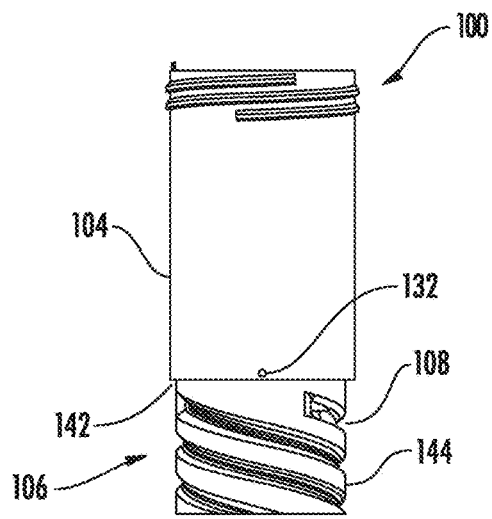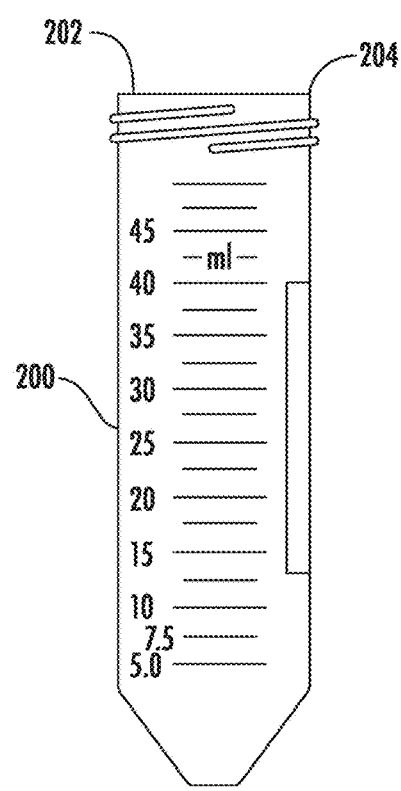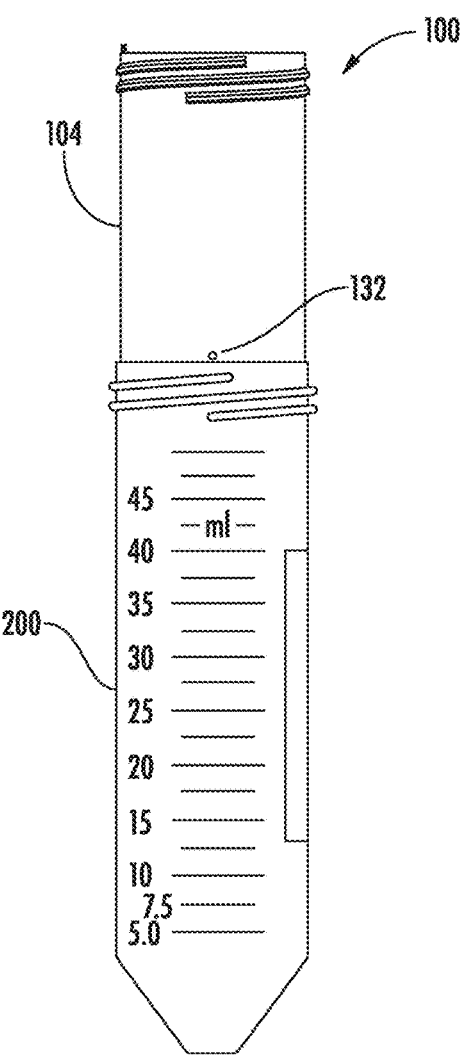
FIG. 4A                              FIG. 4B

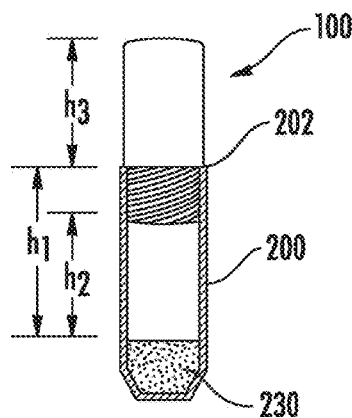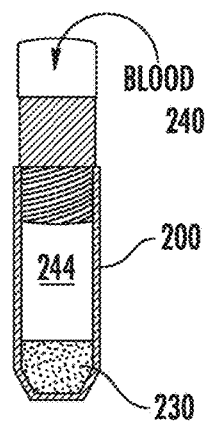
FIG. 6A    FIG. 6B
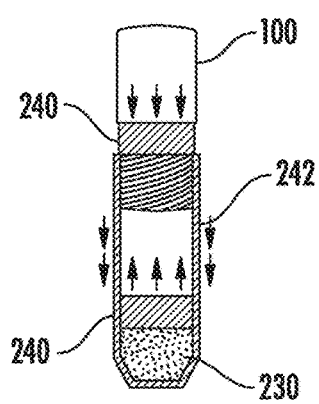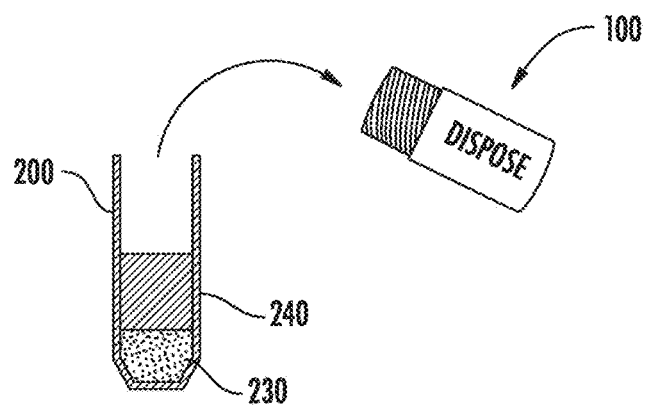
FIG. 6C    FIG. 6D

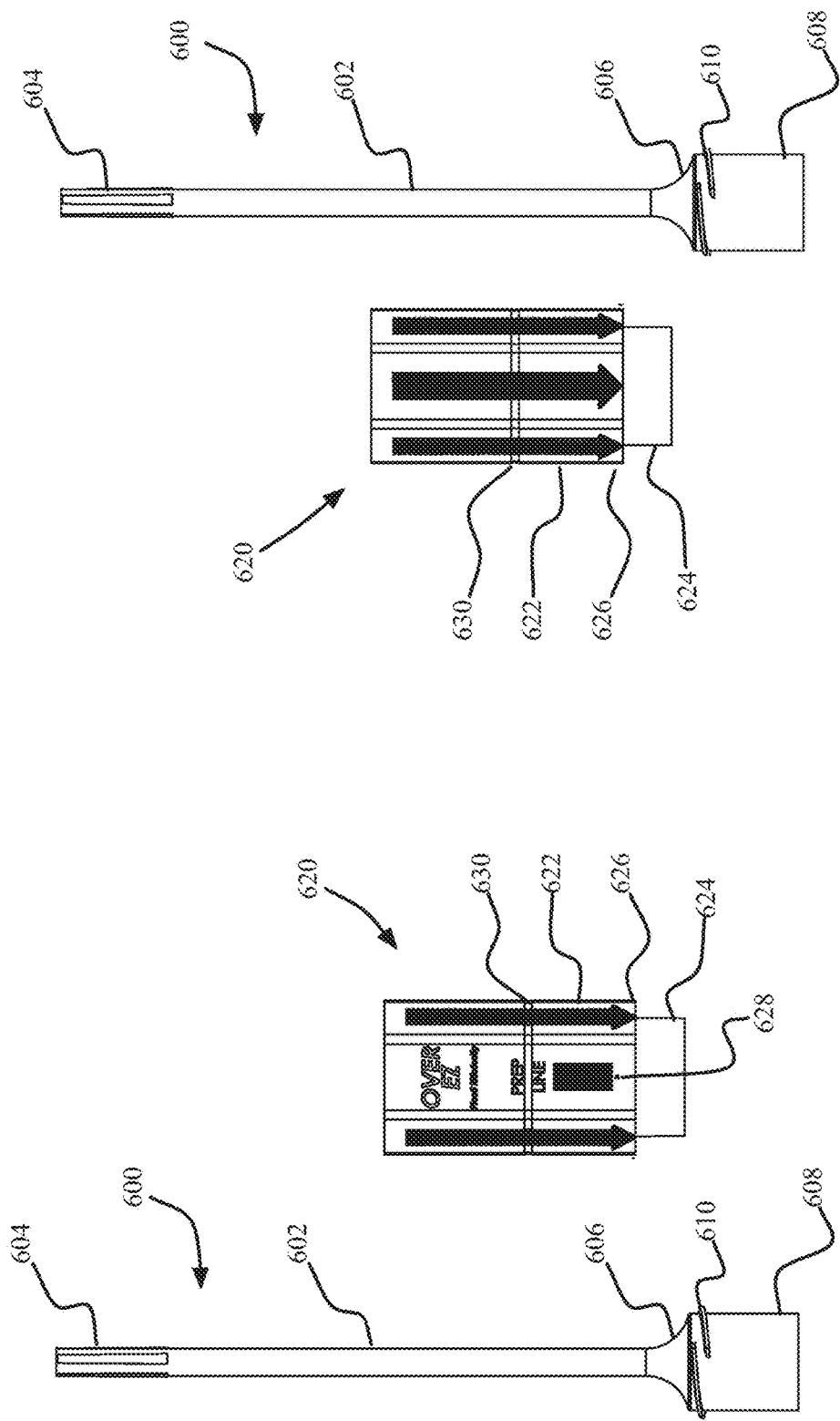

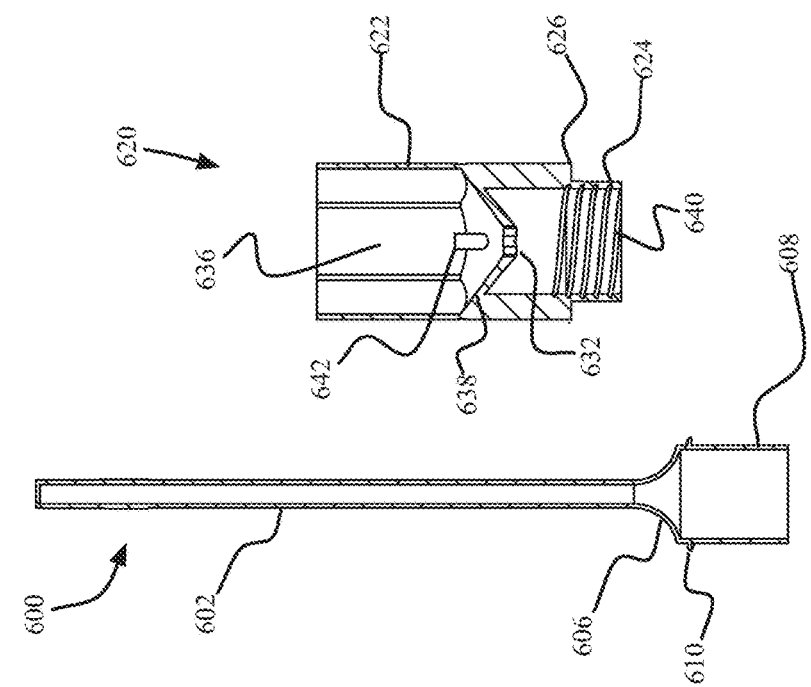
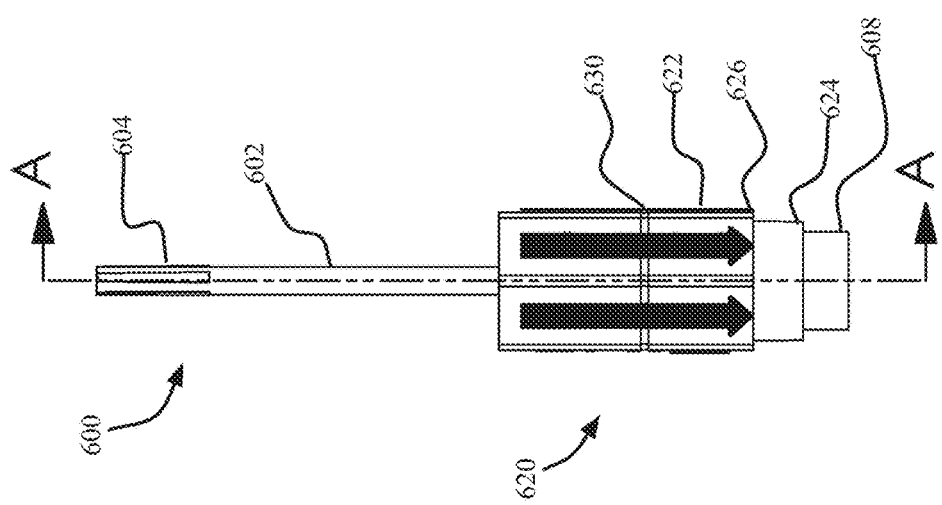
FIG. 10F
FIG. 10E

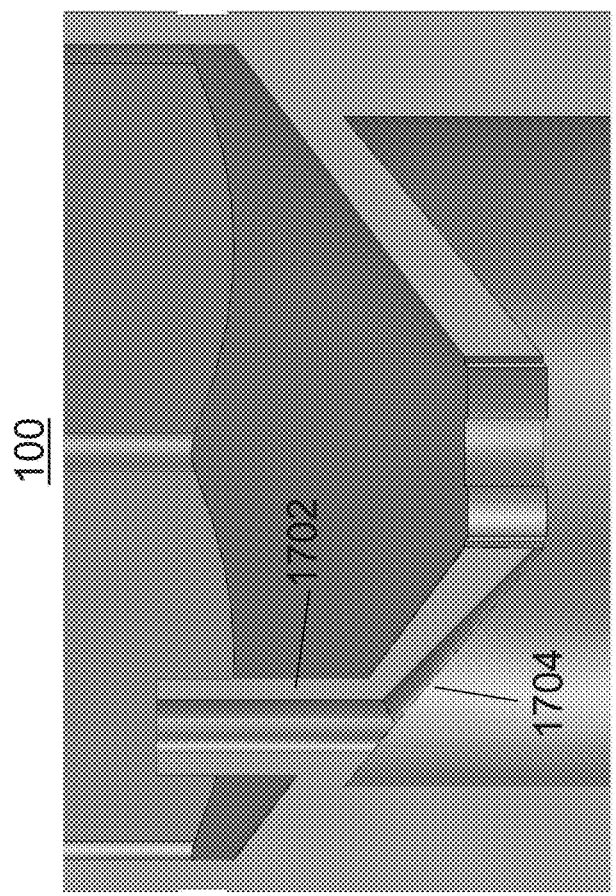
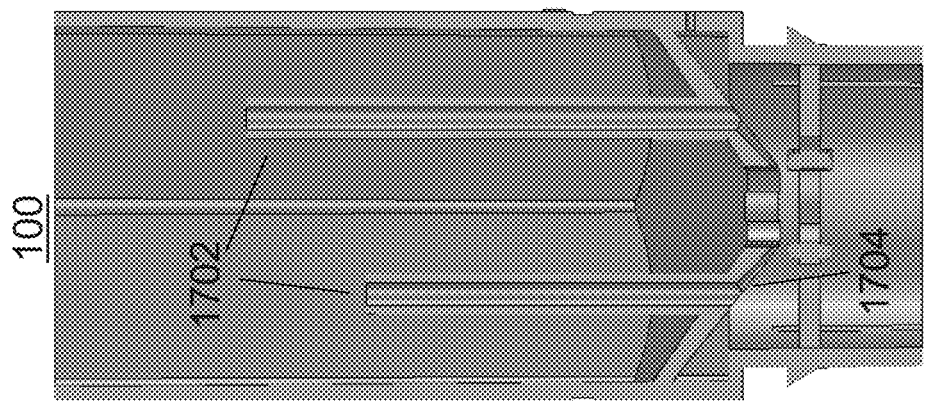
FIG. 17B
FIG. 17A

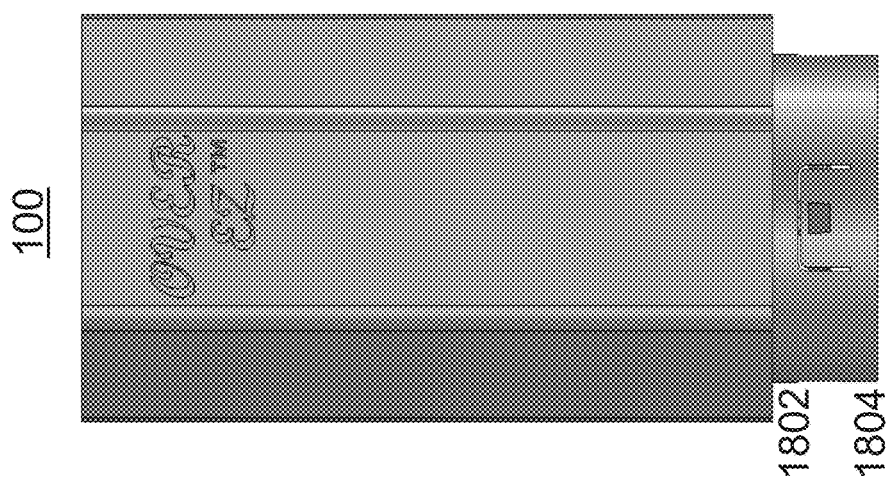

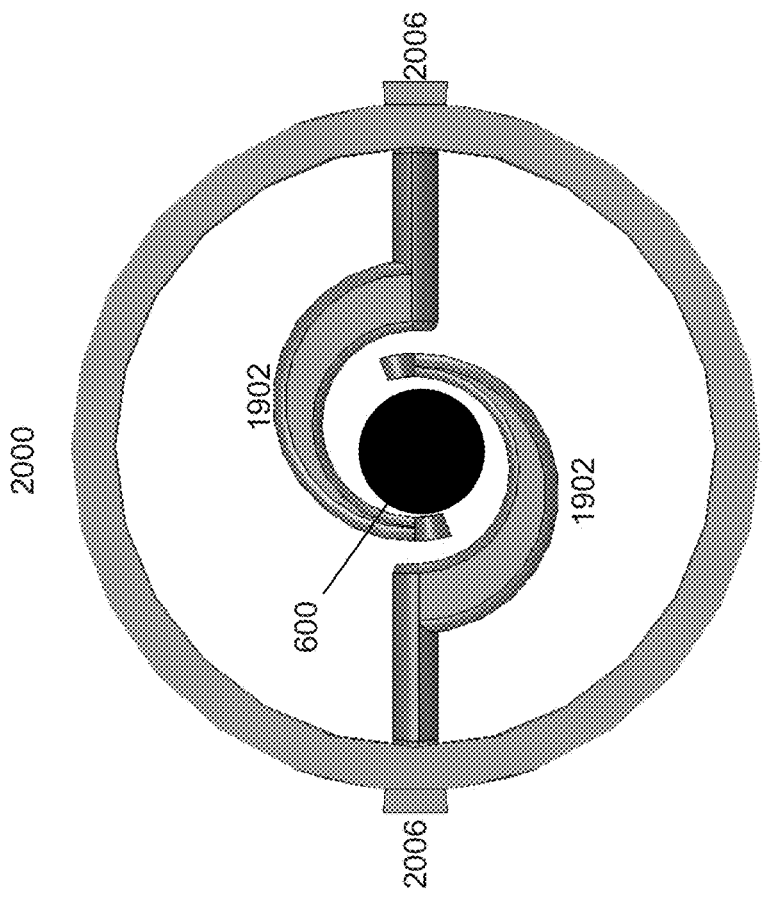
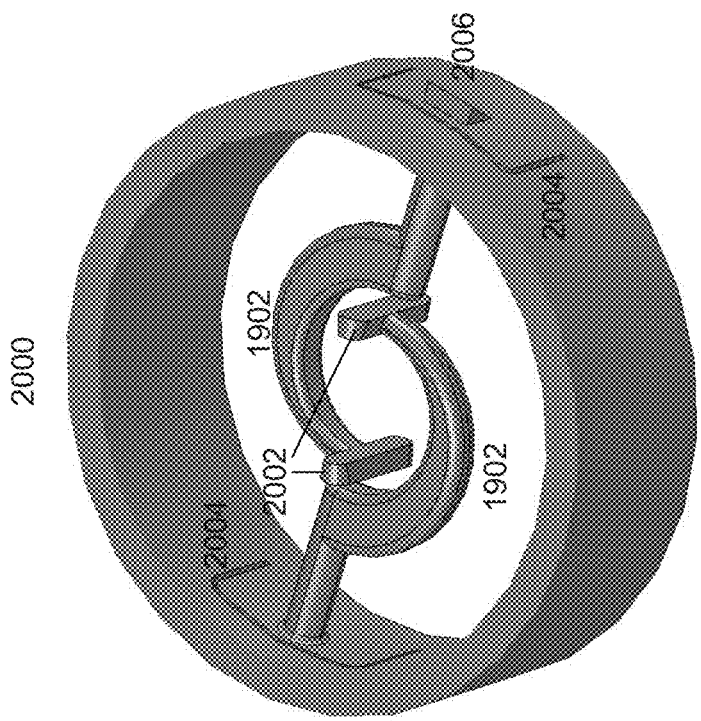
FIG. 20B
FIG. 20A

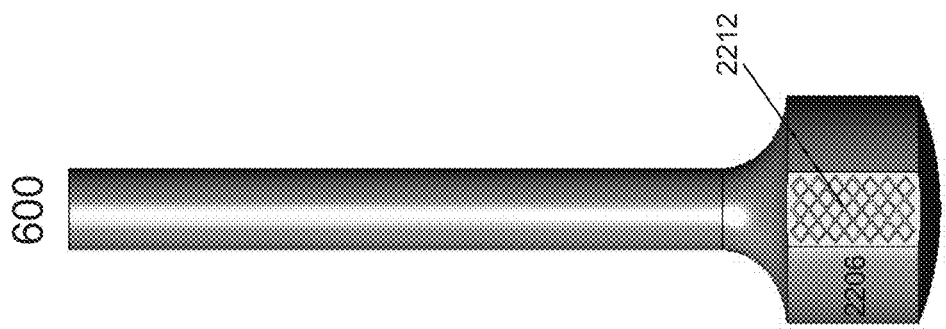
FIG. 22C
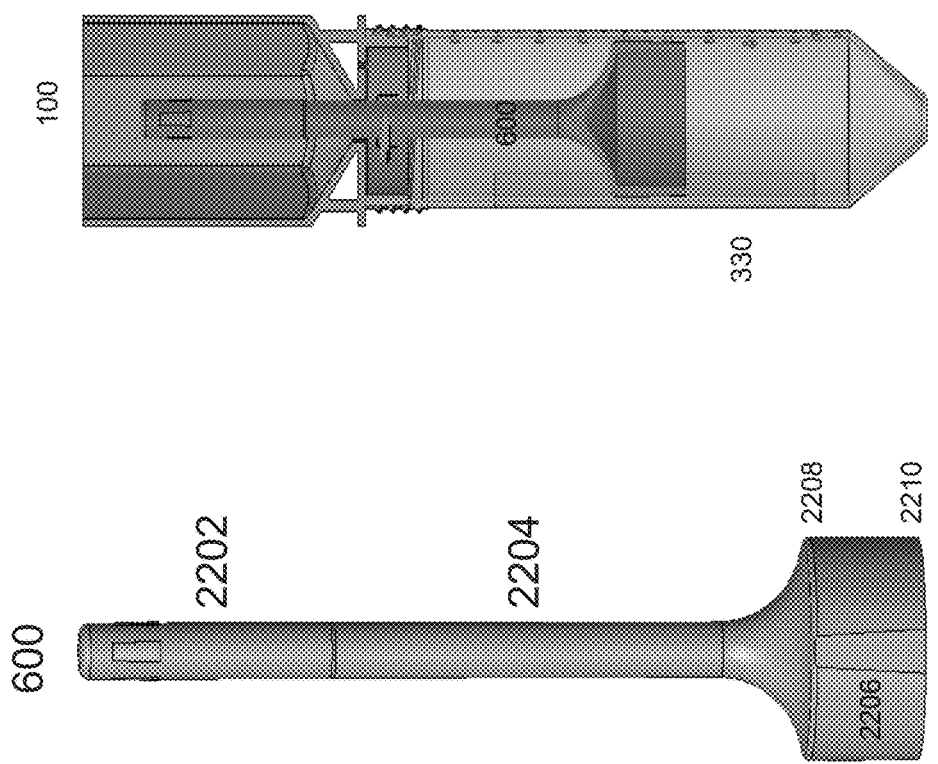
FIG. 22B
FIG. 22A

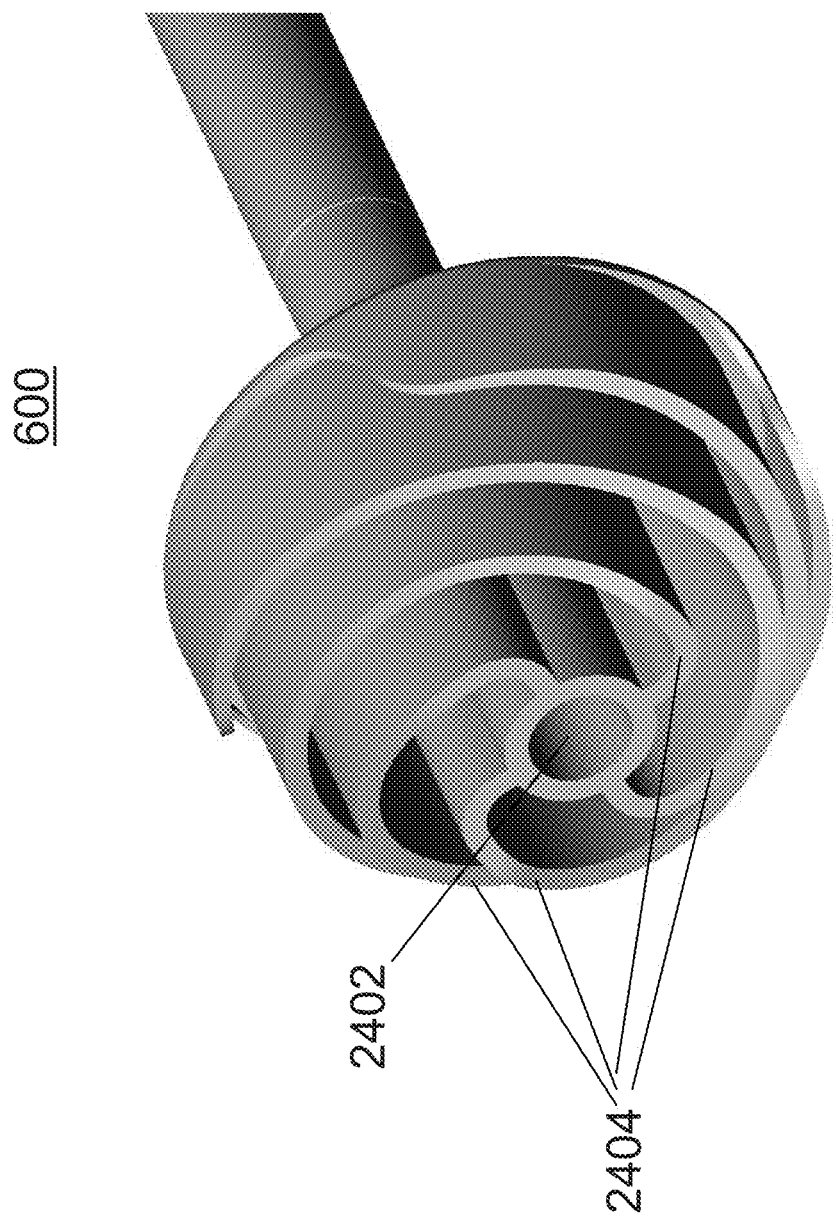

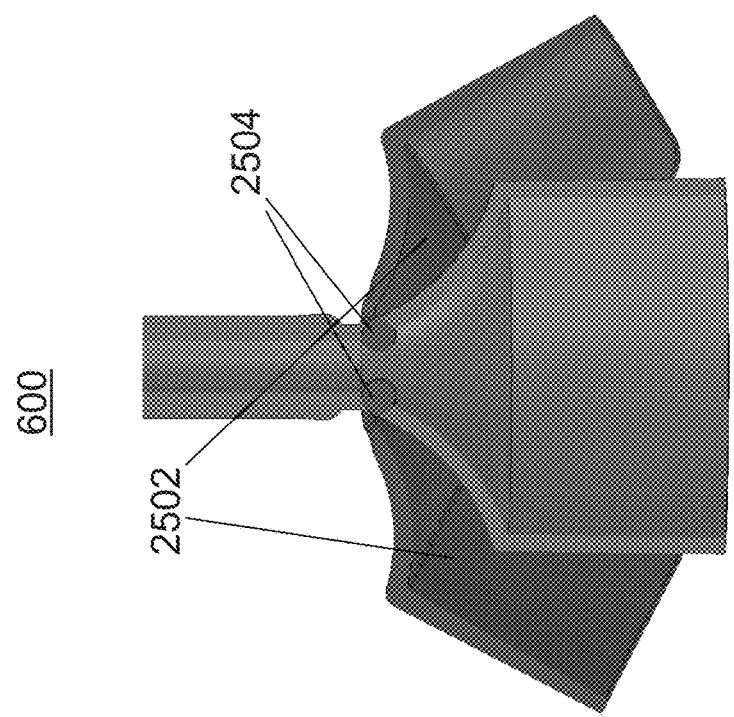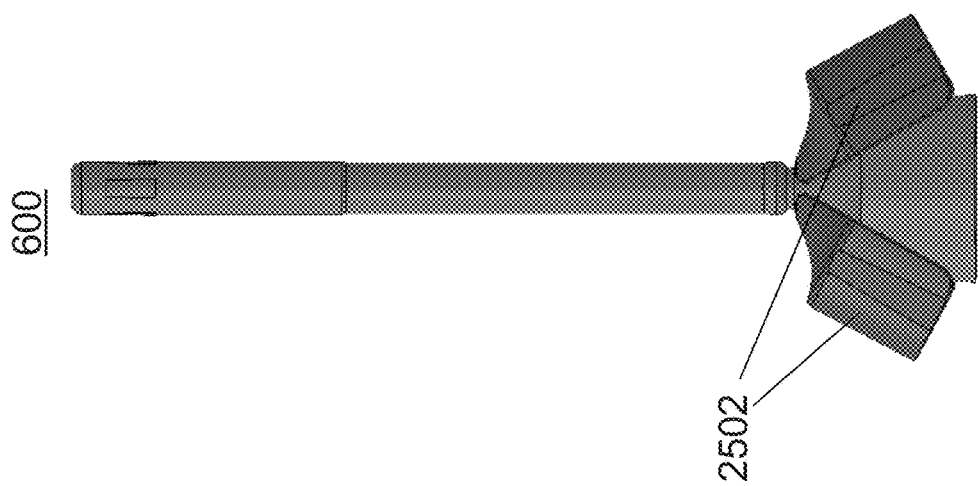

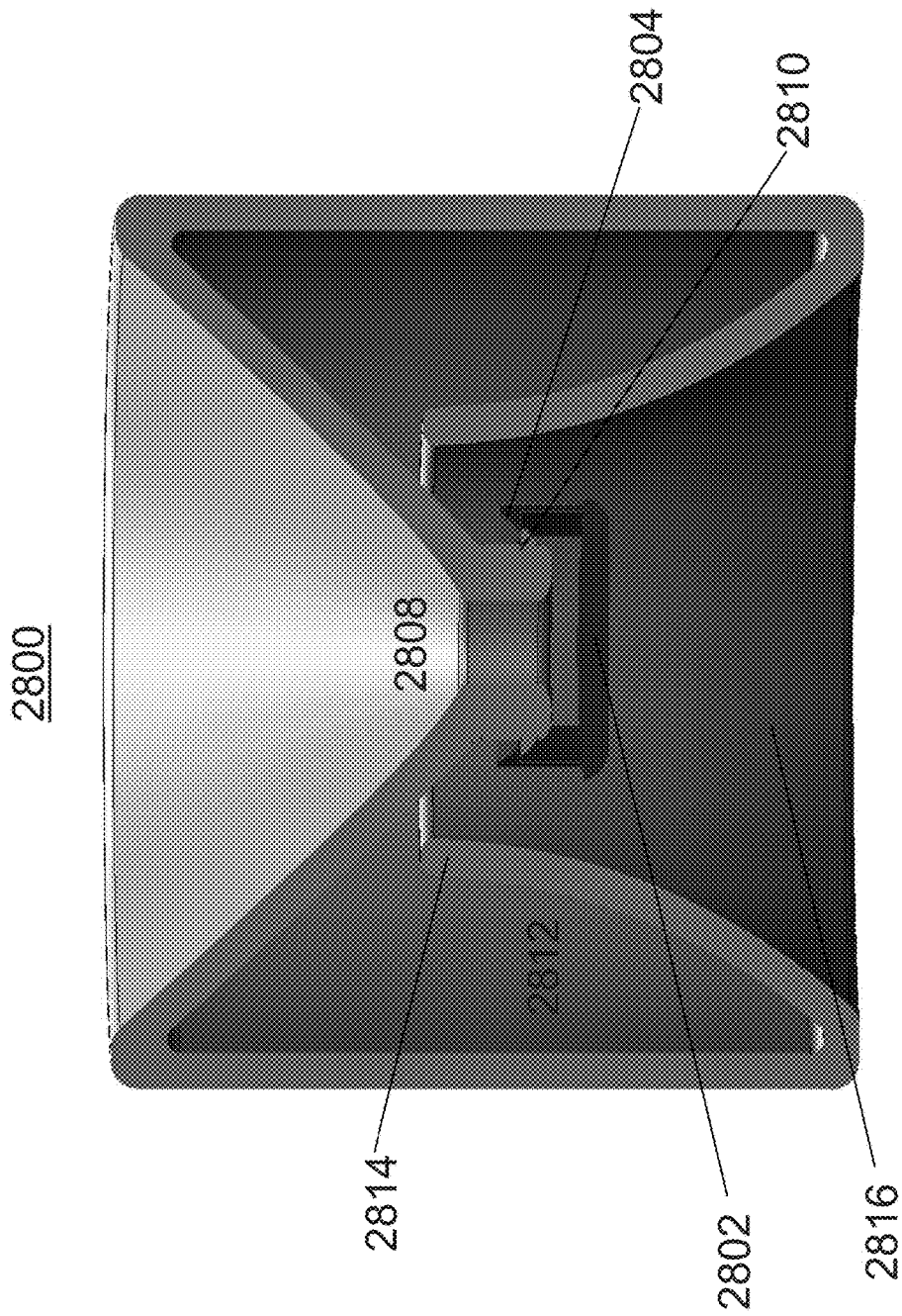

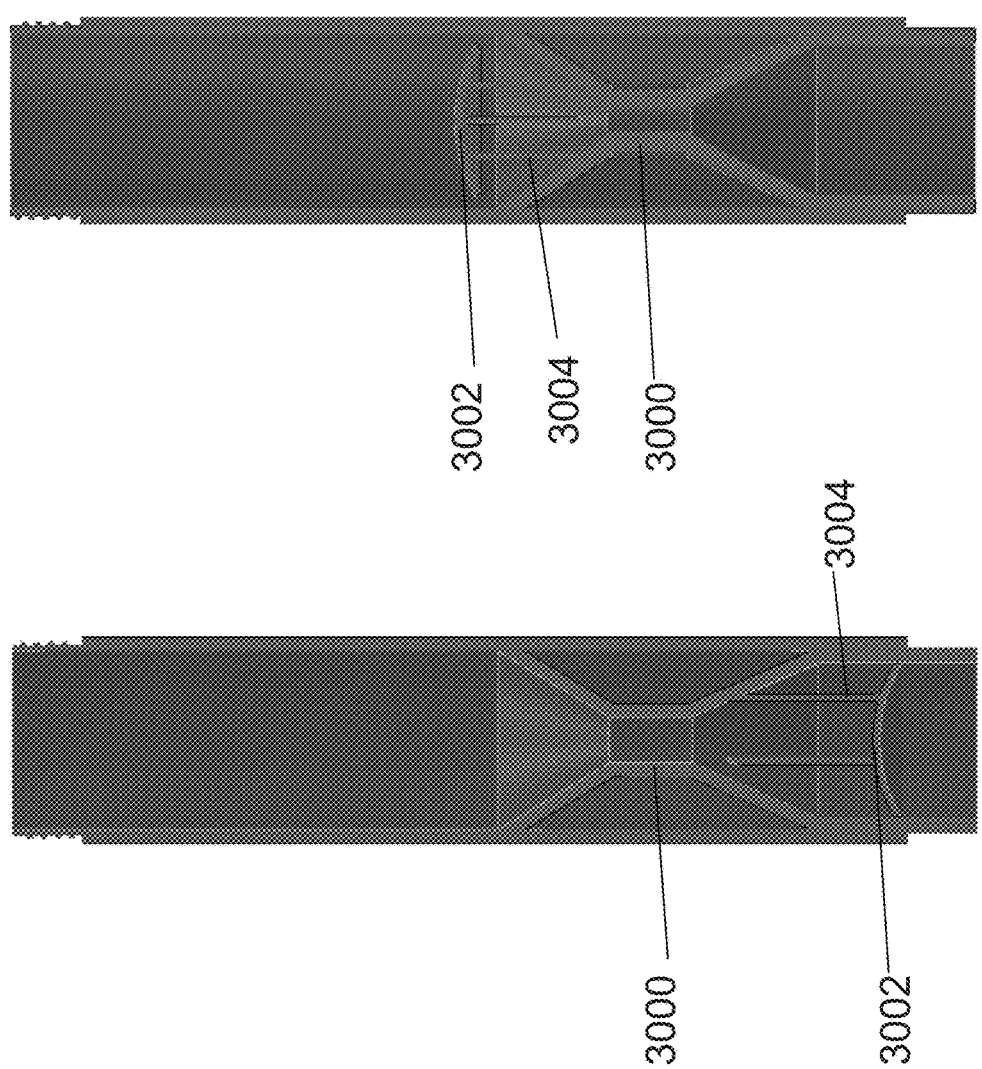

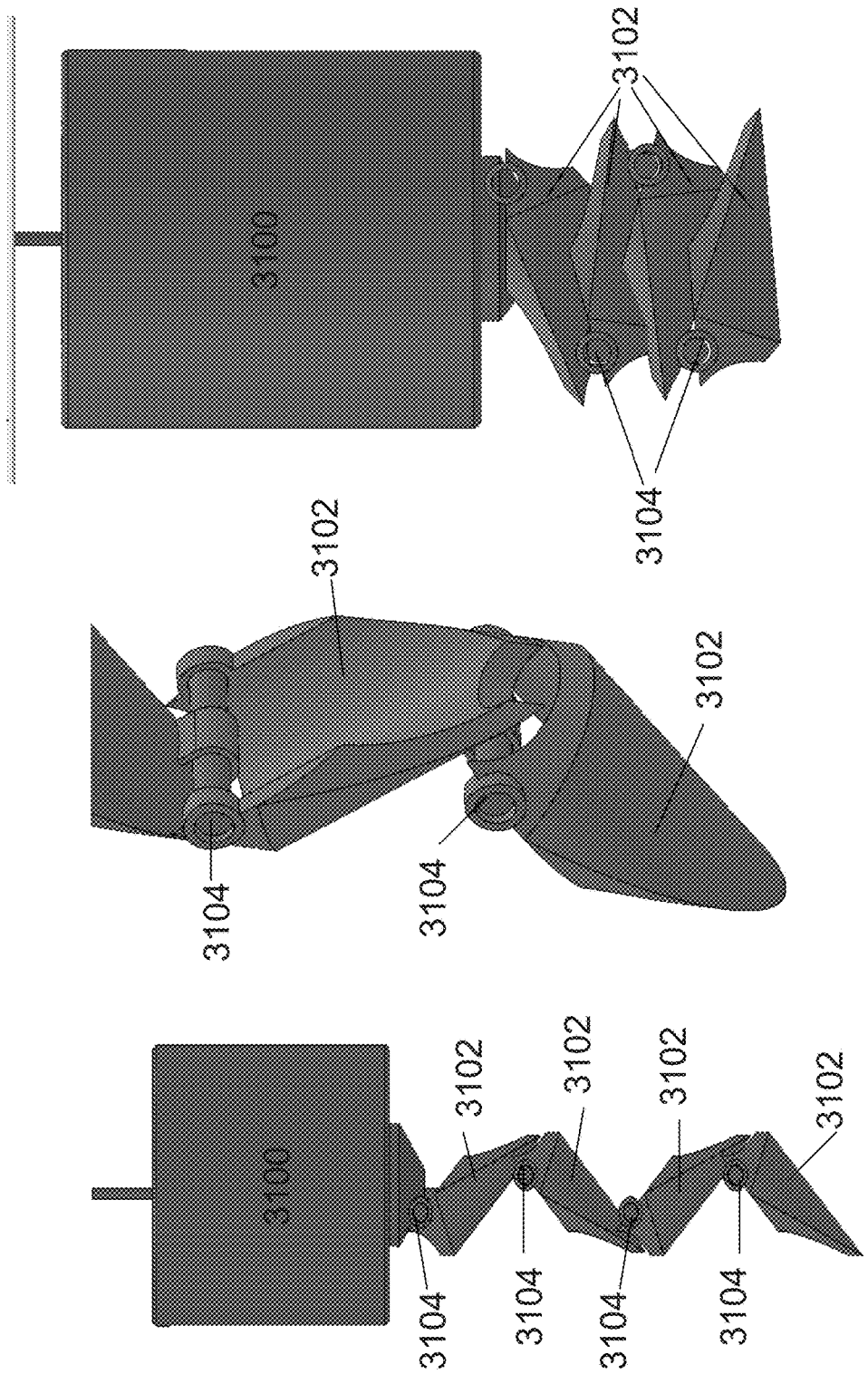

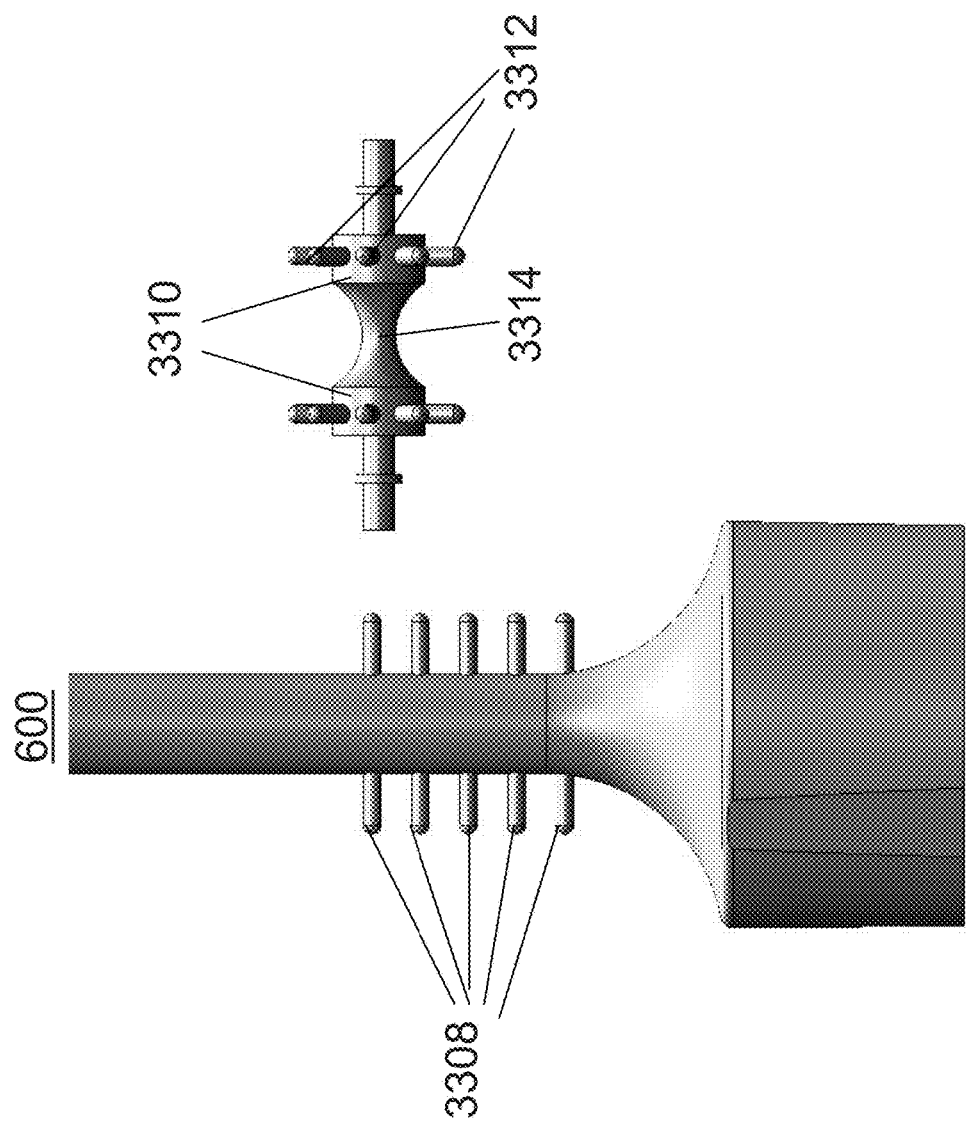

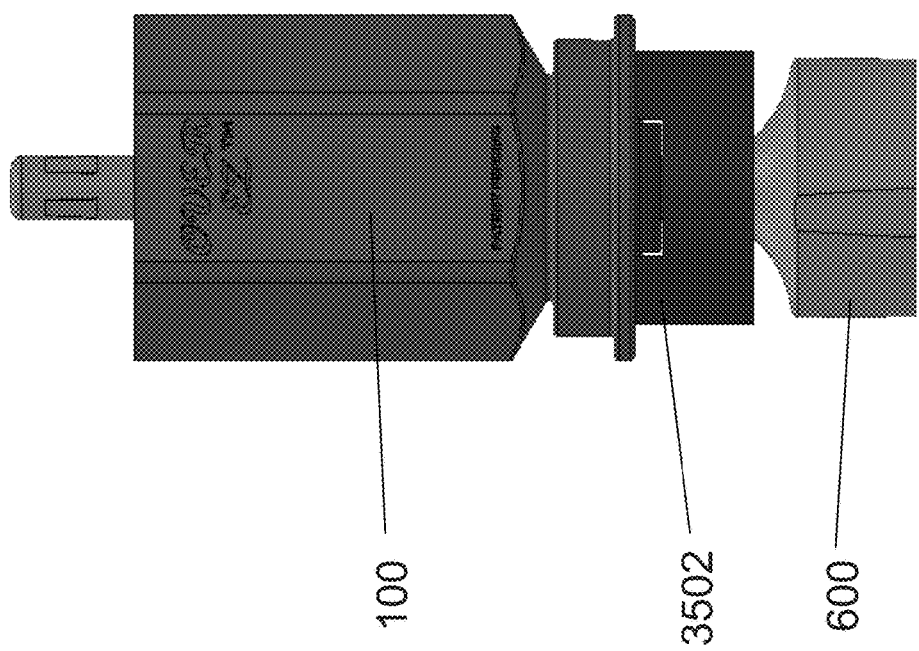

DEVICES AND METHODS FOR OVERLAYING BLOOD OR CELLULAR SUSPENSIONS

CROSS REFERENCE TO RELATED APPLICATION

The present application is a National Stage Entry of PCT/US12/50192 filed Aug. 9, 2012 and claims benefit of U.S. Provisional Patent Application No. 61/521,573 filed Aug. 9, 2011, the entire contents of which are incorporated herein be reference.

BACKGROUND

This invention relates to a thermoplastic device for overlaying blood or cellular suspension over a volume of density gradient contained in a centrifuge tube, such as a conical centrifuge tube, a round bottom tube, an ultra centrifuge tube, or any other type of centrifuge tube.

The isolation and preparation of leukocytes, more generally referred to as "white blood cells" (WBC's), from whole blood or cellular suspension using a density gradient is generally the first technique to be carried out in any immunological experiment. WBC's are the main components of our immune system and thus are the main target for experimentation.

While the density gradient protocol is efficient at yielding a high percentage of WBC's from a sample, it is time consuming, messy, and requires hours of hands-on training. The most time consuming part of the density gradient protocol is the "overlay", where blood or cellular suspension is carefully poured over the surface of the density gradient as to prevent any mixing of the two liquids. Two separate layers must be formed with minimal mixing in order to yield a sufficient number of cells. The overlay is completed by holding two centrifuge tubes together, one with density gradient and one with blood or cellular suspension, and slowly pouring the blood or cellular suspension over the density gradient liquid.

There are several major drawbacks to the overlay method in the density gradient protocol. Primarily, the protocol depends on the lab technician to judge how fast or slow to pour the blood or cellular suspension onto the density gradient liquid. This dependence on human technique frequently results in spills, mixing the blood/cellular suspension with the density gradient, or total loss of sample. In addition, the overlay method is time consuming and tedious. The majority of the time spent isolating WBC's is spent on the overlay method. Larger experiments that require a lot of WBC's are split into multiple experiments because there is simply not enough time in the day to overlay a large volume of blood or cellular suspension.

Clearly, then, there is a need for a device used to overlay blood or cellular suspension that can be used by any lab technician without prior training and that can speed up the overlay process. Such a device would virtually eliminate prior training or human error in the overlay process, dramatically reduce the time it takes to overlay, and increase yield by reducing spills.

Further, such a needed device would be relatively easy to manufacture on a large scale, use, dispose, and would allow much larger experiments to be performed. The present invention fulfills these needs and provides further related advantages.

SUMMARY

Described and claimed herein are devices and processes for overlaying a fluid, such as blood or a cellular suspension over a volume of a base material, such as Ficoll or any other suitable density gradient. In some applications, the base material is initially poured into a centrifuge tube (e.g., standard 50 ml or 15 ml conical tubes). The device at least partially defines a reservoir for temporarily storing the overlay fluid, a fluid barrier separating the reservoir and the container, one or more fluid channels across the fluid barrier, and an exhaust regulator. Certain features of the exhaust regulator and channels allow an adequately regulated, steady flow of blood or cellular composition into the conical centrifuge tube and onto the base material, without substantially disturbing a surface layer of the base material regardless of the level of skill or care of the clinician.

The devices and processes described and claimed herein offer certain advantages over existing overlay techniques. First, the fluid layering device requires no skill, thus eliminating prior training from others, mixing, spills, or ruined experiments. Next, the device dispenses blood/cellular suspension in an ordered, uniform fashion so that a perfect overlay occurs in the minimal amount of time. Multiple devices can be used at once to dramatically reduce the total time spent overlaying in an experiment. The device is sterile, disposable, and affordable—an economical and feasible alternative to the mainstream overlay technique in PBMC isolation. Other features and advantages of the present invention will become apparent from the following more detailed description, taken in conjunction with the accompanying drawings, by way of example, the principles of the invention.

In one embodiment, a fluid layering device is configured to control a flow of fluid into an open-ended container. The device includes a fluid barrier configured to prevent passage of fluid from a proximal reservoir toward a distal end of the open-ended container. A peripheral seal extends along an outer perimeter of the fluid barrier and is configured for sealing engagement along an interior surface of the open-ended container. The device further includes at least one groove formed in the peripheral seal. The at least one groove is configured to provide a controlled flow of fluid across the fluid barrier and along the interior surface of the open-ended container. The device also includes an exhaust vent configured to vent from the open-ended container gas displaced by the controlled flow of fluid.

In some embodiments, the device includes a proximal reservoir defined at least partially by a proximal surface of the fluid barrier.

In some embodiments, the reservoir is open-ended, defined by an elongated cylindrical wall extending proximally from the fluid barrier.

In some embodiments, the device includes a coupling arrangement adjacent to the open end of the reservoir.

In some embodiments, the device includes the coupling arrangement comprises a thread.

In some embodiments, the device includes the fluid barrier comprises at least one drain port in fluid communication with a proximal end of each of the at least one grooves.

In some embodiments, the device includes a proximal handle allowing for insertion and removal of the fluid layering device with respect to the open-ended container.

In some embodiments, the exhaust vent terminates in an exhaust port disposed along an outer surface of the fluid layering device.

In some embodiments, each of the at least one grooves extends helically along a cylindrical surface defining the peripheral seal.

In some embodiments, the device includes a shoulder positioned to abut at least a portion of a rim of the open-ended container when the fluid layering device is inserted therein, the shoulder position with respect to a proximal end of the fluid layering device to control height of the fluid barrier along a longitudinal axis of the open-ended container.

In some embodiments, the device is sterilized.

In some embodiments, the device includes is formed from material selected from the group consisting of: plastics; polymers; resins; glass; ceramics; metals; and combinations thereof.

In some embodiments, fluid stored within the fluid layering device is observable through a sidewall of the device.

In some embodiments, at least a portion of the fluid layering device is translucent or transparent.

In another embodiment, a process for controlling a flow of fluid into an open-ended container includes positioning a fluid barrier above a surface of a base material disposed in a distal end of the open-ended container. A first fluid is added into a reservoir positioned proximal to the fluid barrier. A flow of fluid is directed from the reservoir across the fluid barrier and into the distal end of the open-ended container, fluid passing the fluid barrier flowing toward the base material along an interior surface of the open-ended container. Gas displaced by the controlled flow of fluid is exhausted from the distal end of the open-ended container, such that a layer of the first fluid is deposited over the base material without substantially disturbing a surface of the base material.

In some embodiments, the process includes positioning the fluid barrier comprises inserting at least a proximal portion of a fluid layering device into an open end of the open-ended container.

In some embodiments, the process includes removing the fluid barrier from the open-ended container.

In some embodiments, the process includes centrifuging the layered material.

In some embodiments of the process, the base material is Ficoll.

In some embodiments of the process, the fluid is a cellular suspension.

In some embodiments of the process, the cellular suspension is blood.

In some embodiments of the process, a three or more fluids are deposited over each other in layers and each fluid layer does not substantially disturb the surfaces of adjacent fluid layers.

In some embodiments of the process, the base material is a cesium chloride density gradient.

In some embodiments of the process, isopycnic separation is used.

In some embodiments a fluid layering device configured to control a flow of fluid into an open-ended container includes means for positioning a fluid barrier above a surface of a base material disposed in a distal end of the open-ended container. The device also includes means for adding a first fluid into a reservoir positioned proximal to the fluid barrier and means for directing a flow of fluid from the reservoir across the fluid barrier and into the distal end of the open-ended container, wherein passing the fluid barrier flowing toward the base material occurs along an interior surface of the open-ended container. The device also includes means for exhausting from the distal end of the open-ended container gas displaced by the controlled flow of fluid.

In yet another embodiment, a fluid layering device configured to control a flow of fluid into an open-ended container containing a base material includes a longitudinally extending cylindrical side wall open at its proximal end and a fluid barrier disposed across a distal end of the cylindrical side wall, a proximal surface of the fluid barrier and an interior surface of the cylindrical side wall forming an open-ended reservoir. The device also includes an insertable portion extending distally from the fluid barrier. The insertable portion includes a longitudinally extending sealing wall positioned to form a fluid-tight seal along a peripheral interior surface of a proximal portion of the open-ended container and at least one groove extending along the sealing wall and terminating in a peripheral fluid port configured to ensure fluid flowing into the open-ended container flows along an interior surface of the open-ended container. The device also includes at least one drain in fluid communication between the reservoir and a proximal end of each of the at least one grooves and an exhaust vent in fluid communication with the open-ended container. The vent regulates the flow of gas displaced by the controlled flow of fluid, thereby contributing to a rate of fluid flow.

In some embodiments of the device, the at least one groove extends helically along the sealing wall.

In some embodiments the device further includes a threaded coupling engagement along a distal portion of the cylindrical wall.

In still yet another embodiment, a fluid layering device configured to control a flow of fluid into an open-ended container includes a fluid reservoir and a plunger. The fluid reservoir includes a housing defining an open-ended reservoir; a coupling portion attached to the housing, and configured for inserting into an open-ended container for sealing engagement along an interior surface of the open-ended container; and a central opening in the open-ended reservoir. The plunger includes a shaft inserted through the central opening in the open-ended reservoir; and a cylindrical cup attached to a lower end of the shaft.

In some embodiments of the device, the housing of the fluid reservoir includes a longitudinally extending cylindrical side wall open at its proximal end and a fluid barrier disposed across a distal end of the cylindrical side wall, a proximal surface of the fluid barrier and an interior surface of the cylindrical side wall forming the open-ended reservoir.

In some embodiments, the coupling portion of the fluid reservoir includes a longitudinally extending sealing wall positioned to form a fluid-tight seal along the interior surface of the open-ended container.

In some embodiments, the cup of the plunger further includes a helical ridge configured to engage the interior surface of the open-ended container. In a further embodiment, the coupling portion includes a helical channel configured to engage the helical ridge of the cup.

In some embodiments, the cylindrical cup is hollow and the plunger is configured to be buoyantly raised by a fluid in the open-ended container.

In some embodiments, the fluid reservoir includes an exhaust vent for venting gas from the open-ended container displaced by the addition of a fluid to the open-ended container.

In some embodiments, the fluid reservoir includes a shoulder positioned to abut at least a portion of a rim of the open-ended container when the fluid layering device is inserted therein.

In some embodiments, the shaft of the plunger is joined to the cylindrical cup via a sloped portion of the plunger.

In some embodiments, a diameter of the shaft of the plunger is substantially smaller than a diameter of the central opening to allow a fluid to flow through the central opening around the shaft.

In some embodiments, a diameter of the shaft of the plunger is similar to the diameter of the central opening, and the fluid reservoir includes at least one drain port to allow a fluid to flow from the fluid reservoir into the open-ended container.

In some embodiments, the fluid layering device is sterilized.

In some embodiments, the fluid layering device is formed from material selected from the group consisting of: plastics; polymers; resins; glass; ceramics; metals; and combinations thereof.

In yet still another embodiment, a method for controlling a flow of fluid into an open-ended container includes inserting a fluid layering device comprising a fluid reservoir and a plunger into a distal end of an open-ended container. The method also includes lowering the plunger to position a cup of the plunger substantially at or above a surface of a base material. The method further includes adding a first fluid into the fluid reservoir to flow into the distal end of the open-ended container and across an upper surface of the cup to be deposited over the base material without substantially disturbing the surface of the base material. The first fluid buoyantly raises the plunger as the first fluid is deposited over the base material.

In some embodiments, the method includes exhausting from the distal end of the open-ended container gas displaced by the controlled flow of the first fluid.

In some embodiments, inserting the fluid layering device into the distal end of the open-ended container includes inserting at least a proximal portion of the fluid layering device into the open end of the open-ended container.

In some embodiments, lowering the plunger further includes disengaging a threaded portion of the plunger from a corresponding threaded portion of the fluid reservoir. In a further embodiment, the method includes engaging the threaded portion of the plunger with the corresponding threaded portion of the fluid reservoir, and removing the fluid layering device from the open-ended container.

In another aspect, an apparatus is disclosued including: a rack configured to stabilize one or more containers to be used for fluid layering, wherein the rack is configured rest on a surface to support the one or more containers at angle relative to the surface.

In another aspect, a fluid layering device configured to control a flow of fluid into a container having an open top end and a closed bottom end is disclosed, the device including a trap member that may be inserted into or integral with the open ended container. In some embodiments, the trap member comprises: an inlet chamber for receiving the flow of fluid from the open top end of the container and having an opening that allows fluid flow out of the inlet chamber towards the closed bottom end of the container, a cap positioned at the opening configured to selectively allow and interrupt flow of fluid through the opening; a reservoir defined by the a wall of the inlet chamber and a partial wall located below the inlet chamber; and an exit chamber. In some embodiments, the trap member is configured such that upon receiving a the flow of fluid at the first opening of the inlet: initially the cap opens in response to the fluid to allow fluid flow through opening and the exit chamber to the bottom of the container; when the the fluid fills the container to a first level below the cap, the trap member directs at least a portion of the fluid flow to the reservoir; and when the fluid fills the container to a second level above the cap, the cap interrupts the flow of fluid through the second opening.

In another aspect, a fluid layering device is disclosed that is configured to control a flow of fluid into an open-ended container, the device including: a trap member configured to: operate in a first state to allow a first layer of fluid to be added to a closed bottom portion of the open the container; and operate in a second state to physically seal off a portion of the container containing at least a portion of the first layer in order to prevent mixing of the first layer with a subsequently added second layer of fluid.

Various embodiments may include any of the devices and techniques described above (or otherwise described herein) either alone or in any suitable combination.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4A is a side view of the fluid layering device of FIG. 1 aligned for insertion into an open ended conical container.

FIG. 4B illustrates the fluid layering device after insertion into the conical container.

FIG. 6A-6D illustrate operation of an embodiment of a fluid layering device in controlling flow of a fluid into an open ended conical container containing a base material.

FIGS. 10A, 10B, 10C, and 10D illustrate still yet another embodiment of a fluid layering device, in a front view, rear view, top view, and bottom view, respectively.

FIGS. 10E and 10F illustrate an embodiment of the fluid layering device illustrated in FIGS. 10A-10D, in side view and section view, respectively.

FIG. 17A-17B illustrate an implementation of a fluid layering device.

FIG. 18 illustrates another implementation of a fluid layering device.

FIG. 20A-20B illustrate a bottom portion of a fluid layering device that can be used to secure a plunger.

FIG. 22A-22C illustrate another implementation of a plunger.

FIG. 24 illustrates a fourth implementation of a plunger.

FIG. 25A-E illustrate a fifth implementation of a plunger along with associated shells.

FIG. 28D illustrates a cross sectional view of the trap insert of FIG. 28A with the cap of FIG. 28C installed.

FIG. 30A-B illustrate cylinder and an hourglass insert for use in a fluid layering process.

FIG. 31A-C illustrate various views of a series of scoops for use in a fluid layering process.

FIG. 33A-C illustrate a second implementation of a mechanism for securing a plunger.

FIG. 35A-D illustrate a fourth implementation of a mechanism for securing a plunger.

DETAILED DESCRIPTION

Described herein are examples of devices and processes configured to overlay at least one sample fluid, such as blood or a cellular suspension, onto at least one base material, to create at least two fluid layers. The base material can include, but is not limited to, sugar density gradients such as Ficoll, Percoll, Isopercoll, and isopycnic sucrose density gradient. The cellular suspension can include, but is not limited to, monocyte cultures; Tc clones; islets of Langerhans from pancreatic tissue (e.g., Dellê et al., The Use of Iodixanol for the Purification of Rat Pancreatic Islets, TRANSPLANTATION PROCEEDINGS, Vol. 39, No. 2, pages 467-469); neural cells from brain tissue (e.g., Sims & Anderson, Isolation of mitochondria from rat brain using Percoll density gradient centrifugation, NATURE PROTOCOLS, Vol. 3, 2008, pages 1228-1239); ovarian follicles (e.g., Martinez-Madrid et al., Ficoll density gradient method for recovery of isolated human ovarian primordial follicles, FERTILITY AND STERILITY, Vol. 82, No. 6, 2004, pages 1648-1653); spermatozoa from epididymis (e.g., Haldar et al., Ficoll Gradient Isolation of Immature Sperm of High Purity and Intactness From Goat Epididymis, SYSTEMS BIOLOGY IN REPRODUCTIVE MEDICINE, Vol. 24, No. 2, 1990, pages 125-128); and plant cells (e.g., Attree & Sheffield, An evaluation of Ficoll density gradient centrifugation as a method for eliminating microbial contamination and purifying plant protoplasts, JOURNAL PLANT CELL REPORTS, Vol. 5, No. 4, 1986, pages 288-291; Liang et al., Isolation of Spinach Leaf Peroxisomes in 0.25 Molar Sucrose Solution by Percoll Density Gradient Centrifugation, PLANT PHYSIOL., Vol. 70, 1982, pages 1210-1212).

In general, the fluid layering device can be coupled through a coupling extension to an open end of a container, such as a conical centrifuge tube, already including the base material. Once attached, the device regulates flow of the first fluid from the reservoir into the conical tube so that a suitable overlay layer is formed without substantially disturbing a surface of the base material, regardless of the skill and care of the user.

Figure 1:
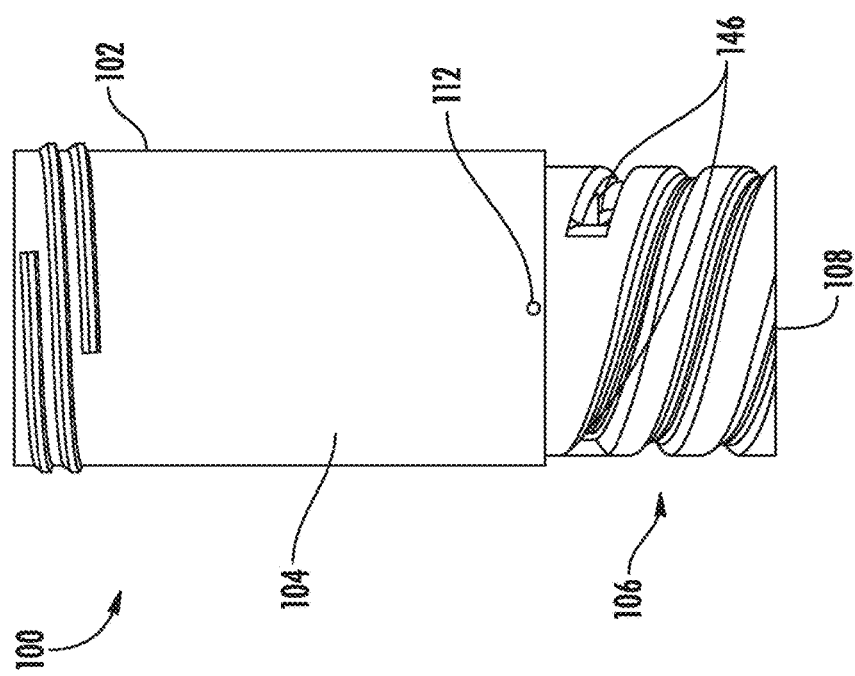
FIG. 1 illustrates a side view of one embodiment of a fluid layering device.

A side view of an embodiment a fluid layering device 100 is illustrated in FIG. 1. The device 100 includes an elongated cylindrical housing 102 defining an open ended reservoir 104 at one end and an insertable coupling portion 106 at an opposite end. One or more helical channels 108 are defined along a peripheral side wall 144 of the coupling portion 106. The helical channels 108 extend from a top or proximal end of the coupling portion 106 to a bottom or distal end of the coupling portion 106. In some mebodiments, there are also a number of triangular openings that connect the cylindrical reservoir 104 to helical channels 108 that wrap around the coupling portion or base 106 of the device 100 (the base is fully inserted into the conical centrifuge tube). The number of triangle openings 110 and helical channels 108 depend on the size/model of the invention. There is a circular exhaust vent 118, which allows gas to be vented from the inside of the conical centrifuge tube to the environment.

In at least some embodiments, the entire device 100 can be made of a common material. In this embodiment, the device is made from a moldable material, such as a translucent plastic such as polystyrene (PS), acrylonitrile butadiene styrene (ABS polypropylene (PP), polycarbonate (PC), Polyallomer, Ultra-clear, Polycarbonate, Stainless steel, cellulose propionate or corex/pyrex. The reason for translucency is so the user can view the progress of the blood/cellular suspension in the device in order to determine whether or not the process has completed. The engineering grade plastics (PS, ABS, PC) are required so that the device will retain structural integrity when inserted to and removed from its conical centrifuge tube. In some embodiments, the material of the device 100 is selected in order to create a seal with the container used for layering the fluids. For example, a relatively flexible material can be selected for the device 100 when the device 100 is to be used with a relatively inflexible container. In this example, a seal is created by the compression of the flexible device 100 against the inflexible sides of the container. Similarly, if the container to be used is relatively flexible, an inflexible material can be selected for the device 100.

Figure 2:
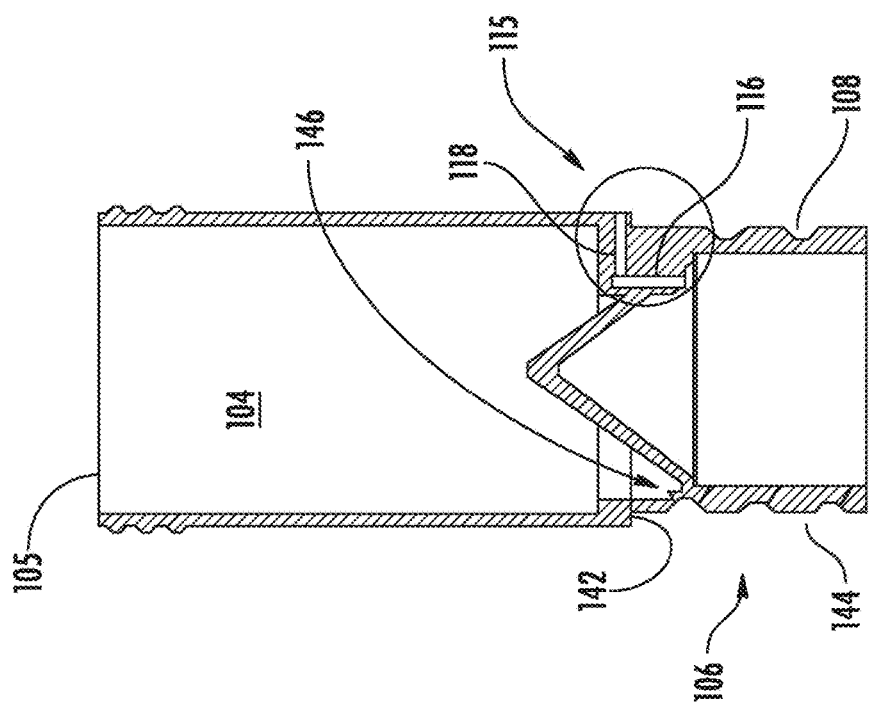
FIG. 2 illustrates a longitudinal cross-section of FIG. 1.

FIG. 2 details the cross-section of the device 100 and illustrates the exhaust vent 112 and an interior barrier wall. In the illustrative embodiment, the barrier wall is a conical divider 114. The exhaust vent is composed of a rectangular tunnel 116 that leads from the conical centrifuge volume to a circular tunnel 118 that exits a proximal side wall of the device. The cross-section of this tunnel 116, 118 determines the rate of gas exiting the conical tube and thus the rate of the blood/cellular suspension entering the conical tube via the helical channels 108. The rate at which the blood or cellular suspension enters the conical tube depends solely on the rate at which gas exits the tube. The conical divider physically separates the contents of the cylindrical reservoir from the conical centrifuge tube. Its conical shape assists in the complete evacuation of the reservoir's contents into the centrifuge tube.

Figure 3B:
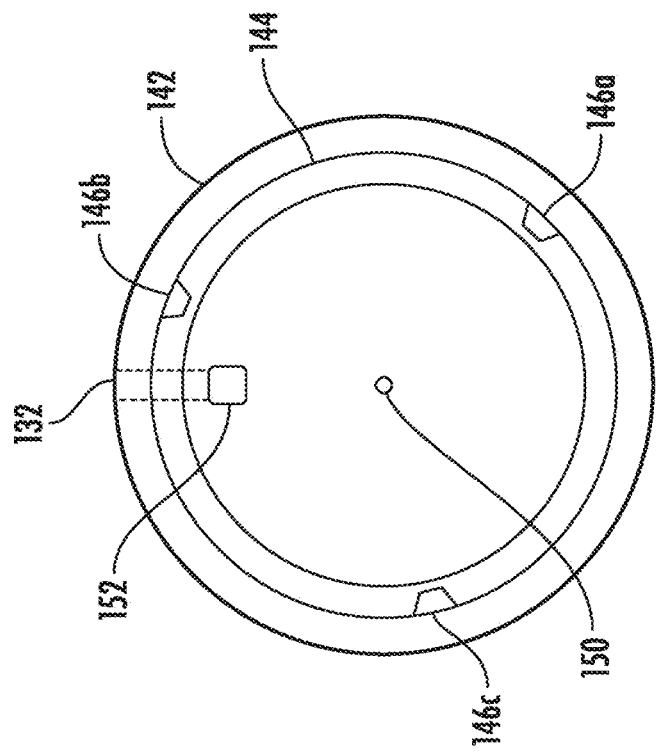
FIG. 3B is a distal end view of the fluid layering device of FIG. 1 and FIG. 2.
Figure 3A:
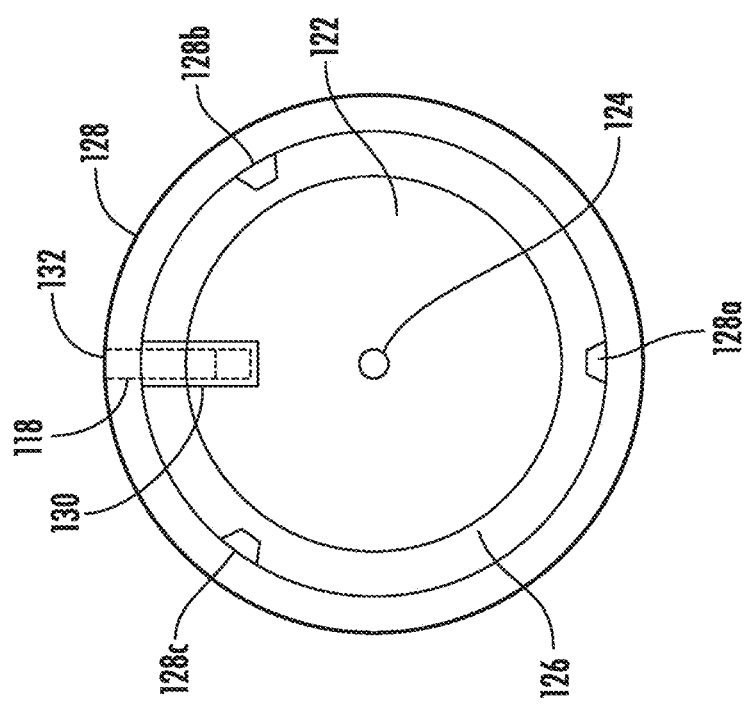
FIG. 3A illustrates a proximal end view of the fluid layering device of FIG. 1 and FIG. 2

FIG. 3A illustrates a proximal end view of the fluid flow device illustrated in FIG. 1 and FIG. 2. A proximal end or rim of the reservoir wall 120 defines an open end of the reservoir 104. A proximal surface 122 of the conical divider 114 defines a bottom of the reservoir 104. The proximal surface 122 follows the contour of the conical divider 114 terminating in a conical peak 124 centrally located along a base surface of the reservoir 104. An annular trough 126 extends between a base portion of the proximal surface 122 and the base of the interior surface of the reservoir walls 120. One or more openings 128a, 128b, 128c (generally 128) are located along the annular trough 126. In the illustrative embodiment three triangular openings 128 are disposed about the annular trough. Also visible is a proximal portion of an exhaust vent housing 130. The exhaust vent exit tunnel 118 is illustrated in phantom, exiting the reservoir wall 120 at the exhaust vent outlet port 132. A fluid placed in the reservoir 104 will be directed by the conical peak 124 toward the annular trough 126. The fluid is able to exit the reservoir 104 through the triangular openings 128.

Illustrated in FIG. 3B is a distal end view of the fluid layering device 100. A proximal extension 106 defines along its outer peripheral surface a peripheral sealing wall. An annular shoulder 142 is defined along a base portion of the reservoir wall 120 extending in radial direction beyond the peripheral sealing wall 144. One or more fluid ports are defined along a proximal end of the proximal extension 312. In the illustrative embodiment three fluid ports 146a, 146b, 146c (generally 146) are disposed evenly about the circumference of the proximal extension 106. A distal surface 148 of the conical divider 114 extends across an opening of the proximal extension 106. An inner conical peak 150 is shown centrally to the distal surface 148. The distal surface 148 includes an exhaust vent inlet port 152. The exhaust vent inlet port 152 is in fluid communication with the exhaust vent exit tunnel 118 allowing gas to exit through the exhaust vent outlet port 132.

Preferring to FIG. 4A, the fluid layering device 100 is positioned in axial alignment with an elongated open end conical container 200. The fluid layering device 100 is positioned such that a distal end of the insertable portion 106 faces an open end 202 of the open ended container 200. Coupling of the two devices is accomplished by advancing the fluid layering device 100 towards the open end 200 advancing the insertable portion 106 within the open end 202 of the container 200. The fluid layering device 100 is advanced axially until the annular shoulder 142 abuts an annular rim 204 of the open end 202. An illustration of the fluid layering device 100 fully inserted within the open ended container 200 is shown in FIG. 4B. Also visible is the exhaust vent outlet port 132 positioned proximally to the annular shoulder 142 such that the exhaust outlet port 132 remains unobstructed after insertion.

Figures 5A, 5B:
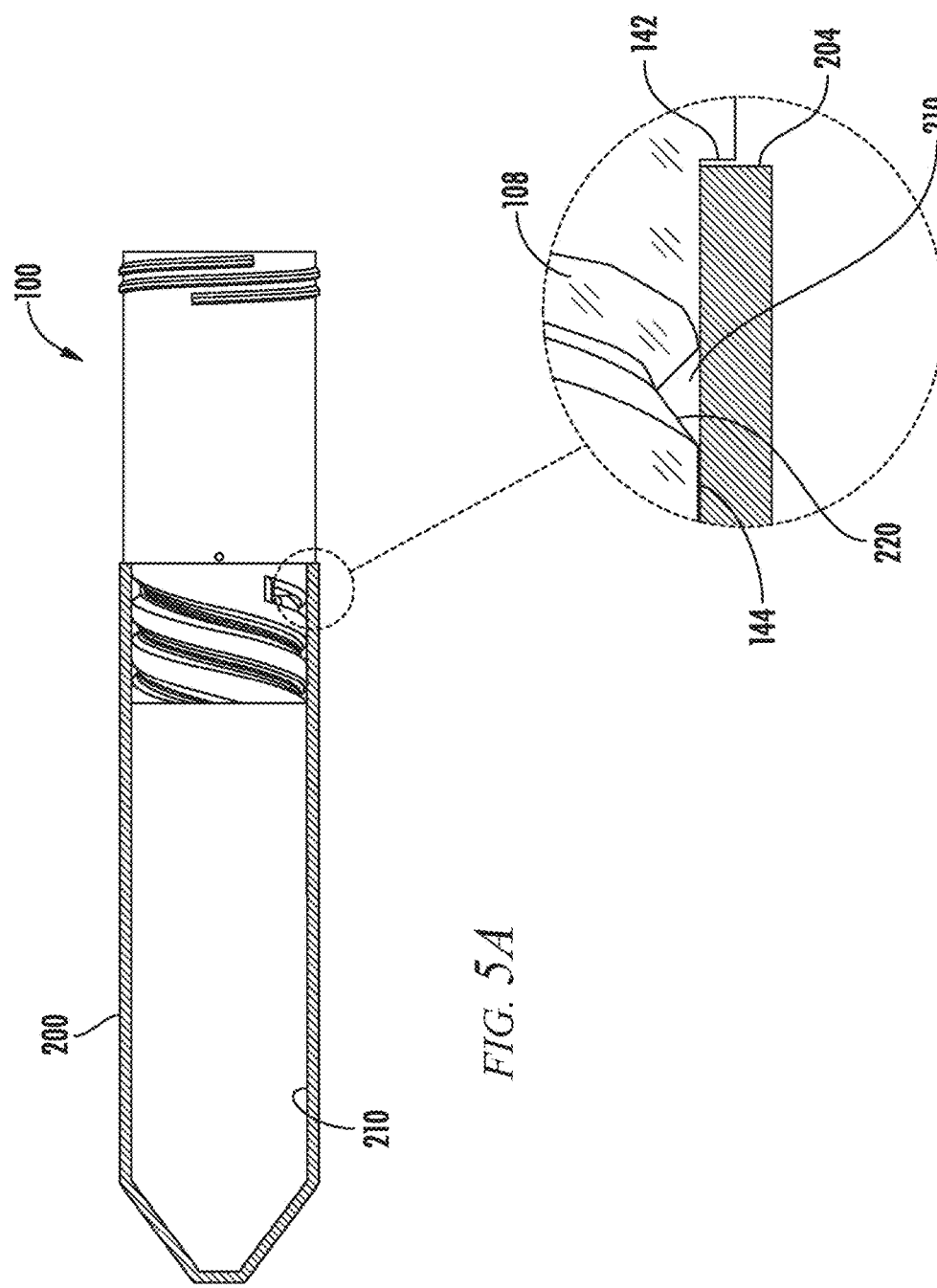
FIG. 5A illustrates a cross-section of the conical open ended container with the fluid layering device of FIG. 1 and FIG. 2 inserted into its open end.
FIG. 5B illustrates in more detail, engagement of an insertable portion of the fluid layering device with an interior surface of the open ended conical container.
Figure 7A:
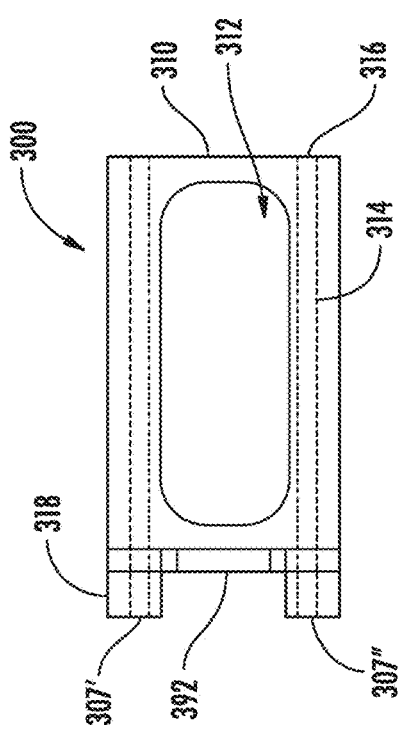
FIG. 7A-7D illustrate an alternative embodiment of a fluid layering device.
Figure 7D:
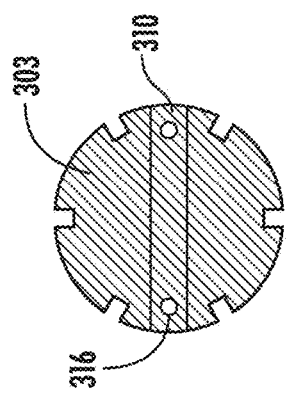
Figure 7C:
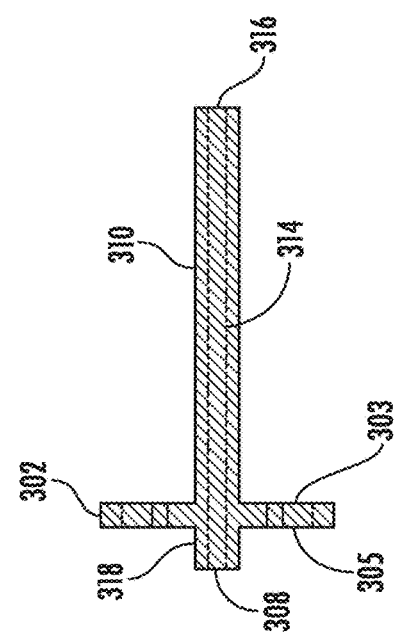
Figure 7B:
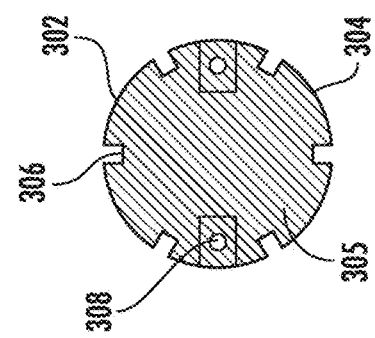

Illustrated in FIG. 5A a is a lateral cross-section of the open ended container 200 with the fluid layering device 100 fully inserted into its open end 202. FIG. 5B illustrates in more detail arrangement of the peripheral sealing wall 144, the helical groove 108 and an inner wall surface 210. In particular a fluid channel 220 is formed along the helical groove 108 being defined by the helical groove 108 and an adjacent portion of the inner wall surface 210. Also shown in more detail is the abutting arrangement of the shoulder 142 against the annular rim 204.

Operation of an embodiment of a fluid layering device in controlling flow of a fluid into an open ended conical container is illustrated in the series of FIG. 6A through FIG. 6D. Initially, a base material, such as Ficoll, is inserted into an open end of the upright container 200. The base material 230 pools along the conical bottom end, such that a surface of the base material is spaced apart from the open end 202 by a distance $h_1$. Referring to FIG. 6A, the fluid layering device 100 is coupled to the container 200 as described above and illustrated in FIG. 4B and FIG. 5A. When fully inserted, a distal end of the insertable portion 106 resides at a height $h_2$ above the surface of the base material. The reservoir 104 extends proximally from the open end 202 to a height $h_3$. As illustrated in FIG. 6B, a first fluid, in this instance a cellular suspension—blood, is poured into an open end 105 of the reservoir 104. Preferably, the container-fluid layering device arrangement is positioned in upright or vertically, such that gravity will drive the flow of blood into the container 200. In some embodiments, the arrangement can be positioned at an angle, but preferably not much more than about 30 degrees measured from vertical.

As shown in FIG. 6C, gravity induces a downward flow, forcing blood 240 from the reservoir 104 into the channels formed between helical grooves 108 and the inner surface of the container 210. The fluid 240 exits the grooves 108 along the interior walls 210 of the substantially upright container 200. Gravity continues to drive blood flow 242 downward towards the exposed surface of the base material 230. Surface tension keeps the blood flow 242 substantially directed along the inner side walls 210. As the volume of blood increases in a layer above the base material 230, air pressure within the chamber 244 increases. The exhaust vent 115 allows air to bleed off from the chamber 244, thereby reducing the pressure and allowing for continued blood flow 242. Careful selection of the dimensions of the exhaust vent 115 can be used to control flow of blood 242 into the container 200. For example, a substantially narrow exhaust vent 115 restricts the flow of gas similarly restricting flow of blood 240 into the chamber 244. When the reservoir 104 contents have been substantially transferred, the fluid layering device 100 can be removed carefully as shown in FIG. 6C. Care must be exercised when separating the device 100 from the container so as not to disturb the layered arrangement of fluid 240 and base material 230 (e.g., blood and Ficoll). In most applications and particularly when working with blood 240, the fluid layering device 100 is preferably sterilized. Although it may be possible to re-sterilize (e.g., autoclave) the device 100, it is generally anticipated that it will be disposable based on the relative simplicity of design and minimum costs.

An alternative embodiment of a fluid layering device 300 is illustrated in FIG. 7A-7D. The device 300 includes a barrier wall 302 defining a perimeter conforming to a lateral cross section of the open ended container 330. In the illustrative embodiment, the perimeter is substantially circular. The barrier wall 302 defines a proximal surface 303 facing the fluid reservoir and a distal surface 305 facing the base material. A peripheral sealing wall 304 extends between the proximal surface 303 and the distal surface 305 and along the outer perimeter of the barrier wall 302. When inserted into an open end of the container 330, the barrier wall prevents fluid flow from the reservoir toward the base material.

The fluid layering device 300 also includes one or more grooves 306 formed in the peripheral sealing wall 304, configured to allow a controlled flow of fluid from the reservoir toward the base material. In the illustrative embodiment, six such grooves 306 are evenly distributed around the circular perimeter of the barrier wall 302. Each groove is formed as rectangular groove 306. The rectangular shape of the groove 306 is not meant to be limiting in any way. Other shaped grooves are contemplated, such as triangular, elliptical, circular, polygons, random shapes, and combinations of any such shaped. In the illustrative embodiment, the grooves are directed parallel to a longitudinal axis of the device. In some embodiments, the grooves may be angled, and/or curved, for example, in a helix arrangement. It is not necessary that all of the grooves 306 be identical in size, shape, or orientation.

The fluid layering device 300 also includes one or more exhaust vents. In the illustrative embodiment, the device 300 includes two such vents. Each exhaust vent 307', 307" (generally 307). Each vent 307 includes an elongated exhaust vent lumen 314 defined by a proximal handle 310 and extending between an exhaust vent inlet port 308 and an exhaust vent exit port 316. The handle 310 extends proximally away from the proximal surface of the barrier wall 302. Preferably, the handle 310 extends axially for a length sufficiently longer than any intended insertion depth, such that at least a proximal portion of the handle 310 extends beyond an open end of the container 330. In some embodiments, the handle includes an open area to facilitate removal of the fluid layering device 300 from the container by providing a surface upon which a finger, fingers, or suitable instrument may apply an axial removing force to remove the device 300 from the container 330.

Operation of an embodiment of the alternative embodiment of the fluid layering device illustrated in FIGS. 7A-7D and described above is illustrated in the series of FIG. 8A-8C. Once again, a base material, such as Ficoll is inserted into an open end of the upright container 330. The base material pools along the conical bottom end 331, such that a surface 333 of the base material 319 is spaced apart from the open end 332 by a distance $h_1$. Referring to FIG. 8A, a distal portion of the fluid layering device 300 including the barrier wall 302 is inserted into the open end of the container 330. When fully inserted, a distal surface of the barrier wall 302 resides at a height $h_2$ above the surface 333 of the base material 319 as illustrated in FIG. 8B. A reservoir 332 extends proximally from a proximal surface of the barrier wall to the open end to a height $h_3$. A proximal portion of the handle remains exposed, extending to a height $h^5$ measured from the open end 332. Preferably, a sufficient portion of the open area 312 remains exposed to allow for insertion of a finger or suitable instrument during removal process.

A first fluid, in this instance a cellular suspension—blood, is poured into the open end 332 of the reservoir. Once again, the container-fluid layering device arrangement is preferably positioned upright or vertically, such that gravity will drive the flow of blood 350 into the container 330. In some embodiments, the arrangement can be positioned at an angle, but preferably not much more than about 30 degrees measured from vertical.

Figure 8C:
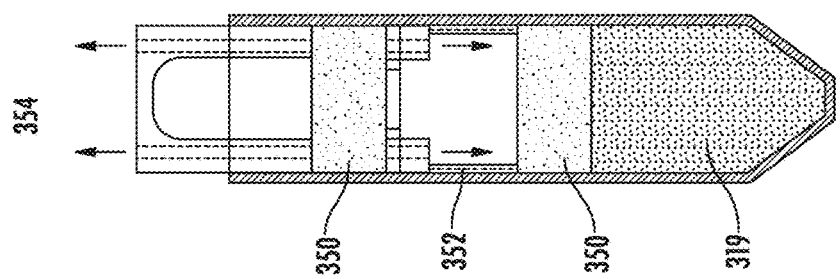
FIG. 8A-8C illustrate insertion of the embodiment of the fluid layering device illustrated in FIG. 7A-7D into an open end of the conical container and its direction of a fluid flow into the container.
Figure 8B:
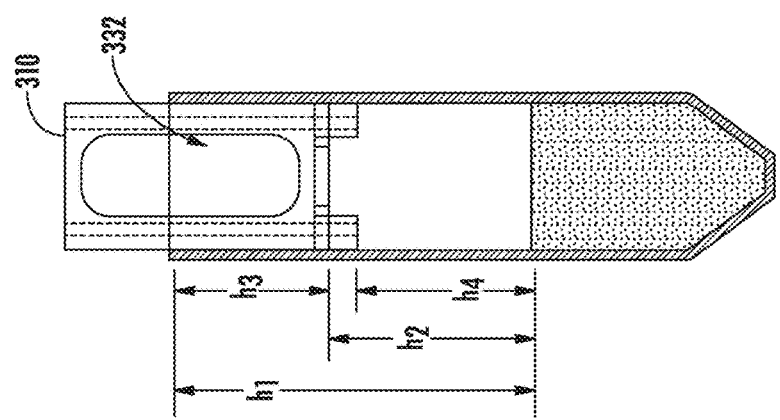
Figure 8A:
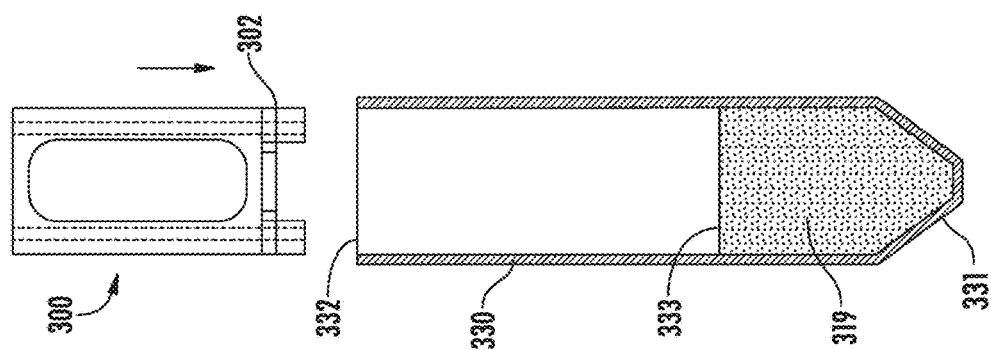

As shown in FIG. 8C, gravity induces a downward flow, forcing blood 350 from the reservoir 332 into the channels formed between grooves 306 (FIG. 7C and FIG. 7D) and the inner surface of the container 330. The blood 350 exits the grooves 306 along the interior walls of the substantially upright container 330. Gravity continues to drive blood flow 352 downward towards the exposed surface 333 of the base material 319 (e.g., Ficoll). Surface tension keeps the blood flow 352 substantially directed along the inner side walls. As the volume of blood increases in a layer above the base material, air pressure within the chamber increases. The exhaust vent allows exhausted air 354 to bleed off from the chamber, thereby reducing the pressure and allowing for continued blood flow.

As before, careful selection of the dimensions of the one or more exhaust vents can be used to control flow of blood 352 into the container 330. For example, a substantially narrow exhaust vent restricts the flow of gas similarly restricting flow of blood into the chamber. When the reservoir contents have been substantially transferred, the fluid layering device 300 can be removed carefully by puling the exposed portion of the handle 310. Care must be exercised when separating the device from the container so as not to disturb the layered arrangement of blood 352 and base material 319.

Figure 9:
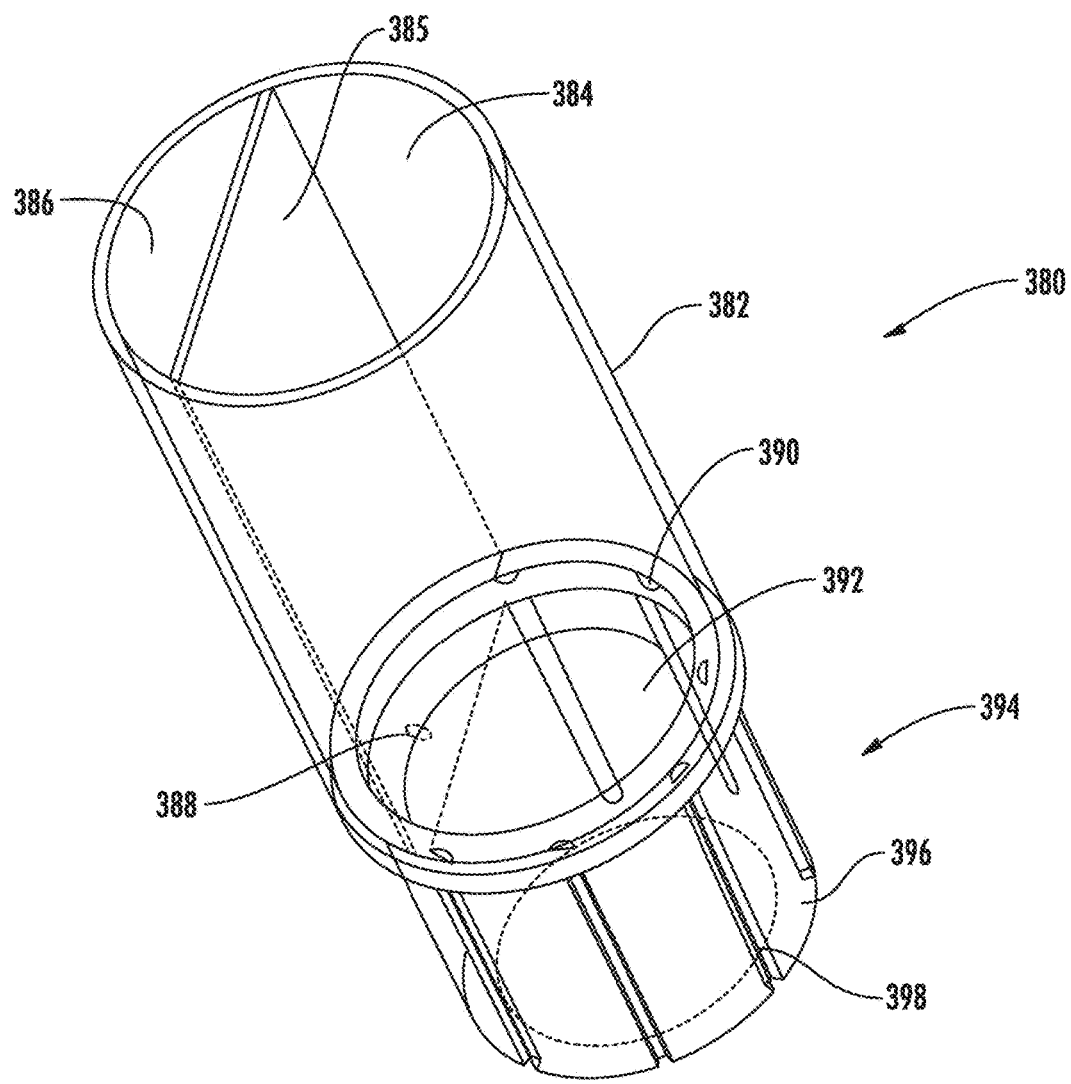
FIG. 9 illustrates yet another embodiment of a fluid layering device.

FIG. 9 illustrates yet another embodiment of a fluid layering device 380. The device 380 includes a proximal reservoir 382 and an insertable base portion 394. The reservoir 382 includes an open ended fluid chamber 384 and an elongated side wall 385 extending along a cord dissecting a cylindrical wall of the reservoir 382. Fluid poured into the open end portion 384 flows toward a barrier wall 392 forming a base portion of the reservoir 382. One or more drain apertures 390 are disposed along an outer periphery of the barrier wall 392, allowing fluid stored within the container to enter one or more longitudinally extending channels 398 defined along a peripheral sealing wall 396. Fluid flows along the longitudinal channels 398 between the channels 398 and an interior wall 210 of the open-ended container 200. Gas displaced by the inflowing fluid exits the container 200 through an exhaust vent 388. The exhaust vent directs expelled gas (e.g., air) into a vent portion 386 defined between an opposite side of the elongated separating wall 385 and an opposing portion of the cylindrical side wall, such that exiting exhaust air is not interfered with by fluid stored within the reservoir 382.

Referring briefly back to FIG. 6A, in some embodiments of fluid layering devices, due to the length of distance $h_2$, a first fluid may accelerate and achieve such velocity that, rather than layering on a second fluid, the first fluid brakes the surface tension of the second fluid and unacceptably mixes. Accordingly, in many embodiments, it may be desirable to reduce distance $h_2$. In one such embodiment of a fluid layer device, the device may comprise a plunger, which may be lowered to the surface of a second fluid, or just above the surface of the second fluid, reducing distance $h_2$ accordingly and reducing the velocity of the first fluid prior to contact with the second fluid. The plunger may be buoyant in the first fluid, such that, as the first fluid is added to the vessel, the plunger is forced upward by displacement and remains at the upper surface of the first fluid.

Figure 10C:
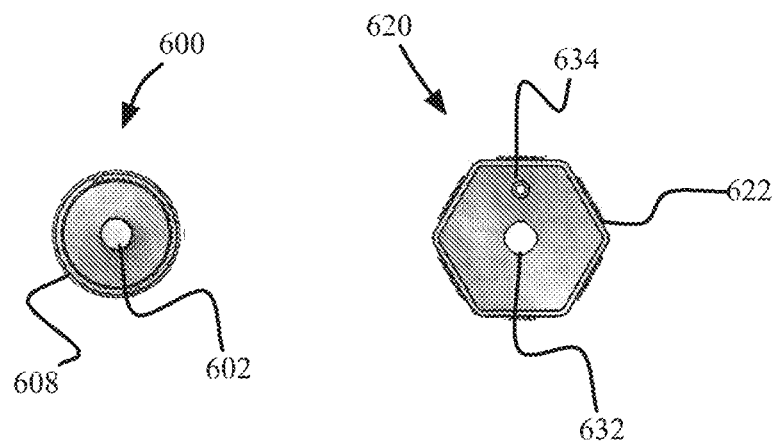

FIGS. 10A-10H illustrate an embodiment of such a fluid layering device incorporating a plunger. Referring first to FIG. 10A, illustrated is a front view of an embodiment of a fluid layering device comprising a reservoir 620 and plunger 600. In brief overview, a plunger 600 may comprise a shaft 602, which may include a grip 604, and a broadened terminal end 608. The shaft 602 may broaden into terminal end 608 via a sloping connection 606. In some embodiments, terminal end 608 may comprise a threaded portion 610. Reservoir 620 may comprise an elongated housing 622 defining an open ended reservoir at one end and an insertable coupling portion 624 at an opposite end. The coupling portion 624 may join to the housing 622 via an annular shoulder 626. In some embodiments, the reservoir may include a gas displacement port or exhaust vent 628.

In operation, described in more detail below, plunger 600 may be inserted in reservoir 620 with shaft 602 extending through an opening in the center of the open ended reservoir. In some embodiments, threaded portion 610 of the terminal end 608 may be engaged with a similar threaded portion inside of the insertable coupling portion 624. When the coupling portion 624 of reservoir 620 is inserted into a cylindrical vessel, such as a centrifuge tube, plunger 600 may be disengaged or unscrewed from the threads of the insertable coupling portion 624, and/or depressed or lowered, allowing shaft 602 to slide through the opening of the open ended reservoir, lowering terminal end 608 to the level of a fluid in the vessel. When a second fluid is added to the reservoir, the second fluid may flow through the opening or ports situated around the opening, down shaft 602, and to terminal end 608. The second fluid may further flow around threaded portion 610 to layer on top of the first fluid in the vessel. As the second fluid is added to the vessel, the terminal end 608 may be buoyed up, raising the plunger 600 accordingly. Once the reservoir 620 has been emptied, the plunger 600 may be raised from the surface of the second fluid, and/or may be screwed to engage threads 610 with corresponding threads in insertable coupling portion 624. In many embodiments, the combined reservoir 620 and plunger 600 may be then removed from the vessel and discarded, recycled, or otherwise reused.

Still referring to FIG. 10A and in more detail, in some embodiments, a fluid layering device may comprise a plunger 600, which may include a shaft 602. In many embodiments, shaft 602 may be circular in cross section, while in other embodiments, shaft 602 may be square, triangular, pentagonal, hexagonal, or any other shape to fit a corresponding hole in reservoir 620. Shaft 602 may be of varying lengths in different embodiments, depending on a vessel to be used. For example, shaft 602 may have a length of reservoir 620 plus the length of a vessel the fluid layering device is to be used with, plus an additional portion to allow a user to manipulate the shaft at a grip 604. This allows the plunger to be fully lowered into a vessel while reservoir 620 is engaged at the mouth of the vessel, with the grip 604 still extending past the opening of reservoir 620 and remaining clear of any fluid in reservoir 620. In other embodiments, shaft 602 may be shorter, in that the plunger may not need to be lowered to the bottom of a vessel to layer a first fluid on top of a second fluid already in the vessel. In many embodiments, shaft 602 may be hollow or partially hollow, aiding to the buoyancy of plunger 600. In many such embodiments, shaft 602 may be closed at an upper or top end, and open at terminal end 608. Shaft 602, as well as other parts of plunger 600 and/or reservoir 620, may be made of any suitable material, including an engineering grade plastic (PS, ABS, PC), glass, metal, or other material.

In some embodiments, shaft 602 may comprise a grip 604. In some embodiments, grip 604 may comprise a textured portion of shaft 602, or may be cut into a multi-sided portion allowing easier rotation or manipulation. For example, in one such embodiment, shaft 602 may be circular in cross-section, and grip 604 may be hexagonal in cross-section, allowing a user's fingers to more easily engage the plunger 600. In other embodiments, grip 604 may be notched or engraved to provide a textured surface, or may be coated in a high-friction material, such as rubber.

Shaft 602 may extend to a terminal portion or cup 608 via a sloped portion 606. In some embodiments, sloped portion 606 may comprise a straight-sided or conical cross-section, while in other embodiments, sloped portion 606 may comprise a curved or negative-hyperbolic cross-section, as shown. In many embodiments, sloped portion 606 may be hollow, and connect to a hollow portion of shaft 602, as discussed above.

Sloped portion 606 may extend to a terminal end or cup 608. In many embodiments, cup 608 may be cylindrical, while in other embodiments, cup 608 may be of other shapes. Cup 608 may include a threaded portion 610 which may comprise one or more turns extending outwardly from the surface of cup 608. In some embodiments, cup 608 may be of sufficient radius to allow threads 610 to meet the inner wall of a vessel in which fluids are to be layered. This may allow a first fluid to flow into the vessel along threads 610 rather than between threads 610 and the inner wall. As discussed above, this may reduce the downward velocity of the first fluid, reducing the chance of mixing with a second fluid in the vessel. Although shown extending downward below threads 610 in FIGS. 10A-10F, in many embodiments, cup 608 may be of shorter length, terminating at or shortly below threads 610.

In some embodiments, a fluid layering device may comprise a reservoir 620. Reservoir 620 may comprise an elongated housing 622 defining an open ended reservoir at one end and an insertable coupling portion 624 at an opposite end. Reservoir 620 may be of any length, with volume dependent on application. In some embodiments, reservoir 620 may be of sufficient length to allow a user to grip housing 622. In one embodiment, housing 622 may be cylindrical, while in other embodiments, housing 622 may be of any other shape. This may provide enhanced grip for a user. For example, as shown, housing 622 may be hexagonal in shape, allowing a user to more easily rotate reservoir 620 to free insertable coupling portion 624 from a vessel.

As with embodiments of fluid layering devices discussed above, reservoir 620 may comprise an insertable coupling portion 624 and annual shoulder 626. When coupling portion 624 is inserted into an open face of an open ended container or vessel, annular shoulder 626 may abut or engage an annular rim of the vessel, preventing the reservoir from being inserted farther into the vessel. Coupling portion 624 may be of sufficient length, in some embodiments, to provide rotational resistance to reservoir 620 when inserted into a vessel, preventing the reservoir 620 from tipping or spilling during operation.

In some embodiments, reservoir 620 may comprise an exhaust port 628 to allow displaced gas or air to escape from a vessel during filling. As discussed above, exhaust port 628 may be sized to control the flow of fluid into a vessel by preventing displaced gas from escaping faster than a predetermined flow rate. However, in this implementation, the rate of at which fluid flows into the vessel also depends on other factors, such as the ratio of the diameter of the piston to the diameter of the vessel.

As discussed above, reservoir 620 may comprise any type or form of material, including engineering grade plastic (PS, ABS, PC), glass, metal, or other material. In some embodiments, reservoir 620 may be translucent, allowing an operator to view the flow of fluid through reservoir 620 into a vessel. In some embodiments, reservoir 620 may be marked with a prep line 630. In operation, after an insertable coupling portion 624 is inserted into a vessel and plunger 600 is lowered to the surface of a fluid within the vessel, in some embodiments, a second fluid may be added to the reservoir to fill the reservoir to the prep line 630, rather than to the top. This may be done to allow a small amount of the second fluid to gently layer on the first fluid, to provide an additional barrier via surface tension against mixing, when the remainder of the second fluid is added.

Referring briefly to FIG. 10B, illustrated is a rear view of the plunger 600 and reservoir 620 of the fluid layering device illustrated in FIG. 10A. As shown, with the exception of threads 610 and some variations of grip 604, in many embodiments, a plunger 600 may be axially symmetric. Likewise, with the exception of exhaust port 628, reservoir 620 may be axially symmetric. However, in other embodiments, multiple exhaust ports 628 may be placed around reservoir 620, increasing flow rate and providing reliability in case a first exhaust port of a plurality of exhaust ports is blocked.

Referring briefly to FIG. 10C, illustrated is a top view of an embodiment of the plunger 600 and reservoir 620 of the fluid layering device illustrated in FIG. 10A. As shown, in some embodiments, plunger 600 may comprise a circular cross-section to mate with the corresponding inner cross-section of a vessel, such as a centrifuge tube. However, in other embodiments, such as where a vessel is square or rectangular, plunger 600 may be similarly square or rectangular, or any other shape to allow a terminal end 608 to be parallel and offset to an inner wall of a vessel in which fluids are to be layered.

As shown, in many embodiments, reservoir 620 may include a housing 622, which may be hexagonal in cross-section, as illustrated. In other embodiments, housing 622 may be square, triangular, circular, or any other shape in cross-section. In some embodiments, housing 622 may not be uniform, but may have a first section, which may be a first shape, such as cylindrical; and a second section, which may be a second shape, such as hexagonal.

In many embodiments, reservoir 620 may comprise an opening 632, which may be of similar shape and size to shaft 602 of plunger 600. In operation, shaft 602 may be inserted through opening 632, allowing plunger 600 to slide up and down along the axis of shaft 602. In some embodiments, opening 632 and shaft 602 may be circular in cross-section, while in other embodiments, opening 632 and shaft 602 may be any other shape, such as square, triangular, hexagonal, etc. In some embodiments, the diameter of shaft 602 may be substantially smaller than the diameter of opening 632, allowing a fluid to flow from the inside of reservoir 620 through opening 632 around shaft 602. In other embodiments, reservoir 620 may have one or more additional openings to allow fluid to flow, and the diameter of shaft 602 and opening 632 may be closer in similarity.

In some embodiments, reservoir 620 may comprise a port 634 to allow displaced gas to escape from beneath reservoir 620 during filling of the vessel. In some embodiments, port 634 may connect to an exhaust port 628, while in other embodiments, port 634 may simply pass through the inner, bottom wall of reservoir 620.

Figure 10D:
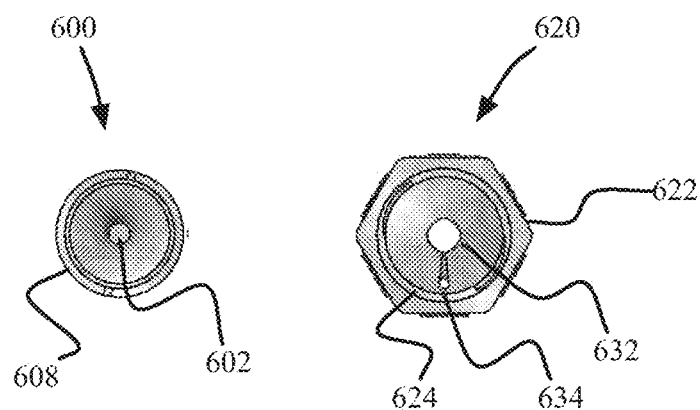

Referring briefly to FIG. 10D, illustrated is a bottom view of an embodiment of the plunger 600 and reservoir 620 of the fluid layering device illustrated in FIG. 10A. As shown, shaft 602 may be hollow, and accordingly may comprise an opening in a sloping portion 606 with a smaller diameter than shaft 602. Insertable coupling portion 624 of reservoir 620 may be cylindrical, as illustrated, to mate with an inner surface of a cylindrical vessel. In other embodiments, coupling portion 624 may be of other shapes to engage an inner surface of a vessel with a non-cylindrical cross section.

Referring briefly to FIG. 10E, illustrated is a side view of an embodiment of the fluid layering device of FIGS. 10A-10D, with plunger 600 inserted through reservoir 620. FIG. 10F illustrates section view A of FIG. 10E, with plunger 600 separated from reservoir 620 for clarity. Referring now to FIG. 10F, in many embodiments, plunger 600 may be hollow and open at a bottom end. As a fluid is poured into a vessel over and around plunger 600, plunger 600 may be buoyed by air or gas within the hollow portion of plunger 600. Accordingly, plunger 600 may automatically rise as fluid is added, maintaining control of flow and layering rate throughout filling.

Still referring to FIG. 10F, in many embodiments, housing 622 of reservoir 620 may define an inner, open-ended fluid reservoir 636. Fluid reservoir 636 may have a conical or sloping lower portion 638, to allow a fluid to flow via gravity to a central hole 632. Although illustrated separate for clarity, in operation, shaft 602 of plunger 600 may be oriented through central hole 632. In some embodiments, fluid may flow through central hole 632 around shaft 602, while in other embodiments, conical portion 638 may include one or more ports 642 through which a fluid may flow from fluid reservoir 636 through conical portion into insertable coupling portion 624 and thus into a vessel. In other embodiments, a port or ports 642 may comprise an exhaust port or ports through conical portion 638, allowing displaced air or gas to be vented from beneath inner reservoir 636 as a fluid flows into a vessel. As discussed above, ports 642 may be sized to regulate flow, with smaller ports reducing flow via back pressure from the displaced gas.

In some embodiments, coupling portion 624 may be threaded or comprise one or more inner threads 640. In one embodiment, threads 640 may be oriented and spaced to engage threads 610 of plunger 600 when plunger 600 is fully raised and rotated. This may allow an operator to lock the plunger 600 into a raised position for insertion and withdrawal from a vessel. In another embodiment, threads 640 may provide further reduction in fluid flow, as a fluid flows down the inner wall of coupling portion 624 and is slowed by threads 640. Although shown as several turns, in some embodiments, threads 640 may comprise one turn, two turns, or any other number of turns. In other embodiments, threads 640 may comprise less than a turn, such as a half turn or quarter turn, or any other length. For example, in one such embodiment, an operator may raise a plunger to engage the threads, and rotate the plunger one half turn to lock the plunger into position.

Figure 10G:
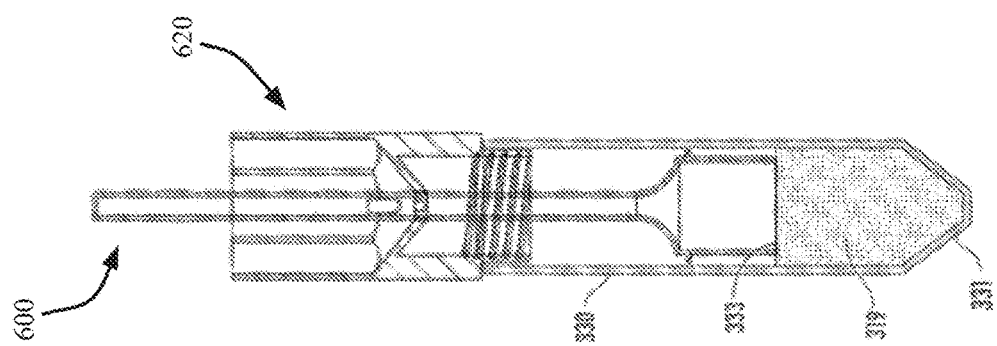
FIGS. 10G and 10H illustrate operation of an embodiment of the fluid layering device of FIGS. 10A-10F in controlling flow of a fluid into an open ended conical container containing a base material.
Figure 10H:
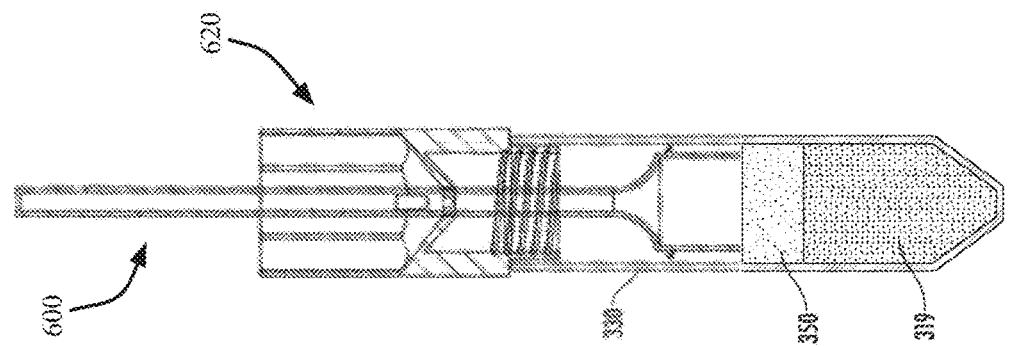

Referring now to FIGS. 10G and 10H, illustrated is an operation of an embodiment of the fluid layering device illustrated in FIGS. 10A-10F. As shown, an upright container 330 may include a base material 319 which may pool along a bottom end 331 of container 330. Insertable coupling portion of reservoir 620 of the device may be inserted into the open end of container 330, and plunger 600 may be lowered until a bottom edge of the cup reaches a surface 333 of the base material 319. In some embodiments, the cup may be lowered to contact surface 333. In many embodiments, the diameter of the cup may be close to the inner diameter of the container 330, and base material 319 may rise through capillary action between the cup and container 330. Accordingly, in other embodiments, the cup may be lowered to just above surface 333. As shown, the shaft of plunger 600 extends above reservoir 620, allowing the operator to grip the shaft to raise or lower the plunger as necessary.

In operation, a fluid 350 may be poured into the open end of reservoir 620 to flow either through a central hole or one or more fluid ports around the shaft of the plunger to fall or run down to the upper surface of a sloping portion of the plunger above the cup via gravity. The fluid 350 may then flow into a channel formed between threads 610 of plunger 600 and the inner surface of the container 330. The fluid 350 may exit the channel and flow down to surface 333, layering above the base material 319 as illustrated.

Advantageously, due to plunger 600, less surface tension between fluid 350 and container 330 is required to control flow of the fluid, as the fluid 350 has less distance to travel after exiting threads 610. Furthermore, as fluid 350 fills container 330, plunger 600 is buoyed upwards, maintaining an approximately constant distance between threads 610 and the surface of fluid 350. Once reservoir 620 is empty, plunger 600 may be raised to engage threads 610 against an inner threaded portion of insertable coupling portion of reservoir 620, and rotated, locking the plunger in place and allowing safe and easy removal of the fluid layering device.

Figure 11C:
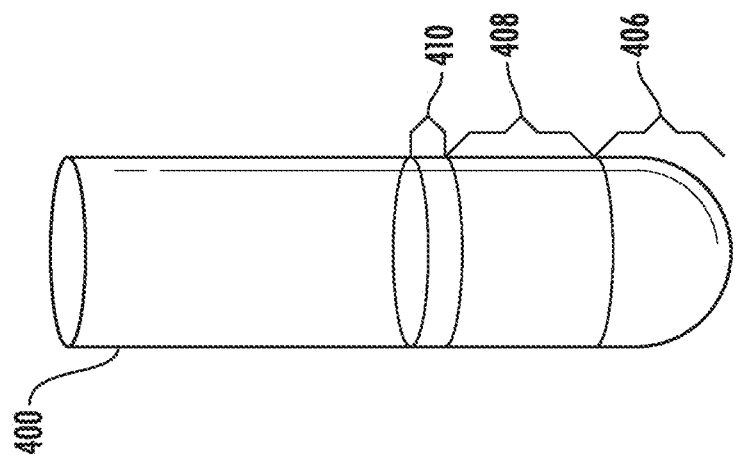
FIG. 11C illustrates the open ended container contents of FIG. 11B after further processing.
Figure 11B:
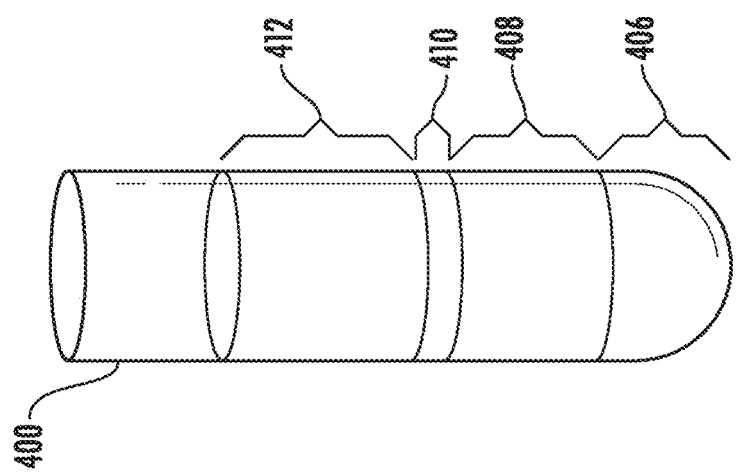
FIG. 11B illustrates contents of the open ended container illustrated in FIG. 11A after applied to a centrifuge process.
Figure 11A:
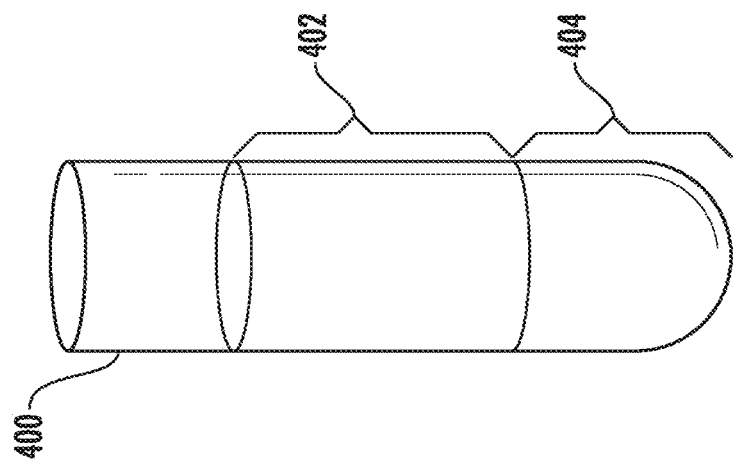
FIG. 11A illustrates an open ended container comprising a base material and a blood sample layered according to one embodiment of the invention.

FIG. 11A illustrates an open ended container 400 comprising a layered arrangement of blood 402 over a density gradient 404, such as Ficoll-paque PLUS. The layered arrangement 402, 404 can be accomplished using any of the devices and processes described herein. The layered arrangement 402, 404 can be centrifuged using standard techniques to separate various blood components. FIG. 11B illustrates contents of the container illustrated in FIG. 11A after applied to a centrifuge process. A bottom layer 406 of granulocytes and erythrocytes is formed along the very bottom of the container 400. Disposed above this layer 406, is a first intermediate layer 408 of density gradient. Above the first intermediate layer 408 is a second intermediate layer 410 of lymphocytes, and above that is a top layer 412 of plasma and platelets. In some embodiments, the top layer 412 can be removed, for example by simply pouring it out of the container as illustrated in FIG. 11C.

Figure 12:
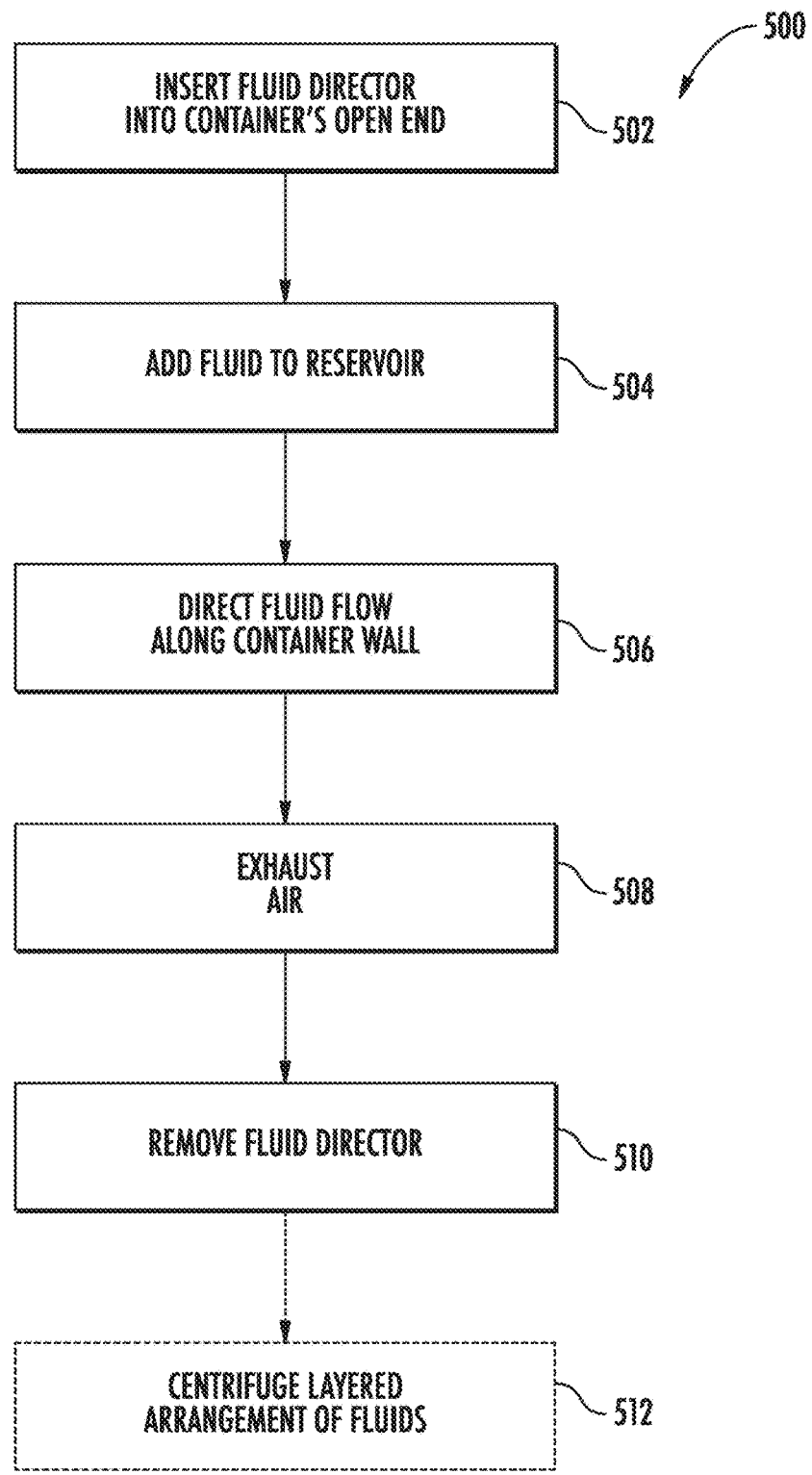
FIG. 12 illustrates an embodiment of a process for directing fluid flow into an open ended container.

FIG. 12 illustrates an embodiment of a process 500 for directing fluid flow into an open ended container. In an initialization step not shown, an open-ended container is partially filled with a base material. This is generally accomplished as part of protocols known to those skilled in the art, such as a protocol for PBMC isolation. The fluid layering device is then coupled to the container from its open end at 502. The coupled arrangement defines a fluid reservoir for temporarily storing a first fluid during the layering process. Also defined are one or more fluid channels providing fluid communication between the reservoir and an interior region of the container in a space or chamber formed between a barrier wall and a surface of the base material. In some embodiments, such as embodiments using a plunger as discussed above, a plunger may be lowered to a surface or just above a surface of a base material.

Next, a fluid is added to the reservoir at 504. The fluid flows under the influence of gravity through the one or more fluid channels into the chamber above the surface of the base material at 506. In particular, in some embodiments, the fluid flow is directed along an inner surface of the container wall, avoiding any free-falling droplets that would otherwise disturb the surface tension of the base material. The sidewall flow continues under the influence of gravity until it reaches the surface of the base material. In other embodiments, such as embodiments using a plunger as discussed above, the fluid may flow down a shaft of the plunger, down a side wall of the container, or may fall freely to an upper surface of a cup of the plunger. The fluid may then flow around the cup, through one or more helical channels formed by ridges of the cup and the container wall under the influence of gravity, avoiding any free-falling droplets from impacting the base material and disturbing its surface tension.

The fluid then begins to pool along the surface. As the volume of fluid increases in the chamber, pressure of any gas within the chamber, such as air is raised. Gas (air) is exhausted from the chamber at 508 by pressure induced by the fluid flow. Exhausted air reduces the pressure and allows for continued fluid flow. Ultimately an equilibrium can be reached between the inflow of fluid and outflow of exhaust gas. The rate of flow can be controlled by at least one of the dimension of the fluid channels (e.g., length, shape, direction, diameter) and dimensions of one or more exhaust vents. In some embodiments using a plunger, as the volume of fluid increases in the chamber, the plunger may be buoyed upward by the fluid, retaining positioning of the cap of the plunger above the surface of the fluid throughout the overlaying process.

The fluid layering device is removed from the chamber at 510. Generally, the device is removed after all of the fluid has flowed from the reservoir into the chamber. In some embodiments, threads of the plunger may be engaged with corresponding threads in the coupling portion of the device. Removal of the device allows for further processing, such as centrifuging at 510 (optional).

Following below are descriptions of a number of features that may be used either alone or in any suitable combination with the devices and techniques described above.

Figure 13B:
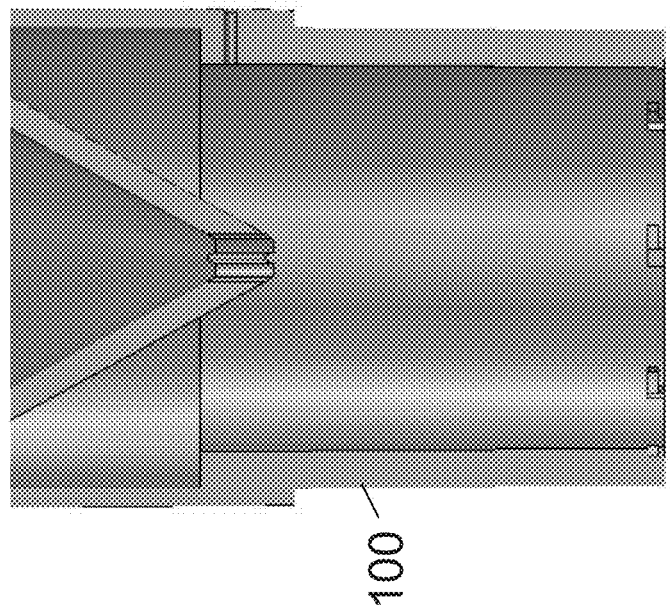
FIG. 13B illustrates a fluid layering device to be used in connection with the plunger of FIG. 13A.
Figure 13A:
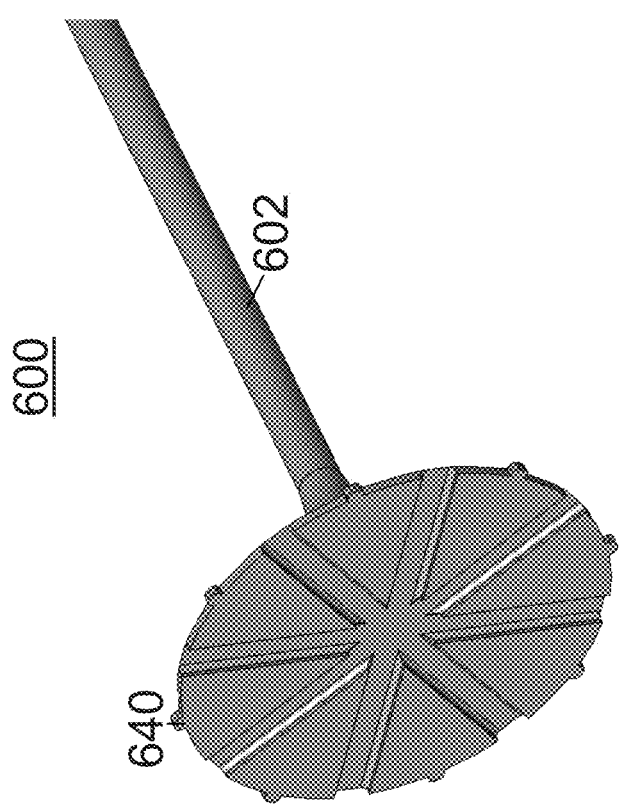
FIG. 13A illustrates an implementation of a plunger.

FIG. 13A depicts another implementation of a plunger 600 to be used in conjunction with fluid layering device 100. The plunger 600 includes teeth 640 which protrude radially from the broadened terminal end of the plunger 600. While the plunger depicted in FIG. 13A includes eight teeth 640, alternative implementations can include fewer more than eight teeth 640. The teeth 640 extend beyond the edge of the broadened terminal end of the plunger 600, such that the radius of the broadened terminal end including the teeth exceeds the radius of the bottom end of the fluid layering device 100, also shown in FIG. 13B. Located along the bottom portion of the fluid layering device 100 are several notches 150. Each notch 150 is an L-shaped gap which extends upward into the device 100 and corresponds to a tooth 640. When the plunger 600 is inserted into the device 100, the teeth 640 can be aligned with the notches 150. The plunger 600 can then be pulled up into the device 100 so that the teeth 640 pass through the notches 150. Rotating the device about the elongated shaft 602 will cause the teeth 640 to lock into the notches 150, and the plunger 600 can remain securely in place when released. To lower the plunger 600 back out of the device 100, the plunger can again be rotated about the elongated shaft 600, allowing the teeth 640 to pass through the notches 150.

Figure 14B:
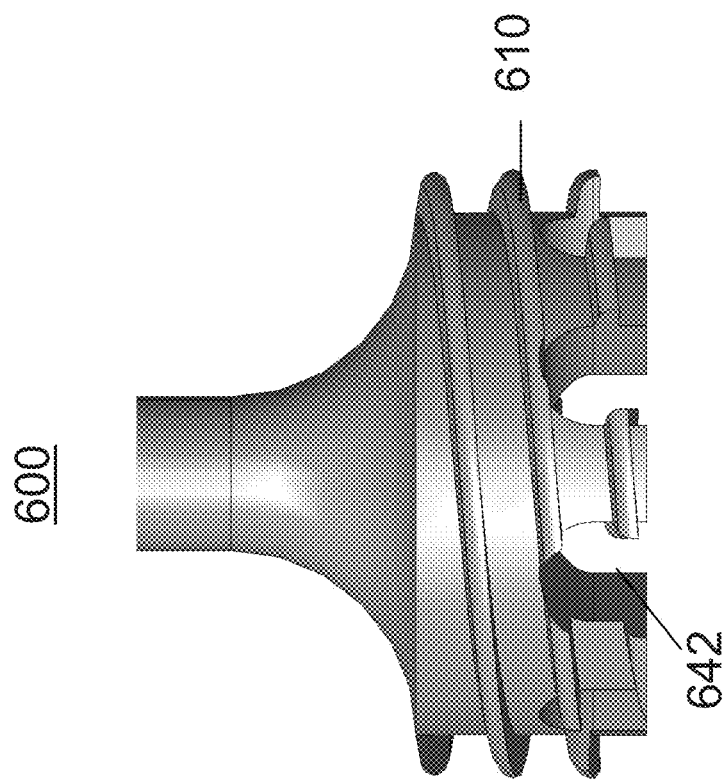
FIG. 14A-14B illustrate various views of the terminal end of a plunger.
Figure 14A:
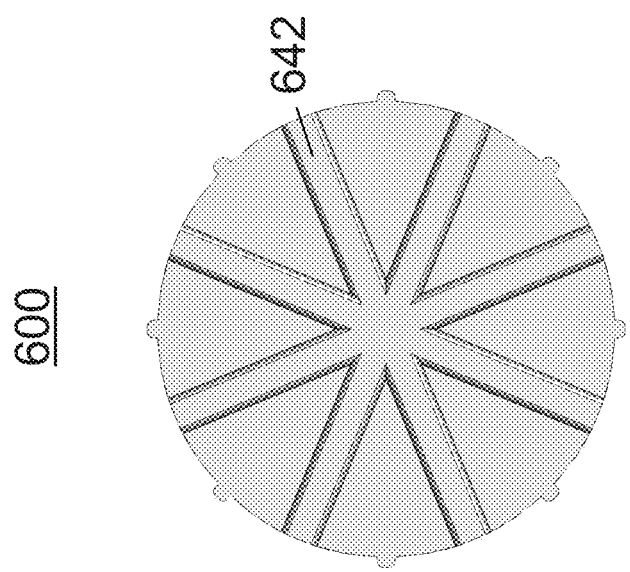

Referring now to FIG. 14A, a bottom view of the plunger 600 is shown. The bottom surface of the broadened terminal end of the plunger 600 includes channels 642. The channels 642 extend through the entire bottom surface of the terminal end of the plunger 600, including through the threaded portion 610. FIG. 14B shows a side view of the terminal end of plunger 600 including the channels 642. As described above, the plunger 600 can be inserted into a fluid layering device and gravity can drive the flow of fluid down the plunger 600 toward the broadened terminal end. Fluid will continue to flow downward along the threads of the threaded portion 610. As depicted in FIG. 14B, the channel 642 creates a gap in the threaded portion 610 of the plunger 600. As the fluid traveling down the threads reaches channels 642, a portion of the fluid will travel inward toward the center of the terminal end of plunger 600 through the channels 642, and will finally travel down the walls of the channels 642 to be deposited into the fluid layering device. Thus, the channels 642 can help to slow the speed of the fluid as it is deposited into the fluid layering device, which can reduce the likelihood that the fluid will mix unacceptably in the device. In this implementation, eight channels 642 are shown with rounded cross-sections. However, in other examples, a different number of channels may be used, and the channels may have a different shape.

Figure 15B:
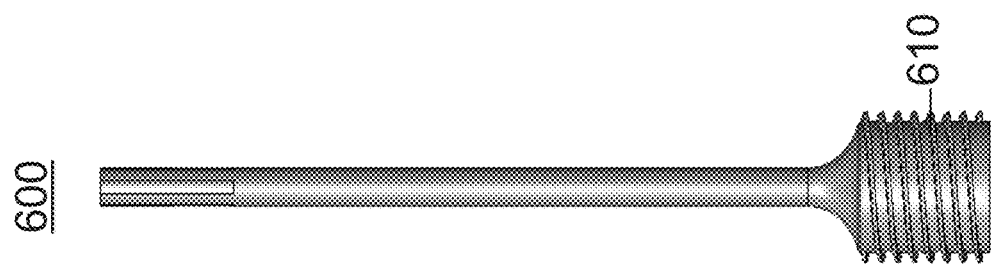
FIG. 15B-15C illustrate an implementation of a plunger to be used in connection with the fluid layering device of FIG. 15A.
Figure 15A:
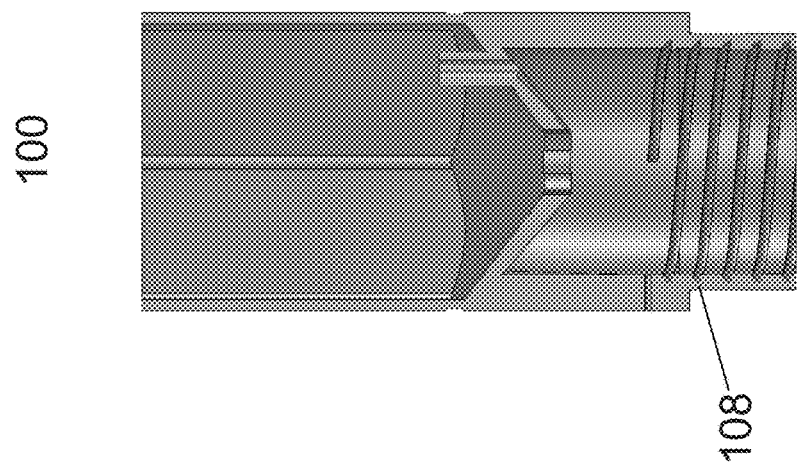
FIG. 15A illustrates an implementation of a fluid layering device.
Figure 15C:
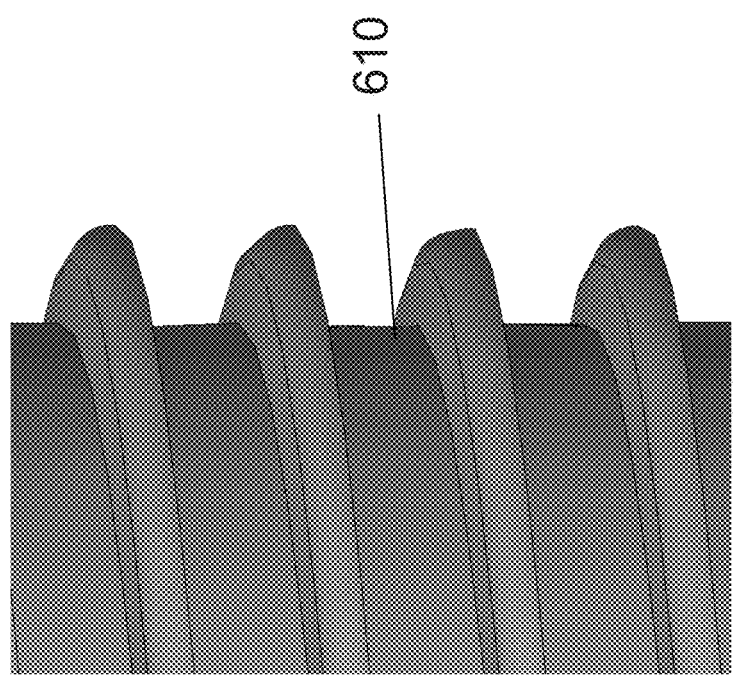

FIG. 15A depicts an implementation of the fluid layering device 100. The device can include helical channels 108, which allow fluid to flow downward into a container. FIG. 15B shows the plunger 600, which includes a threaded portion 610. The threaded portion 610 can be used to slow the flow of sample fluid, as discussed above. The threaded portion 610 can also interact with the helical grooves 108 for temporary storage of the device. FIG. 15C is an enlarged view of the threaded portion 610 of the plunger 600. As shown in the figure, the bottom surface of the threads can have a flat shape in order to maximize the surface area in contact with the helical grooves 108 in order to increase friction so that the plunger 600 will remain secure during storage.

Figure 16B:
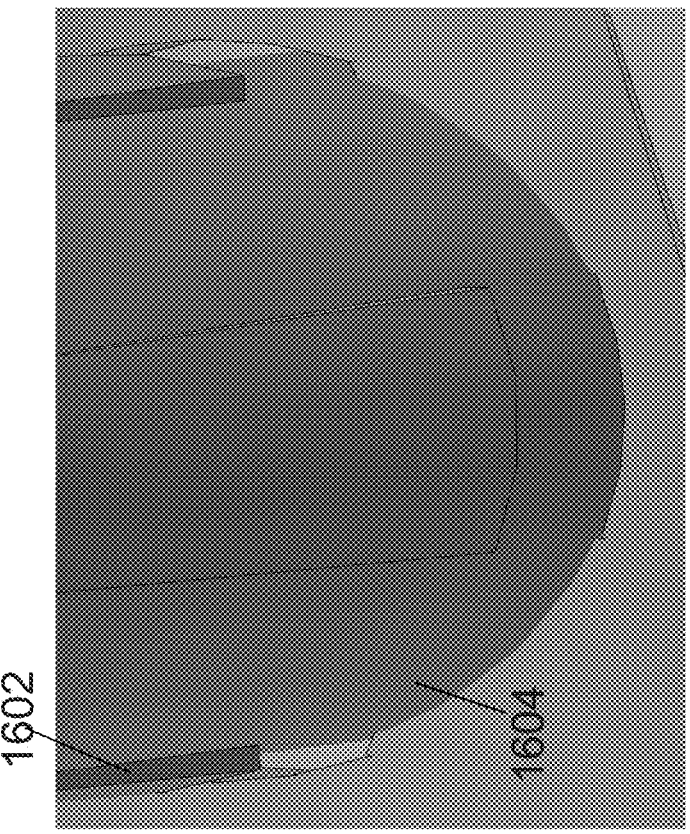
FIG. 16A-16B illustrate an implementation of a plunger and an implementation of a fluid layering device.
Figure 16A:
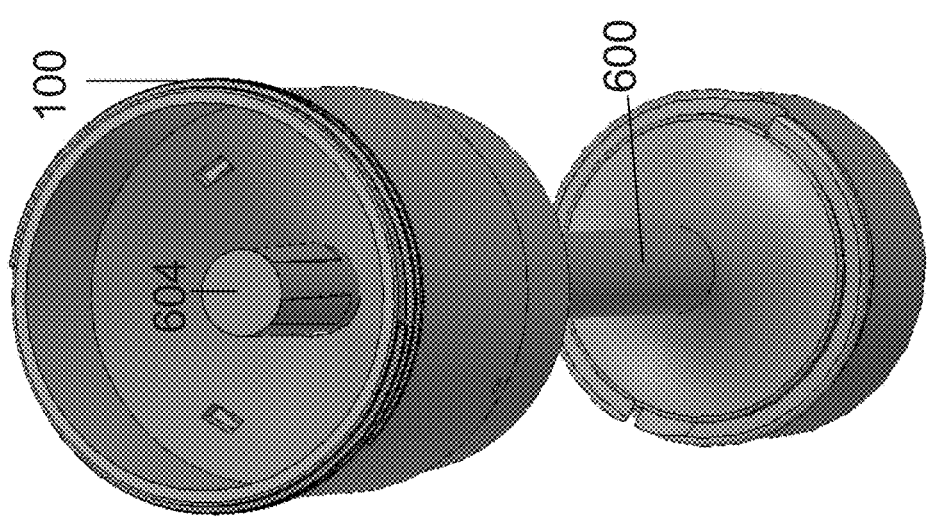

FIG. 16A depicts the plunger 600 inserted through the fluid layering device 100. The grip 604 of the plunger 600 is shown within the reservoir of the device 100. FIG. 16B is an enlarged view of the grip 604. As show in FIG. 16B, the edge 1602 of the grip 604 extends slightly beyond the edge 1604 of the opening of the device 100. The larger diameter of the grip 604 due to the protruding edge 1602 prevents the plunger 600 from falling through the device 100.

FIG. 17A depicts a cross section of an implementation of the fluid layering device 100 which includes ports 1702. When the height of the sample fluid in the device 100 is above the top of the ports 1702, the ports 1702 can carry sample fluid down towards the conical section of the device 100. The ports 1702 can also act as ventilators. For example, when the height of the sample fluid is below the top of the ports 1702, and air is displaced as the fluid is layered into a container, the ports 1702 can provide an outlet for the air to escape. This reduces pressure in the container where the fluid is collected.

FIG. 17B is an enlarged cross sectional view of another implementation of the device 100 shown in FIG. 17A. A scoop guide 1704 can provide a partial channel through which sample fluid can flow towards the opening at the bottom of the device 100. Because the port 1702 is located near the edge of the device 100, it is possible that some of the fluid will travel down the outside edge of the device 100 after leaving the port 1702. Scoop guide 1704 helps to reduce the amount of fluid traveling down the outside edge of the device 100 by redirecting fluid towards the central opening in the device 100. This is beneficial in implementations in which the device 100 includes a plunger at the central opening, because more of the sample fluid can be directed towards the plunger.

FIG. 18 depicts an implementation of the fluid layering device 100. The bottom portion of the device includes a conical section having an upper edge 1802 and a lower edge 1804. The diameter of the upper edge 1802 is greater than the diameter of the lower edge 1804. When the device 100 is inserted into a conical container, a seal is created between the conical container and the conical section of the device 100. In some implementations, the ratio of the diameters of the conical section at the upper edge 1802 and the lower edge 1804 is selected such that the walls of the conical section have the same slope as the walls of the conical container.

Figure 19C:
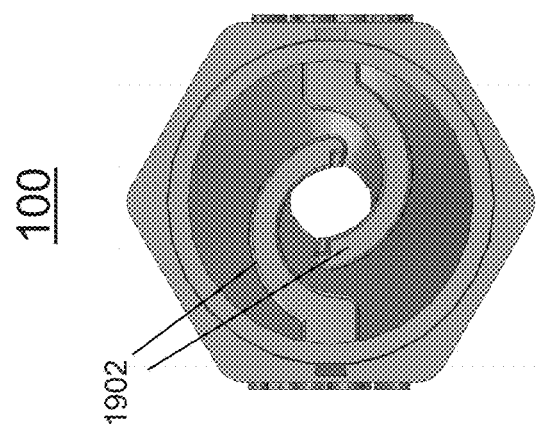
FIG. 19A-C illustrate yet another implementation of a fluid layering device.
Figure 19B:
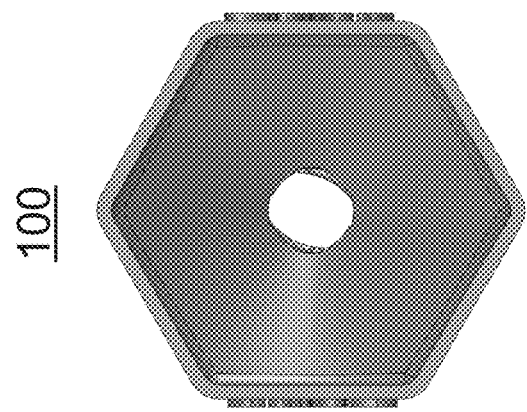
Figure 19A:
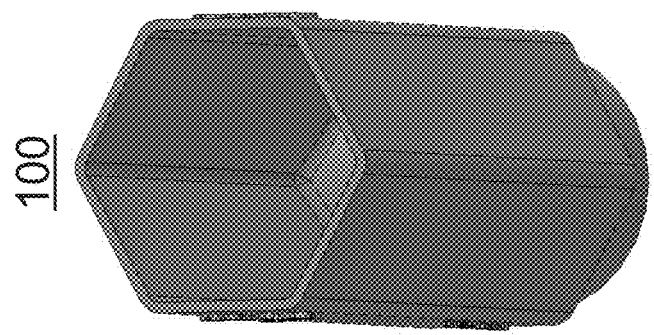

FIG. 19A-19C depict an isometric view, a top view, and a bottom view, respectively, of the fluid layering device 100. As shown, the device 100 can have a hexagonal cross sectional shape, which may provide a better grip for inserting or removing the device 100 from a container. In various embodiments, other suitable shapes may be used. e.g., other polygonal shapes. FIG. 19B shows a reservoir in the device 100 having conical walls that slope down to a central opening through which a plunger can be inserted. FIG. 19C shows two hooks 1902 located at the bottom of the device 100. The hooks curve around the central opening through which a plunger may be inserted, and can help to hold or stabilize the plunger during use.

FIG. 20A depicts a bottom portion of the device 100. The bottom portion includes a circular housing 2000 with two hooks 1902 extending from the sides of the housing 2000 towards its center. At the end of each hook is a foot 2002. The housing 2000 includes n-shaped cutouts 2004 surrounding the portion of the housing 2000 which connects to the hooks 1902. On the outside edge of the housing 2000 and surrounded by the n-shaped cutouts 2006 are tabs 2006. The n-shaped cutouts 2004 allow a portion of the housing 2000 to flex inward when force is applied to the tabs 2006. As shown in FIG. 20B, the plunger 600 can be inserted through the center of the housing 2000 when the tabs 2006 are pressed inwards. Releasing the tabs 2006 causes the plunger 600 to be held in place by the hooks 1902 and the feet 2002. The feet 2004 provide increased surface area, increasing the friction on the plunger 600 to hold it more securely in place. In other implementations, the hooks 1902 do not include feet 2002, and the plunger 600 is held in place only by contact with the hooks 1902. The plunger 600 can be withdrawn from the device by pulling it upwards though the circular housing 2000 while pressure is applied to the tabs 2006.

Figure 21A:
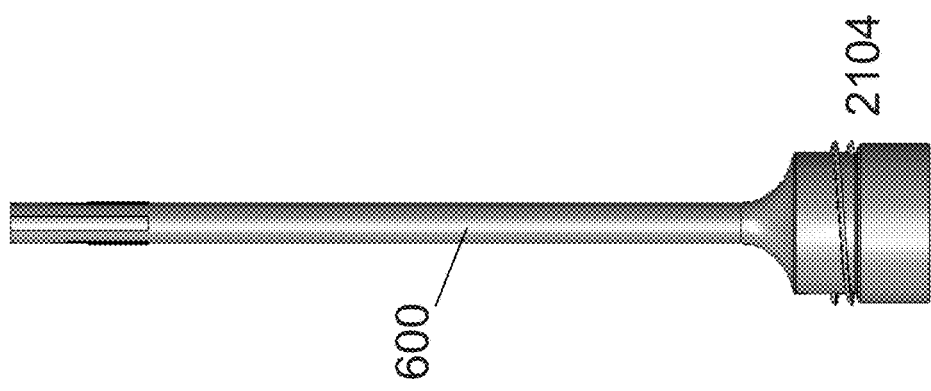
FIG. 21A-21B illustrate an implementation of a plunger.
Figure 21B:
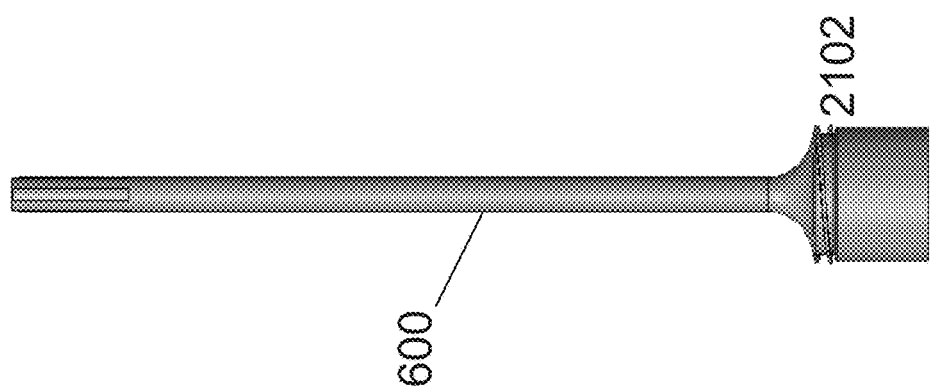

FIG. 21A depicts an implementation of the plunger 600. The plunger 600 includes a broad terminal end with threads, as discussed above. The plunger 600 also includes a shoulder 2102. The shoulder 2102 increases the diameter of the bottom portion of the plunger 600, which limits the space between the plunger 600 and a conical tube used for fluid layering. This limits the amount of sample fluid, which provides a slower and more controlled layering process. In the example shown in FIG. 21A, the diameter of the shoulder 2102 is approximately equal to the diameter of the plunger 600 plus the width of the threads, however any other diameter could also be used. The height of the shoulder 2102 can also vary. For example, FIG. 21B depicts a shoulder 2102 that begins halfway down the broad terminal end of the plunger 600.

FIG. 22A depicts another implementation of the plunger 600. The diameter of the plunger 600 at point 2202 is larger than the diameter at point 2204, to allow for a more controlled fluid layering process. For example, as depicted in FIG. 22B, the plunger 600 is inserted through an opening the device 100 and fluid is layered in the container 330. The greatest risk of mixing fluids occurs at the beginning of the fluid overlay process. Initially the level of fluid in the container 330 is relatively low, so the larger point 2202 of the plunger 600 is surrounded by the opening in the device 100. Because of the greater diameter of the plunger 600 at point 2202, there is a narrow gap between the device 100 and the plunger 600 at the beginning of the overlay process. This limits the amount of sample fluid that can flow through the gap and onto the plunger 600, which results in a slower layering process. As the process continues and the container 330 fills with sample fluid, the plunger 600 is pushed higher so that the point 2204 is surrounded by the opening in the device 100. The smaller diameter of the plunger 600 at point 2204 allows more sample fluid to flow onto the plunger 600, which results in a faster overlay process after the layers have been established.

Also depicted in FIG. 22A is a flat portion 2206. Because the bottom portion of the plunger 600 is round, it can come into contact with the walls of the container 330 and form a seal. The flat portion 2206 allows fluid to continue flowing into the container 330 even if such a seal is formed. In some implementations, the diameter of the broad end of the plunger 600 at the point 2208 is greater than the diameter at point 2210. The ratio of the diameters at points 2208 and 2210 can be selected so that the broad end of the plunger 600 has a slope that is substantially the same as the slope of the conical walls of container 330. This can allow the plunger 600 to reach further down into the container 330 during the layering process. FIG. 22C shows a pattern 2212 etched into or deposited on the flat part 2206 of the plunger 600. The pattern can create additional resistance to the motion of the sample fluid as it flows down the plunger. This further slows the fluid and allows for a more controlled layering process. The pattern 2212 shown in FIG. 22C is exemplary only, and any other pattern could be used instead. In other implementations, a similar pattern is used on other portions of the plunger 600, such as the elongated shaft or other areas of the broad terminal end.

Figure 23B:
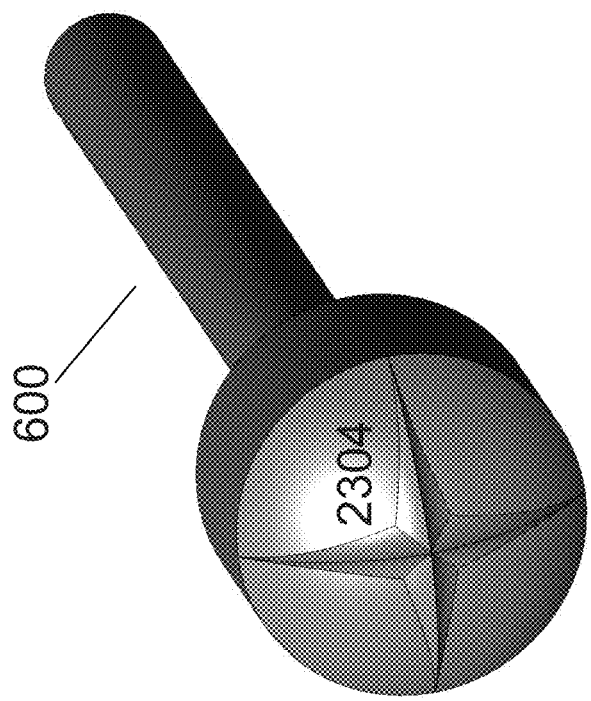
FIG. 23A-23B illustrate a third implementation of a plunger.
Figure 23A:
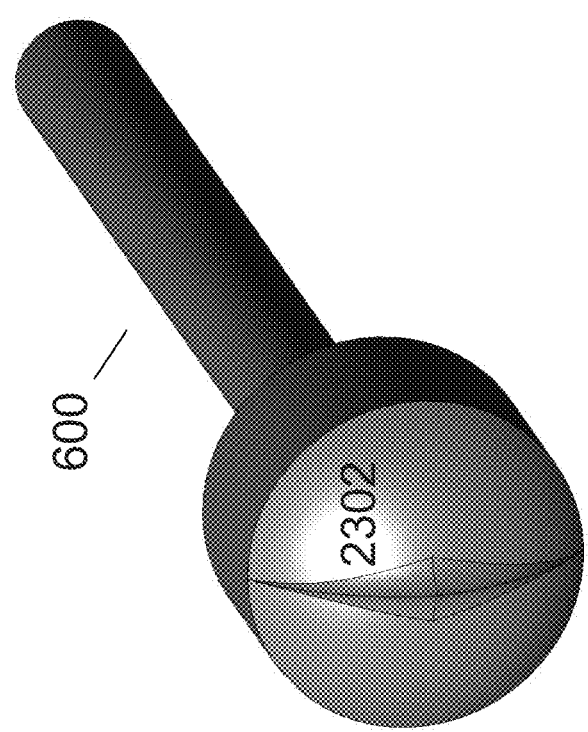

FIG. 23A depicts a bottom view of an implementation of the plunger 600. The bottom of the plunger has a domed surface with a beveled area 2302. The beveled area 2302 increases the surface area of the bottom of the plunger 600, which displaces a greater amount of fluid and increases the buoyancy of the plunger 600. FIG. 23B depicts a plunger 600 with a double beveled area 2304. Other geometries can also be used to increase the surface area of the bottom of the plunger to increase its buoyancy.

FIG. 24 depicts a bottom view of another implementation of the plunger 600. The bottom of the plunger 600 can include a central cylindrical member 2402. Extending radially outward from the cylindrical member 2402 are 4 curved plates 2404. As shown in FIG. 24, the height of the curved plates 2404 can vary in the direction of the axis of the cylindrical member 2402. The curved plates 2404 are designed to slow the flow of sample fluid, resulting in a more controlled layering process.

Figure 25C:
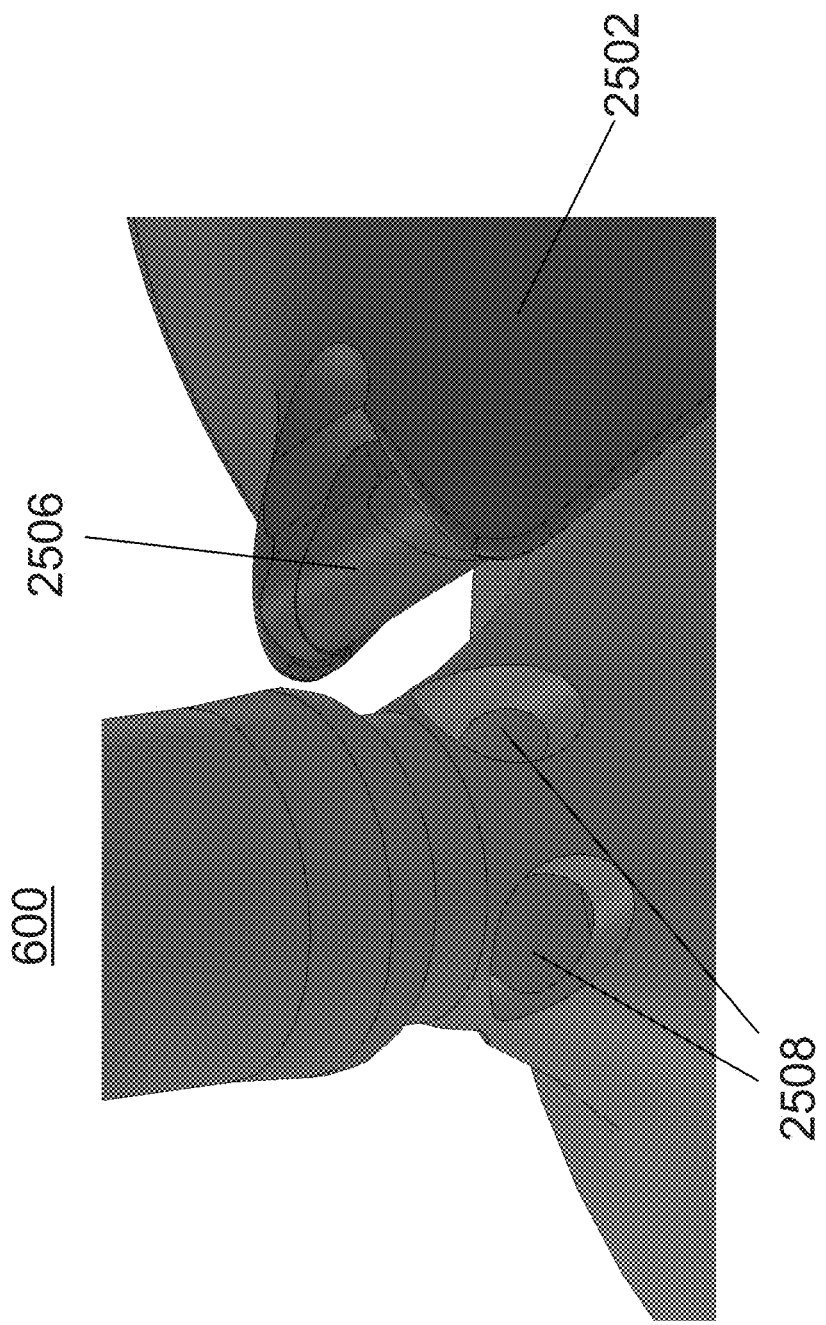

FIG. 25A depicts an implementation of the plunger 600 which includes two shell members 2502. Each shell 2502 has the shape of half of the surface of the broadened terminal end of the plunger 600. FIG. 25B shows a cross sectional view of the plunger 600 with shells 2502. As shown, the shells are attached to the plunger with hinges 2504. FIG. 25C is an enlarged view of the hinge area of the shell 2502 and the openings 2508 through which the hinges 2504 are inserted. The hinge of shell 2502 includes a groove 2506. The groove 2506 can be angled, as shown in FIG. 25C, allowing the shell 2502 to flare outward as shown in FIG. 25A.

In some instances, conical containers of various sizes may be used for layering fluids. The shells 2502 allow can maintain contact with the inner surfaces of a larger container. If the diameter of the container varies, the shells 2502 can self-adjust according to the normal force applied by the inner walls of the container. This allows the shells 2502 and plunger 600 to maintain contact with the surfaces of containers of different sizes and/or shapes, which results in increased stability and a smoother layering process.

Sample fluid can travel down the shaft of the plunger 600 and along the outer surface of the shells 2502. Some of the fluid may also travel down the broadened terminal end of the plunger 600. In some implementations, the shells may have features described herein in connection with the broadened terminal end of the plunger, such as the shoulder depicted in FIG. 21A-21B, the flat portion shown in FIG. 22A, and the pattern shown in FIG. 22C.

Figure 25E:
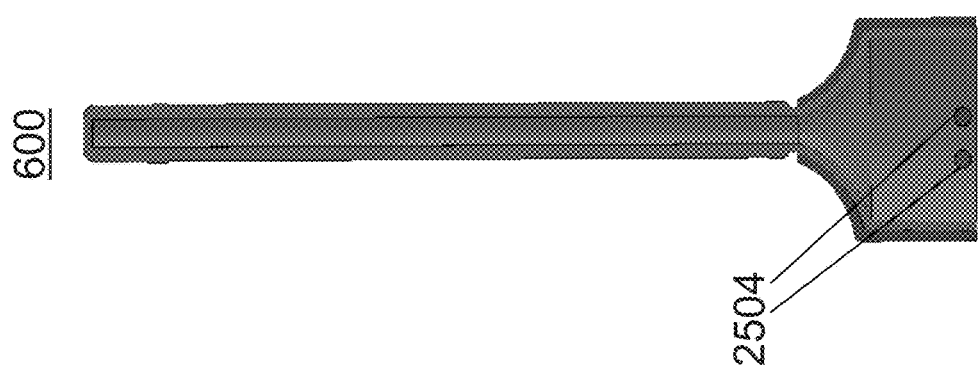
Figure 25D:
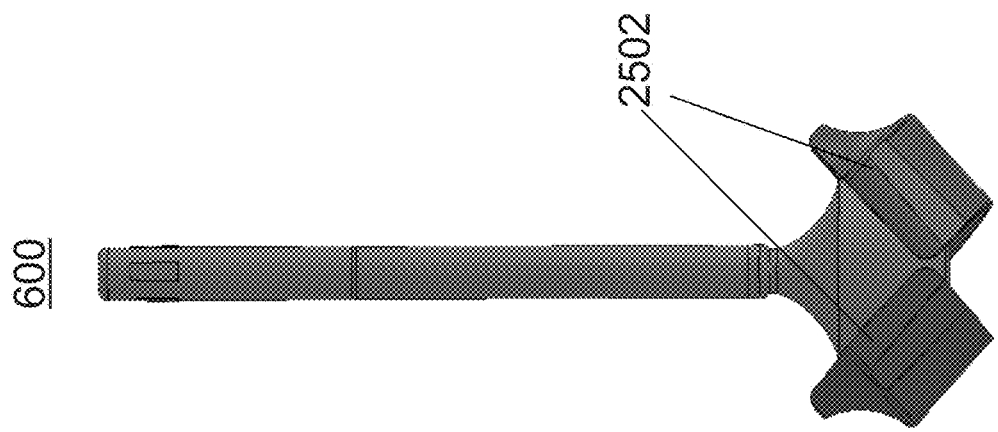

FIGS. 25D-25E show an alternative implementation of the plunger 600 and shells 2502. The hinges 2504 are located at the bottom of the terminal end of the plunger 600. The location of the hinges 2504 and the mass distribution of the shells 2502 can be selected such that the shells 2502 expand outwards under their own weight when at rest, as shown in FIG. 25D. Again, the shells 2502 can make contact with the inner edges of a conical container and can expand or contract in order to accommodate containers of various sizes. In some implementations, the shells 2502 can have any of the advantageous features of the broadened terminal end of the plunger 600, as described above. Sample fluid can travel down the plunger 600 and can then travel over the shells 2502 or over the terminal end of the plunger 600 as part of the fluid layering process.

Figure 26B:
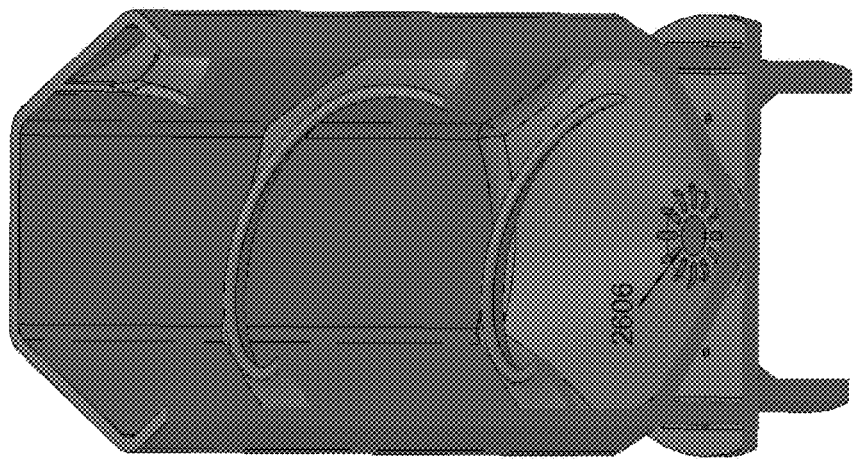
FIG. 26B illustrates a cross sectional view of the fluid layering device shown in FIG. 26A.
Figure 26A:
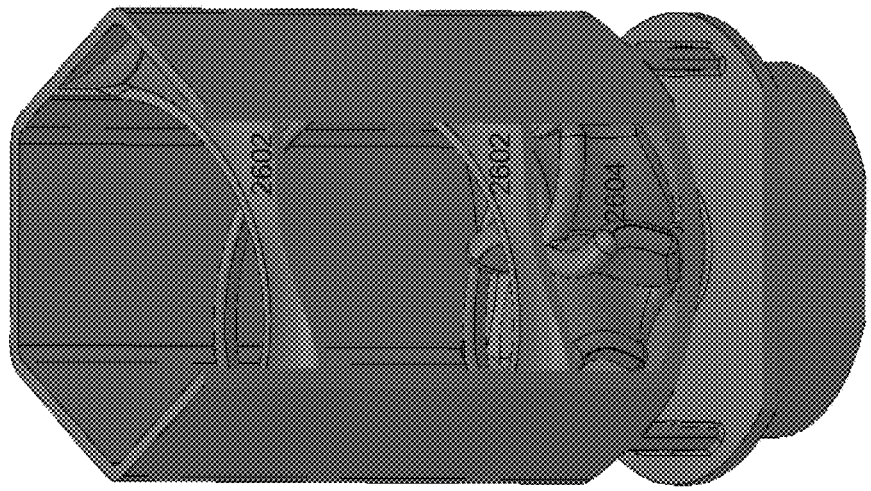
FIG. 26A illustrates a fluid layering device and a turbine.
Figure 26C:
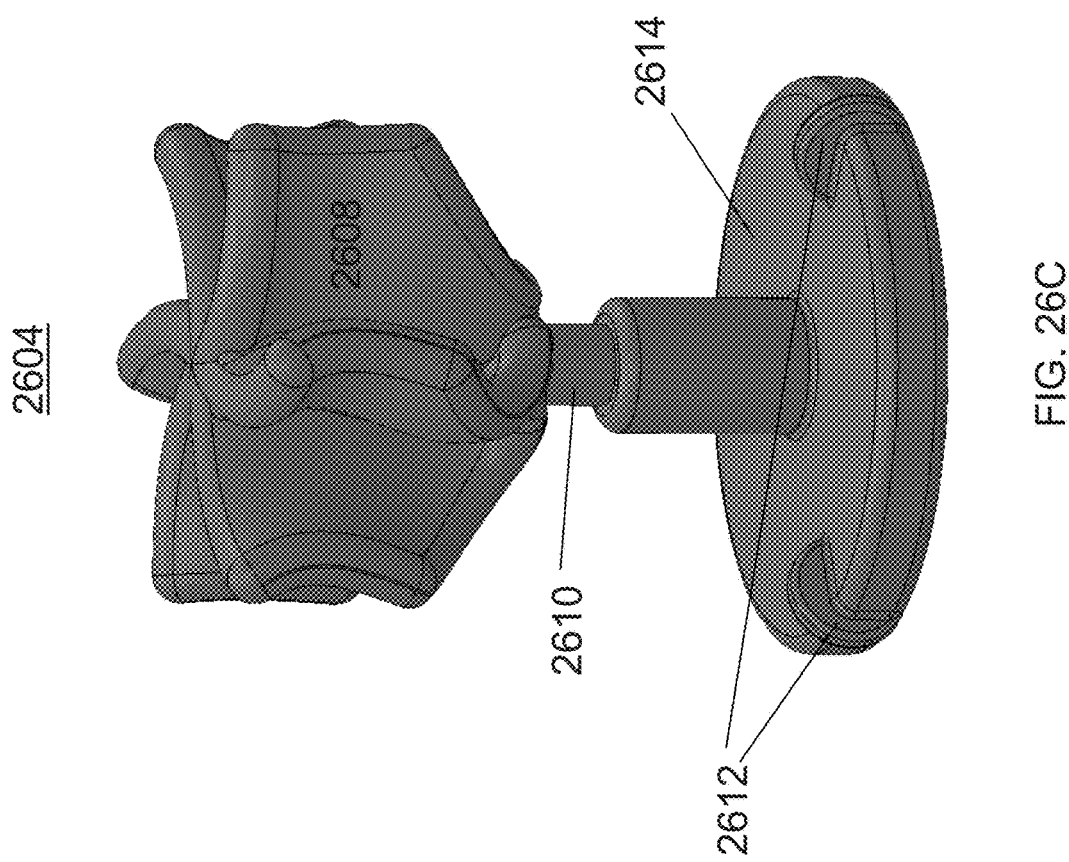
FIG. 26C illustrates a detailed view of the turbine shown in FIG. 26A.

FIG. 26A shows an implementation fluid layering device 100. The device includes a helical member 2602 on the inside edge of the device 100, and a turbine 2604 located at the bottom portion of the device 100. FIG. 26B shows a cross-section of the device 100 without the turbine 2604. As shown, the device 100 can include a drain 2606 to allow sample fluid to pass thought the device 100. FIG. 26C is an enlarged view of the turbine 2604. The turbine 2604 includes six curved blades 2608, and central shaft 2610, and raised features 2612 protruding from a base 2614. Although six blades 2608 are depicted in FIG. 26C, any other number of blades could be used in other implementations. The shape of the blades can also vary. Similarly, the turbine 2604 can include any number of raised features 2612, which can also have varied shapes.

Fluid can be introduced into the device 100 at the top of the helical member 2602. Gravity will drive the fluid downwards along the helical member 2602. The fluid gains momentum as it travels along the helical member 2602. When the fluid reaches the bottom of the device 100, it turns the blades 2608 of the turbine 2602, causing the base 2614 of the turbine 2604 to rotate. The fluid then travels down the blades 2608 and shaft 2610 under the force of gravity, and contacts the rotating plate 2614. As the plate 2614 rotates, the fluid travels towards its outer edge, where it collides with the raised features 2612. The collision causes the fluid to be distributed evenly over the bottom conical portion of the device 100, and gravity continues to move the fluid downward through the drain 2606. The even distribution of the fluid in the device 100 results in a smooth layering process as the fluid exits the device 100 through the drain 2606.

Figure 27A:
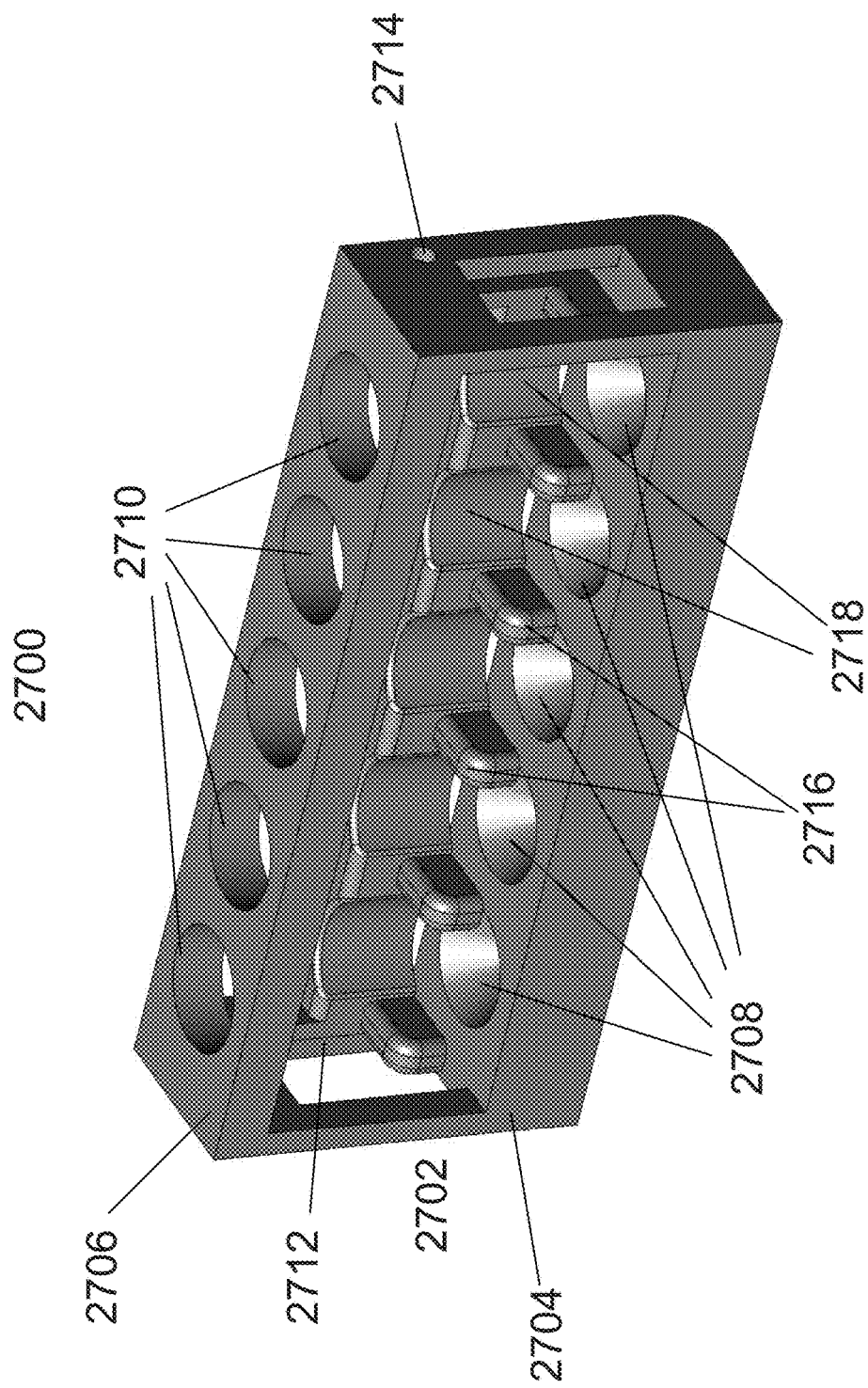
FIG. 27A-B illustrate a rack used for stabilizing or storing containers for a fluid layering process.

FIG. 27A depicts a rack 2700 that can be used to stabilize five containers to be used for fluid layering. The rack 2700 includes a primary member 2702 having a rectangular base 2704 and a ceiling 2706. The base includes five indentations 2708, each of which can support a container to be used in a fluid layering process. The indentations 2708 can be designed to match the shape of the containers (e.g., the indentations 2708 can be conical if conical containers are to be used). The ceiling includes five openings 2710, each aligned with a corresponding indentation 2708. The openings 2710 allow the containers to be inserted into the indentations 2708 and also provide support for the containers. The rack 2700 also includes a support member 2712. The support member 2712 attaches to the primary member 2700 via hinges 2714 and includes feet 2716 and arches 2718. Each arch 2718 has a corresponding indentation 2708 and opening 2710. Although the rack 2700 shown in FIG. 27A holds five containers, the rack 2700 could be designed to hold any number of containers (e.g. by increasing or decreasing the number of indentations 2708, openings 2710, and arches 2718 to accommodate the desired number of containers).

Figure 27B:
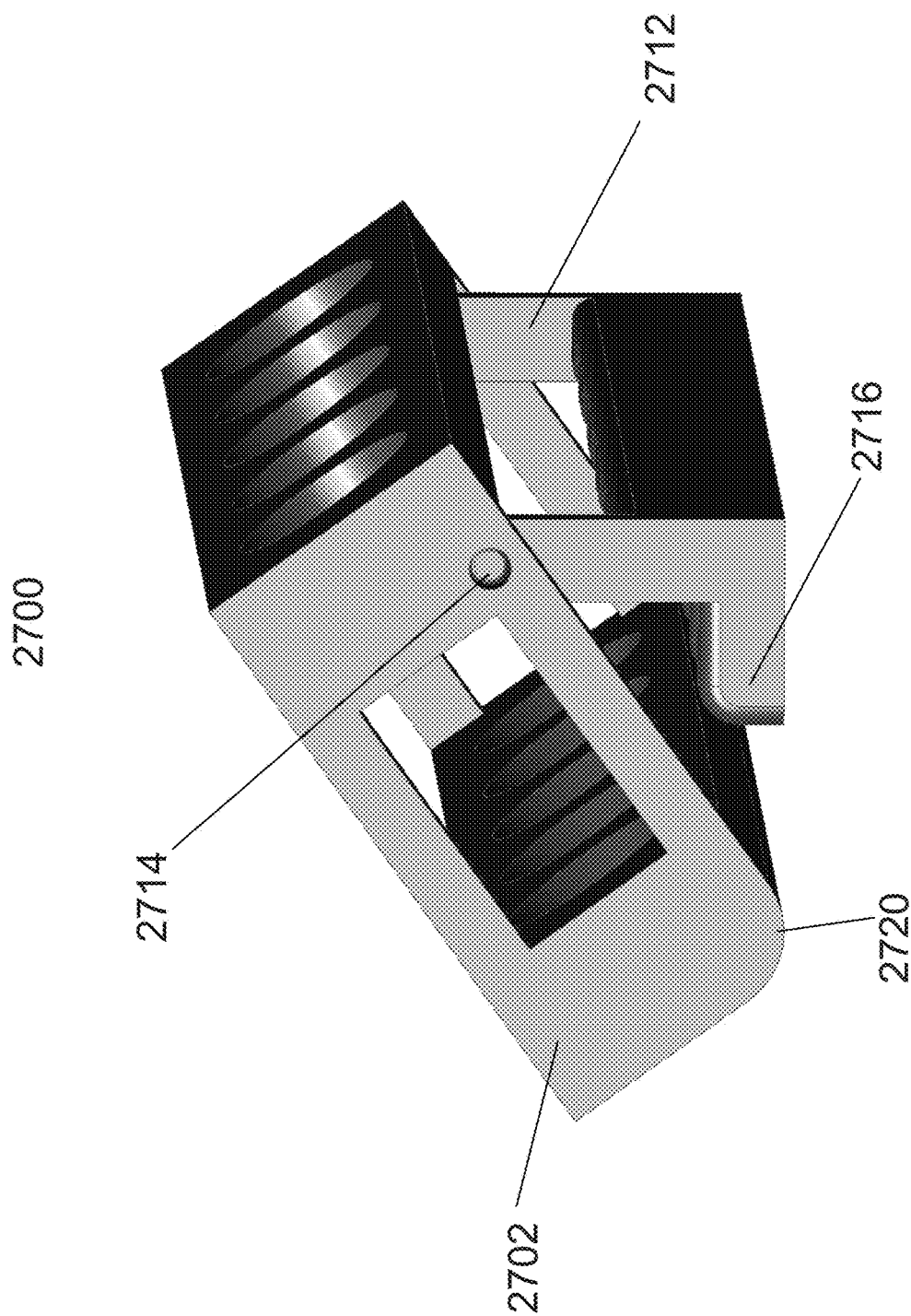

FIG. 27B depicts a second view of the rack 2700. As shown, the hinges 2714 of the support member 2712 are rotated about 45 degrees with respect to the primary member 2702. The rack is supported on a flat surface by the feet 2716 and a curved edge 2720 of the primary member 2702. This configuration can be helpful to a technician performing a fluid layering process because it allows the containers to be held at angle.

Figure 28B:
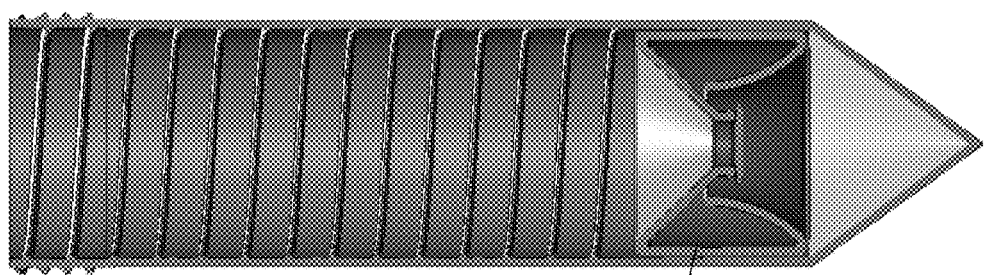
FIG. 28B illustrates a cross sectional view of the trap insert of FIG. 28A installed in a container.
Figure 28A:
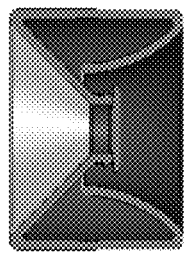
FIG. 28A illustrates a trap insert for a container to be used in a fluid layering process.

FIG. 28A depicts a cross sectional view of a trap insert 2800 for use in a fluid layering process. The trap insert 2800 can be inserted into a conical container or manufactured as part of the conical container. As shown in FIG. 28B, the trap insert is located near the bottom end of the container when inserted.

Figure 28C:
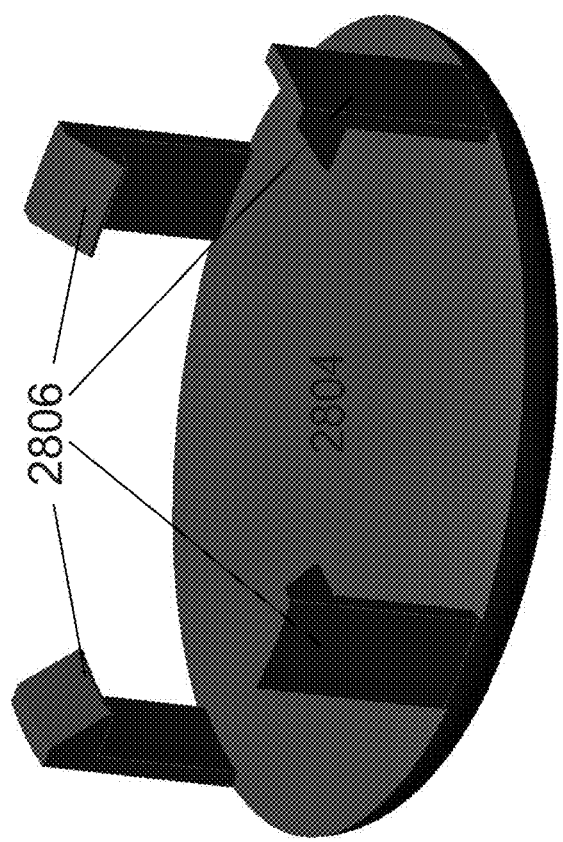
FIG. 28C illustrates a cap used in connection with the trap insert of FIG. 28A.

FIG. 28C depicts a cap 2802 that can be used in conjunction with the trap insert 2800. The cap 2802 includes a flat circular member 2804 and hooks 2806 extending upwards from the edges of the circular member 2804. Although four hooks 2806 are shown in FIG. 28C, the cap 2802 may include any number of hooks 2806 in other implementations.

FIG. 28D is an enlarged cross sectional view of the trap insert 2800 shown in FIG. 28A, shown with the cap 2802 installed. The trap 2800 includes a conical opening 2808, a lip 2810, a reservoir 2812 defined by a partial wall 2814, and an exit chamber 2816. The exit chamber 2816 leads to the bottom of the container into which the trap 2800 is inserted. When the cap 2802 is installed, the hooks 2804 interact with the lip 2810 to limit the downward motion of the cap 2802. Initially, the density layer is deposited into the container by passing it through the conical opening 2808. The weight of the fluid depresses the cap and fluid exits through the exit chamber 2816, filling the container. As the fluid level increases, the fluid rises over the edge 2814 and fills the chamber 2812 and part of the conical opening 2808. Pressure from the added fluid will case the cap 2802 to rise and seal off the potion of the container below the cap from the aboble. The sample fluid can then be added to create the second layer. Mixing between the sample fluid and the first layer will be limited dure to the physical barrier formed when the cap seals off the bottom potion of the container that holds the majority of the fluid of the first layer.

In some embodiments, the second layer may be added using any suitable technique, e.g., any of those described herein. For example, in some embodiments, the inner surface of the open ended container may include spiral notches uses to control the speed of the flow of fluid forming the second later as it is added on top of the first layer.

In some implementations, the sample fluid is blood. When the sample fluid has been added and two layers have been created, a centrifuge process may be used to separate the fluid into its various components. For example, the centrifuge process will result in red blood cells at the bottom of the container and within the reservoir 2812 and the exit chamber 2818. Above the red blood cells (i.e. above the conical opening 2808) will be the density layer, followed by white blood cells, followed by plasma. The container may then be turned upside down and the plasma and white blood cells can be poured out of the tube. When the container is turn upside down for pouring, the cap will move towards the conical opening 2808, creating a seal and preventing red blood cells from escaping. Pressure created by the fluid (i.e. red blood cells) in the reservoir 2812 also helps to prevent the red blood cells from exiting through the conical opening 2808 while the plasma and white blood cells are poured out.

Figure 29B:
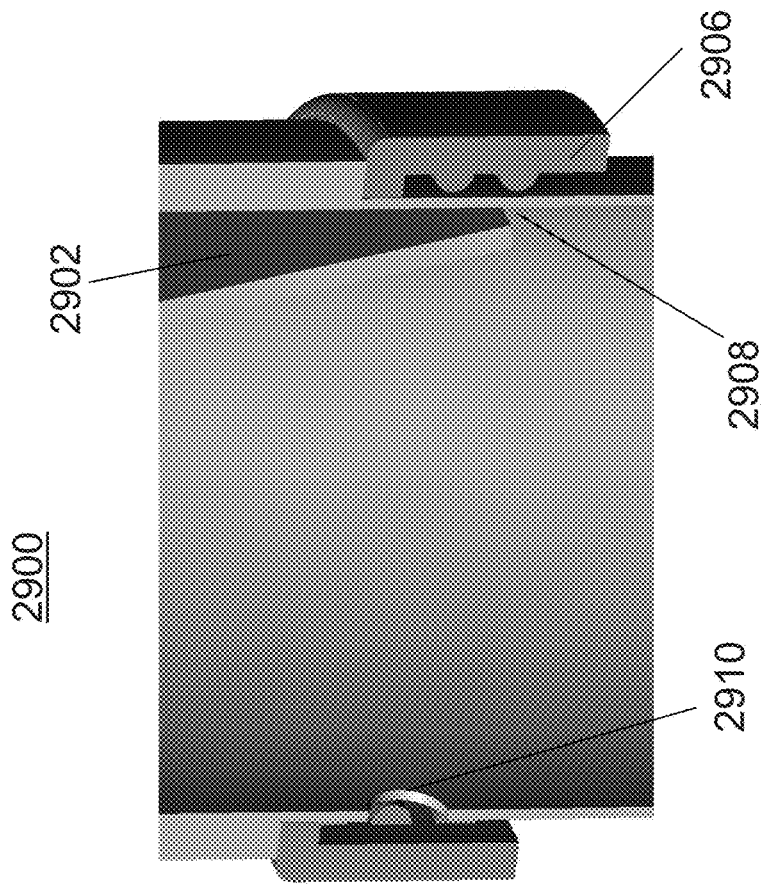
FIG. 29A-C illustrate a partitioned cylinder for use in a fluid layering process.
Figure 29A:
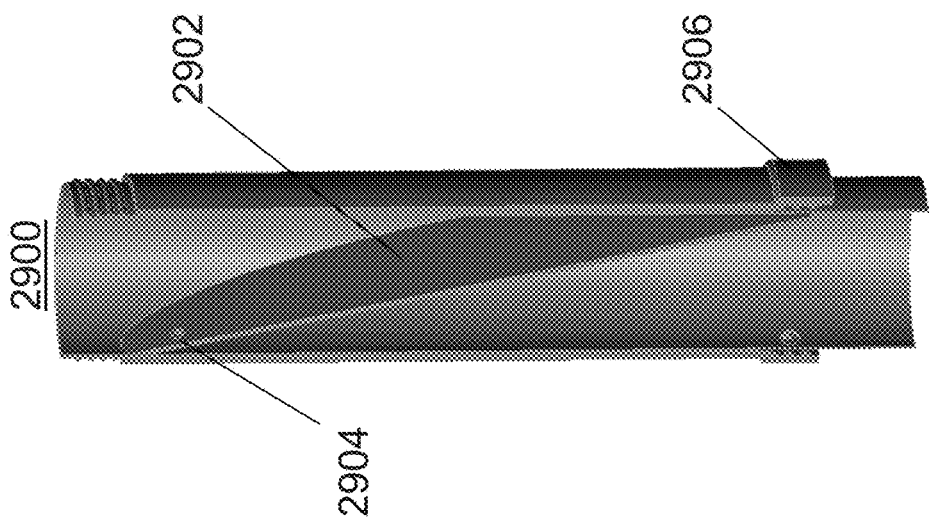

FIG. 29A depicts a cross sectional view of a partitioned cylinder 2900 for use in a fluid layering process. The cylinder 2900 includes an interior partition 2902 extending diagonally from the top of the cylinder 2900 to the bottom of the cylinder 2900. At the top of the partition 2902 is a vent 2904. A threaded ring 2906 surrounds a bottom portion of the cylinder 2900. FIG. 29B is an enlarged cross sectional view of the bottom portion of the cylinder 2900, partition 2902, and threaded ring 2906. Also shown in FIG. 29B is a gap 2908 between the cylinder wall and the bottom edge of the partition 2902, and a second vent 2910.

The cylinder 2900 can be inserted into a container used for fluid layering. In some implementations, the threaded ring 2906 can screw into threads located at the top of the container, to stabilize the cylinder 2900 and the container. Sample fluid can be introduce into the top of the cylinder 2900 can travel downwards along the top surface of the partition 2902 under the force of gravity. The narrow opening of the gap 2908 and the pressure from the weight of the fluid cause the fluid to be evenly dispersed on the walls of the cylinder 2900 below the gap 2906 and on the walls of the container, which can lead to a smoother layering process. As the fluid displaces air within the container, the air can escape through the vents 2904 and 2910 to maintain relatively constant pressure inside the container.

Figure 29C:
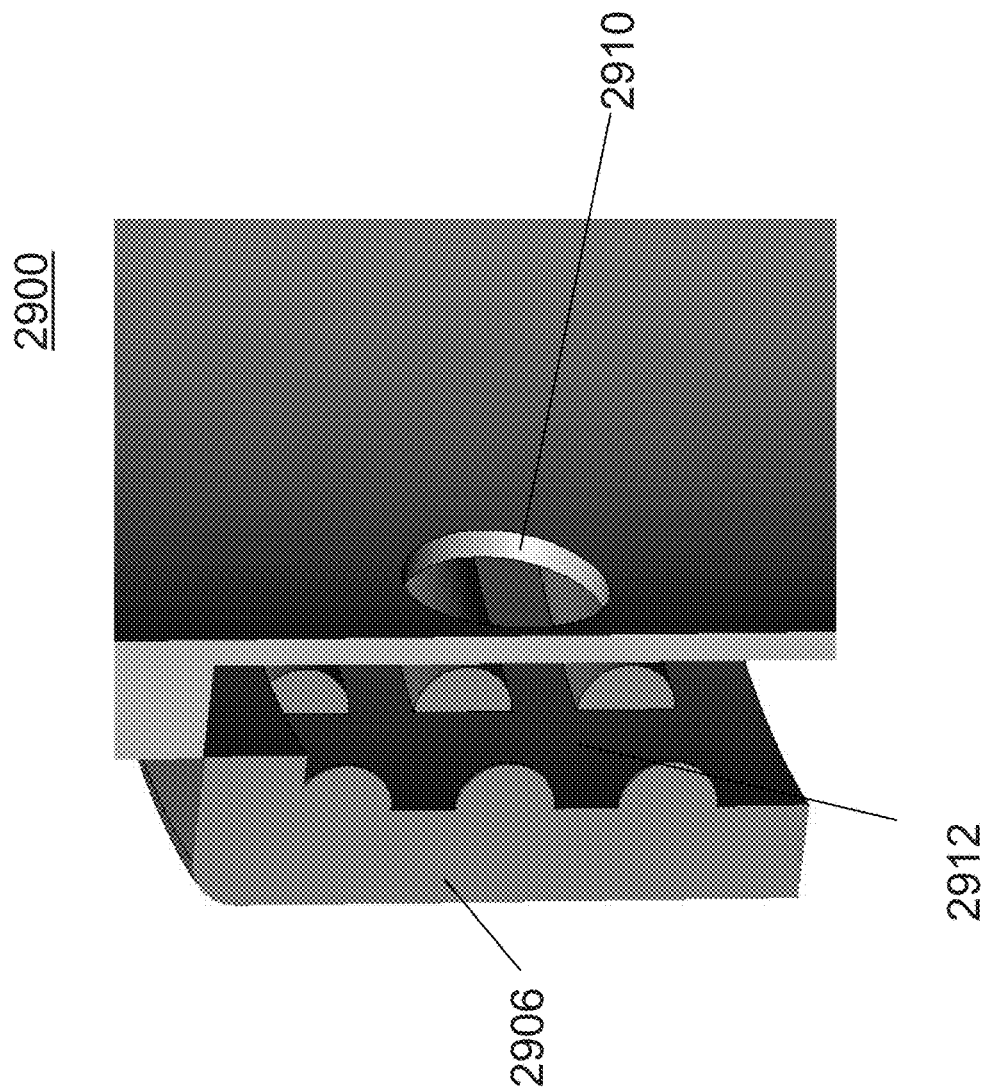

FIG. 29C is an enlarged view of the air vent 2910 and threaded ring 2906. As shown, there may be a gap 2912 in the threads of the threaded ring 2906, allowing air to pass through the vent 2910 and out of the cylinder 2900.

FIG. 30A depicts an hourglass insert 3000 for use in a fluid layering device. The hourglass insert 3000 can be put into a container used for layering fluids. Below the hourglass insert 3000 is a hemispherical member 3002, which attaches to the hourglass insert via rods 3004. Fluid can be introduced into the container and driver by gravity to the narrow opening in the center of the hourglass insert 3000. Due to the narrow opening and the weight of the fluid above, the fluid will be scattered evenly as it exits the narrow portion of the hourglass insert 3000. The fluid then contacts the hemispherical member 3002, and gravity drives the fluid toward the outside edge of the hemispherical member 3002. The fluid then travels through a narrow gap between the edge of the hemispherical member 3002 and the walls of the container. This prevents the fluid from traveling directly down the open center portion of the container, resulting in a slower and more controlled layering process.

FIG. 30B depicts an alternative embodiment of the hourglass insert 3000 and the hemispherical member 3002. In this embodiment, the fluid is introduced into the container and contacts the hemispherical member 3002. Gravity forces the fluid to the outside edge of the hemispherical member 3002, and the fluid evenly coats the walls of the upper portion of the hourglass insert 3000. The fluid then exits through the narrow portion of the hourglass insert 3000 and is scattered evenly onto the walls of the container below the hourglass insert 3000. It should be noted that the hemispherical member 3002 can be implemented using other shapes as well.

FIG. 31A depicts a reservoir 3100 and four scoops 3102 for use in a fluid layering process. The first scoop 3102 attaches to the reservoir 3100 by a hinge 3104, and each of the bottom three scoops 3102 attach to hinges 3104 on the scoops 3102 above them. As shown, each successive scoop 3102 is rotated 180 degrees from the scoop 3102 preceding it. The scoops 3102 can be lowered into a container for layering fluid. Fluid can exit the reservoir 3100 and be redirected at about a 45 degree angle by the first scoop 3102. As it leaves the first scoop 3102, the fluid is again redirected by the second scoop 3102. The fluid is redirected by each scoop 3102, which slows the movement of the fluid towards and results in a smoother fluid layering process. Although four scoops 3102 are shown in FIG. 31A, any number of scoops 3102 could be used.

FIG. 31B is an enlarged view of the scoops 3102. As shown, the scoops 3102 can have a curved cutout 3106 at the end, allowing the fluid to flow more smoothly into the next scoop 3102. FIG. 31C shows that scoops 3102 in a collapsed position. The scoops 3102 are lightweight and buoyant. As the fluid level rises, the scoops 3102 can rise and collapse into each other.

Note that in various embodiments, the fluid layering devices and techniques descried in reference to FIGS. 30A-31C may be used as an alternative to, or in combination with, the plunger based techniques described herein.

Figure 32:
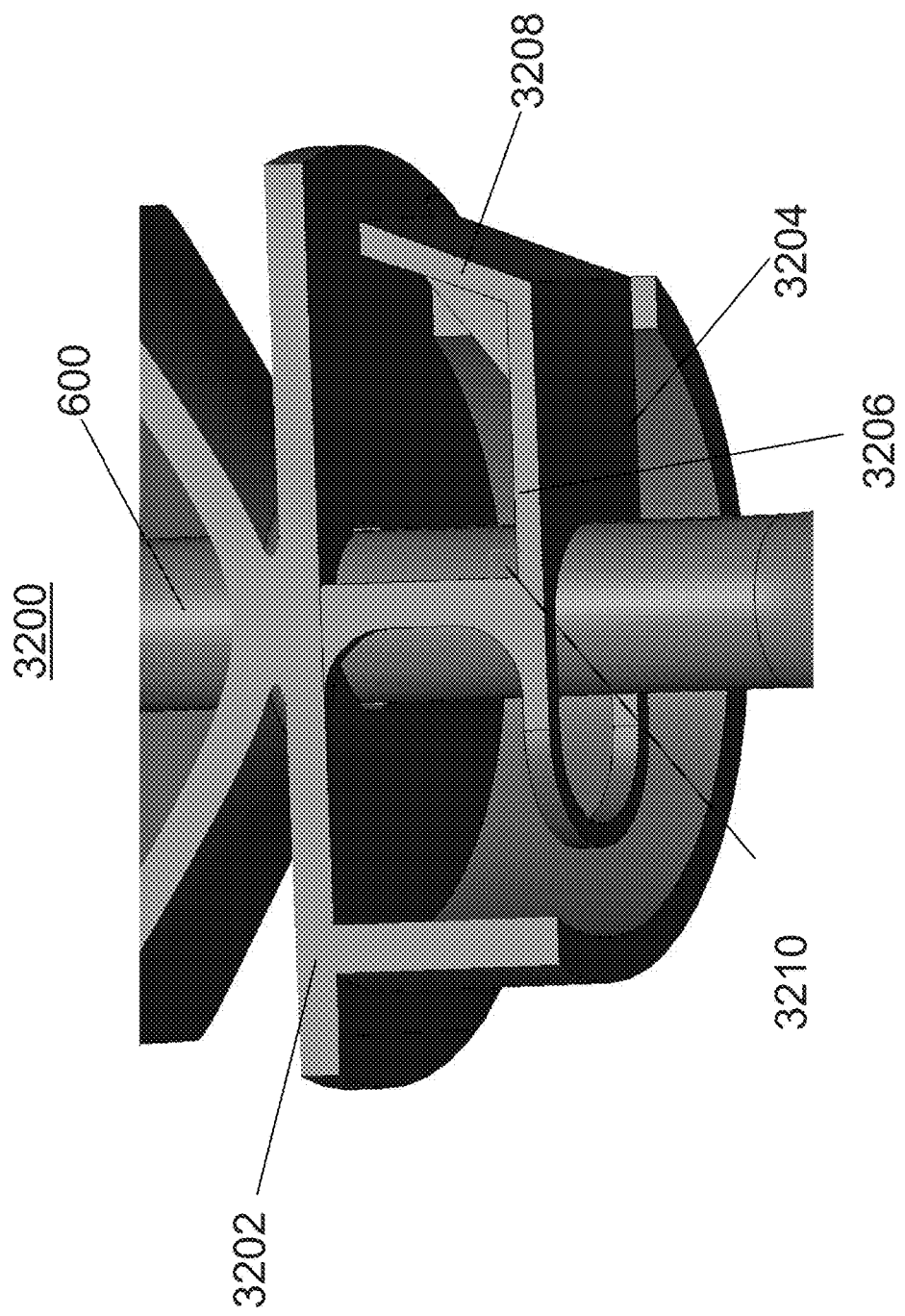
FIG. 32 illustrates an implementation of a mechanism for securing a plunger.

FIG. 32 depicts a cross sectional view of a mechanism 3200 for securing the plunger 600 in place. The mechanism includes a ceiling 3202 with a circular hole through which the plunger 600 can be inserted. The mechanism also includes a stabilizing member 3204 having a horizontal member 3206 coupled to an angled member 3208. At rest, the angle 3210 is slightly greater than 90 degrees, which puts pressure on the plunger 600 and prevents the plunger 600 from moving. As the mechanism 3200 and plunger 600 are lowered into a container to be used in the fluid layering process, the side of the container applies force to the angled member 3208. The force causes the stabilizing member 3204 to bend such that the angle 3210 is less than 90 degrees. Thus, the mechanism 3200 no longer puts pressure on the plunger 600, and the plunger 600 is released so that it may be lowered farther into the container. When mechanism 3200 will lock the plunger 600 into place again when the force applied to the angled member 3208 is removed.

Figure 33A:
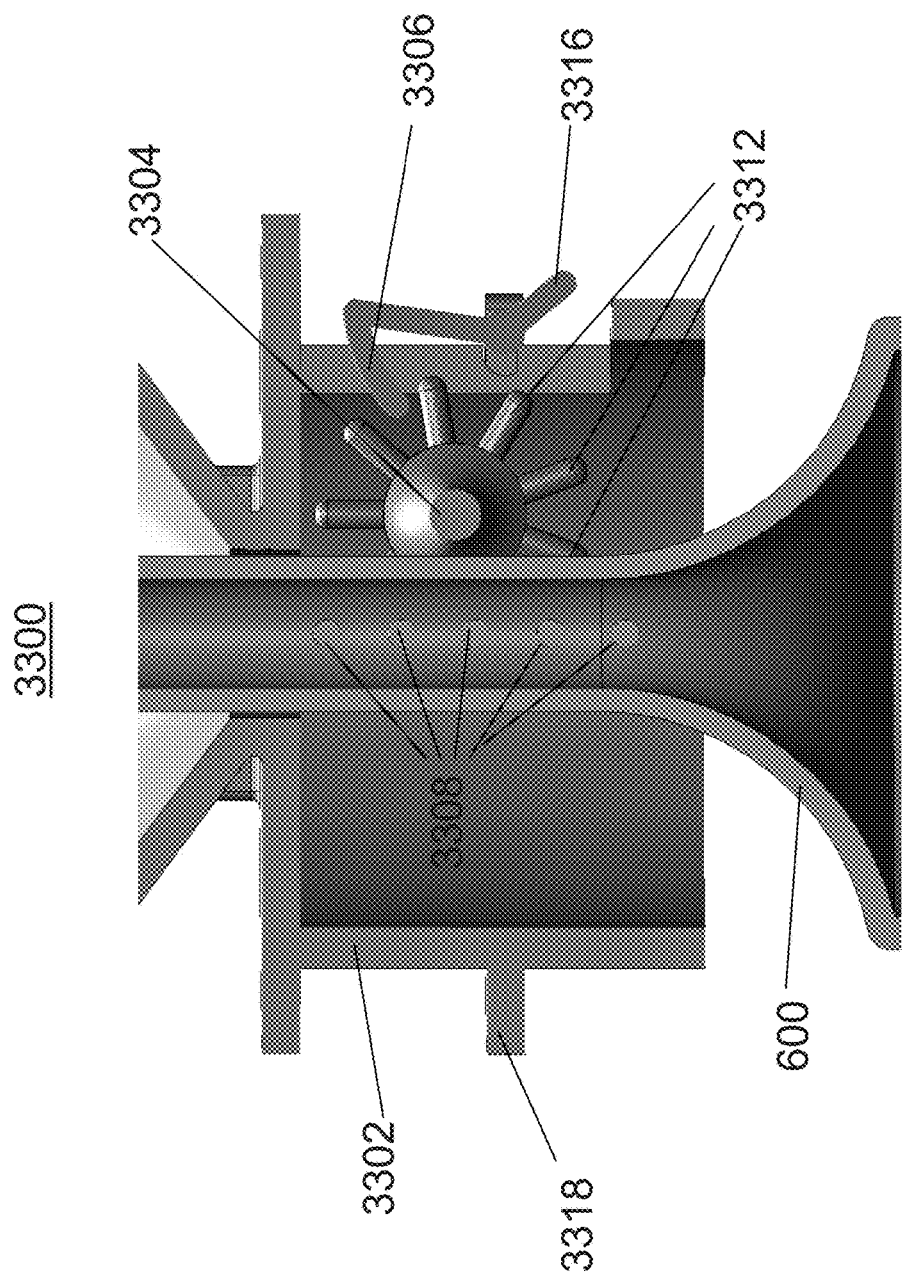

FIG. 33 depicts another mechanism 3300 for securing the plunger 600. The mechanism 3300 includes a housing 3302, a spindle 3304, a hook 3306, and vertebra 3308 installed on the plunger 600. FIG. 33B shows another view of the vertebra 3308, which extend outward from two sides of the shaft of the plunger 600. FIG. 33C depicts the spindle 3304. The spindle 3304 includes two cylindrical members 3310, each having teeth 3312 extending radially outward. The two cylindrical members 3310 are joined by an hourglass member 3314. When the spindle 3304 is installed, the curvature of the hourglass member aligns with the curvature of the shaft of the plunger 600, and the teeth 3312 of the spindle 3304 interlock with the vertebra 3308.

Referring again to FIG. 33A, the hook 3306 includes a tail 3316 and is mounted the housing 3302. The housing 3302 is surrounded by a platform 3318. The top portion of the hook 3306 is relatively heavy, which causes the hook to fall forward and lock the spindle 3304 into place and prevents the plunger 600 from moving. When the mechanism 3200 is put into a container, the walls of the container force the tail 3316 of the hook 3306 inwards towards the plunger 600. This releases the spindle 3304 from the hook 3306, and allows the plunger 600 to move downwards into the container. The platform 3318 encircles the housing 3302 at the same level as the pivot point of the hook 3306. The platform prevents the wall of a container from passing above the pivot point of the hook 3306, which could accidentally reengage the hook 3306. When the mechanism 3300 is removed from the container, the hook 3306 will reengage and the plunger 600 can be pulled upwards.

Figure 34A:
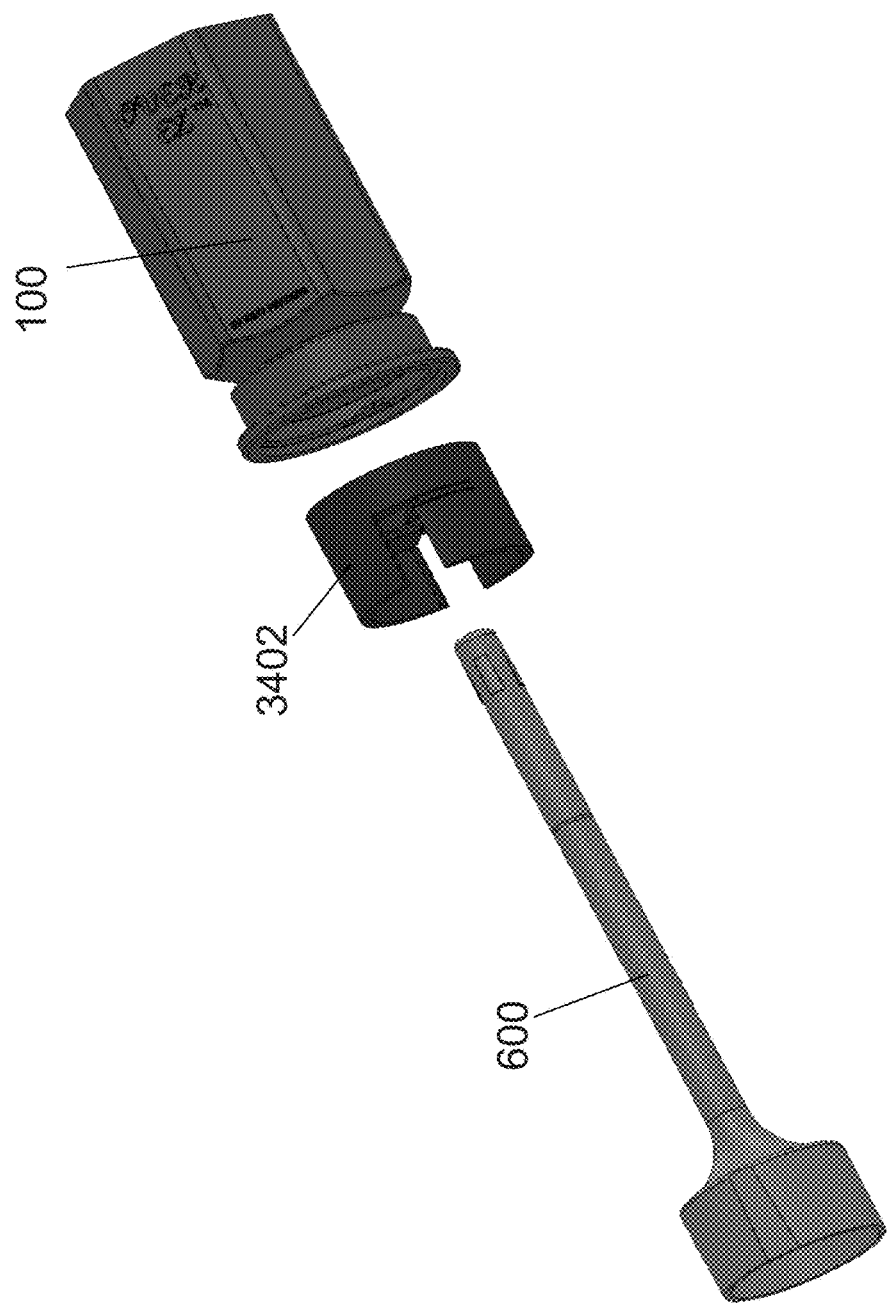
FIG. 34A-D illustrate a third implementation of a mechanism for securing a plunger.
Figure 34C:
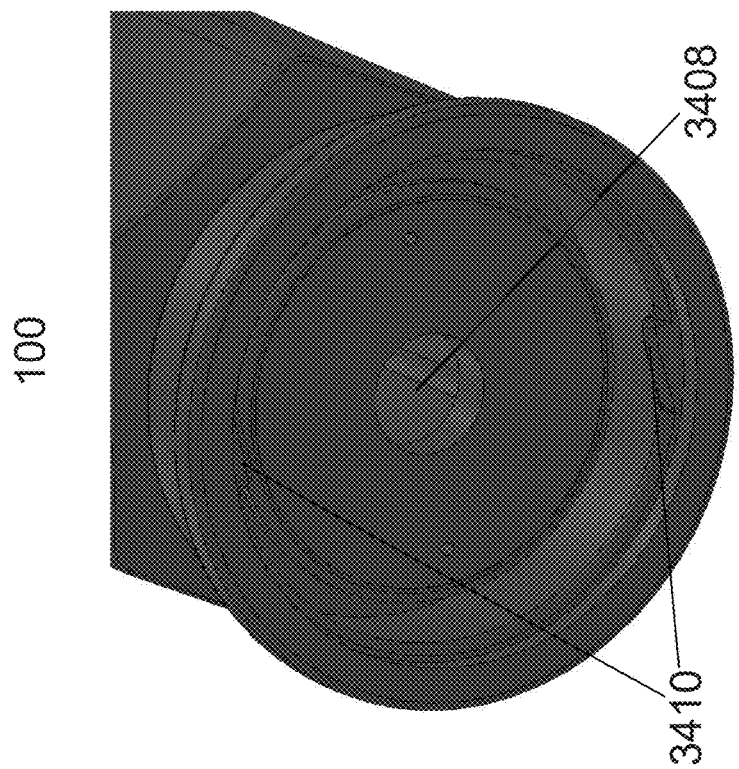
Figure 34B:
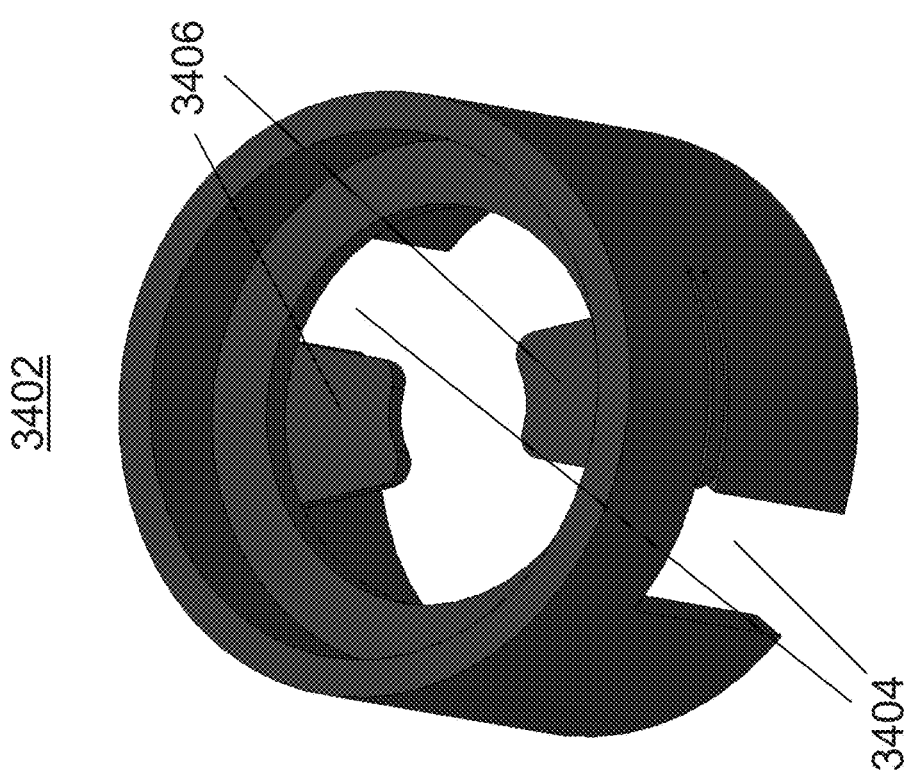

FIG. 34A shows an exploded view of a mechanism 3400 for securing a plunger 600. The mechanism 3400 includes features on the fluid layering device 100 described above, as well as a cylindrical member 3402. FIG. 34B is an expanded view of the cylindrical member 3402 shown in FIG. 34A. The cylindrical member 3402 includes two cutouts 3404 and fins 3406 extending inwards towards the center of the cylindrical member 3402. FIG. 34C depicts an enlarged view of the device 100. The device includes a central opening 3408 and two notches 3410 protruding inwards from the outside edge of the device 100, below the opening 3408.

Figure 34D:
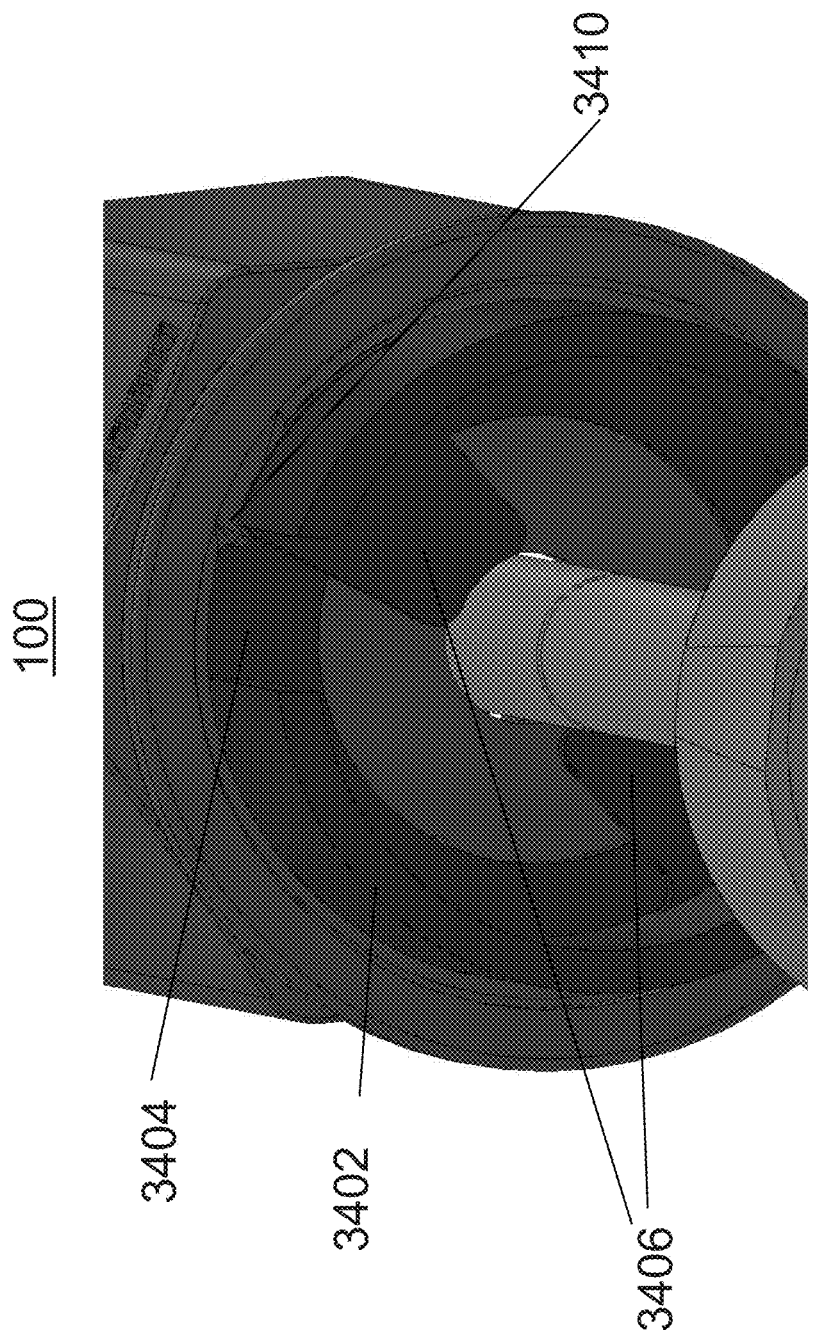

As shown in FIG. 34D, the cutouts 3404 can be aligned with the notches 3410, allowing the cylindrical member 3402 to be partially inserted into the device 100. The cylindrical member 3402 can then be rotated counterclockwise about its central axis, causing the notches 3410 of the device 100 to force the fins 3406 of the cylindrical member 3402 to move inwards towards the center of the cylindrical member 3402. The fins 3406 apply force to the plunger 600, securing the plunger 600 in place. Rotating the cylindrical member 3402 clockwise disengages the notches 3410 from the fins 3406, and releases the plunger 600.

Figure 35C:
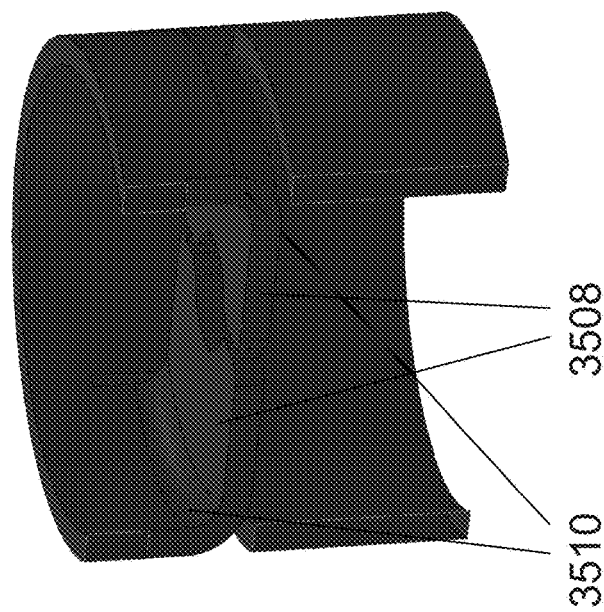
Figure 35B:
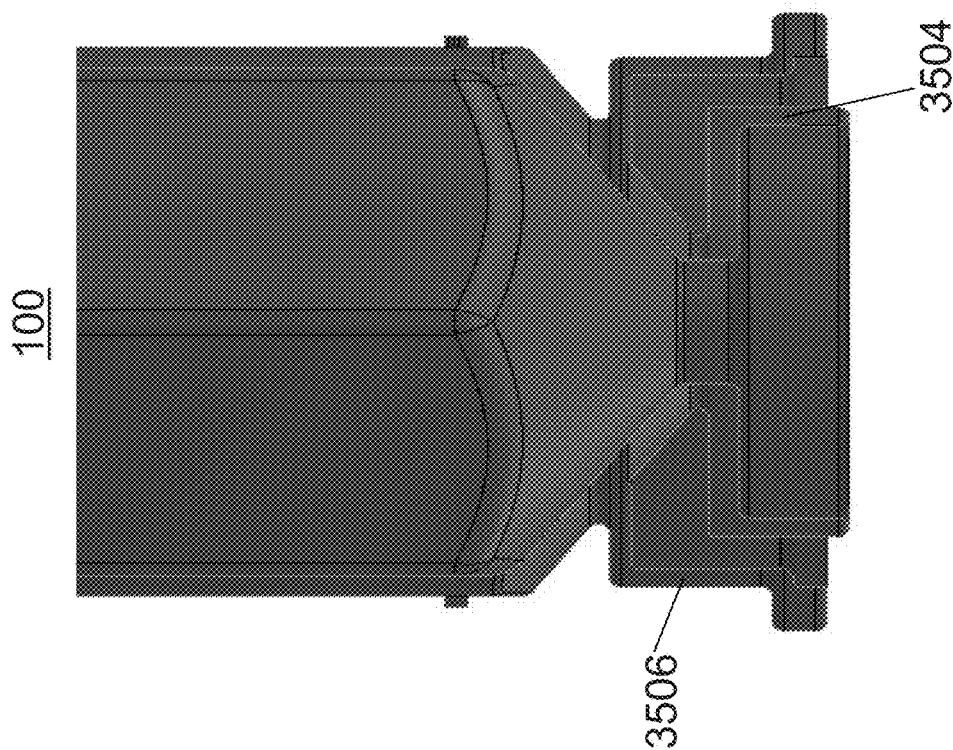

FIG. 35A depicts still another mechanism 3500 for securing the plunger 600 within the device 100. The mechanism includes features of the device 100, a cylindrical member 3502, and the plunger 600. FIG. 35B depicts a cross sectional view of the device 100, according to an illustrative implementation. The device 100 includes two concentric cylinders 3504 and 3506 having different radii. FIG. 35C shows a cross sectional view of the cylindrical member 3502, which includes two fins 3508 extending inwards towards the center of the cylindrical member 3502. The fins 3508 are coupled to the side walls of the cylindrical member 3502 via curved connectors 3510.

Figure 35D:
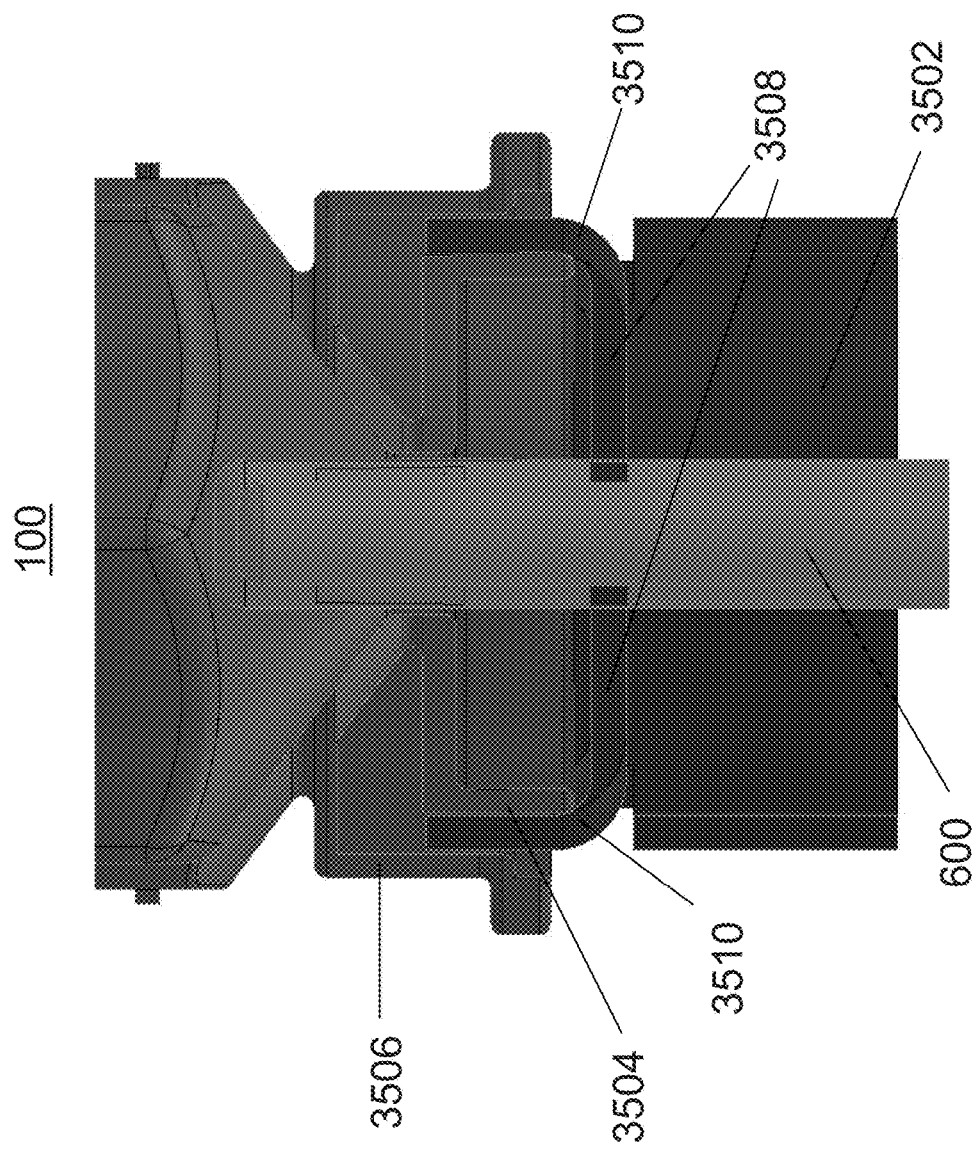

FIG. 35D depicts a cross sectional view of the locking mechanism 3500, including the device 100, the cylindrical member 3502, and the plunger 600. As shown, the cylindrical member 3502 is inserted into the device 100, such that the walls of the cylindrical device 100 are between the concentric cylinders 3504 and 3506 of the device 100. The plunger 600 is inserted through the center of the device 100 and the cylindrical member 3502. The fins 3508 are in contact with the plunger 600, holding it in place. In some implementations, the plunger 600 can have notches into which the fins 3508 can be inserted, to increase the stability of the plunger 600. When a downward force is applied to the device 100, the smaller of the concentric cylinders 3504 puts pressure on the curved connectors 3510 and causes the fins 3508 the move outwards, releasing the plunger 600. The plunger 600 can be secured by removing the downward force on the device 100, which will allow the fins 3508 to again put pressure on the plunger 600.

Figure 36A:
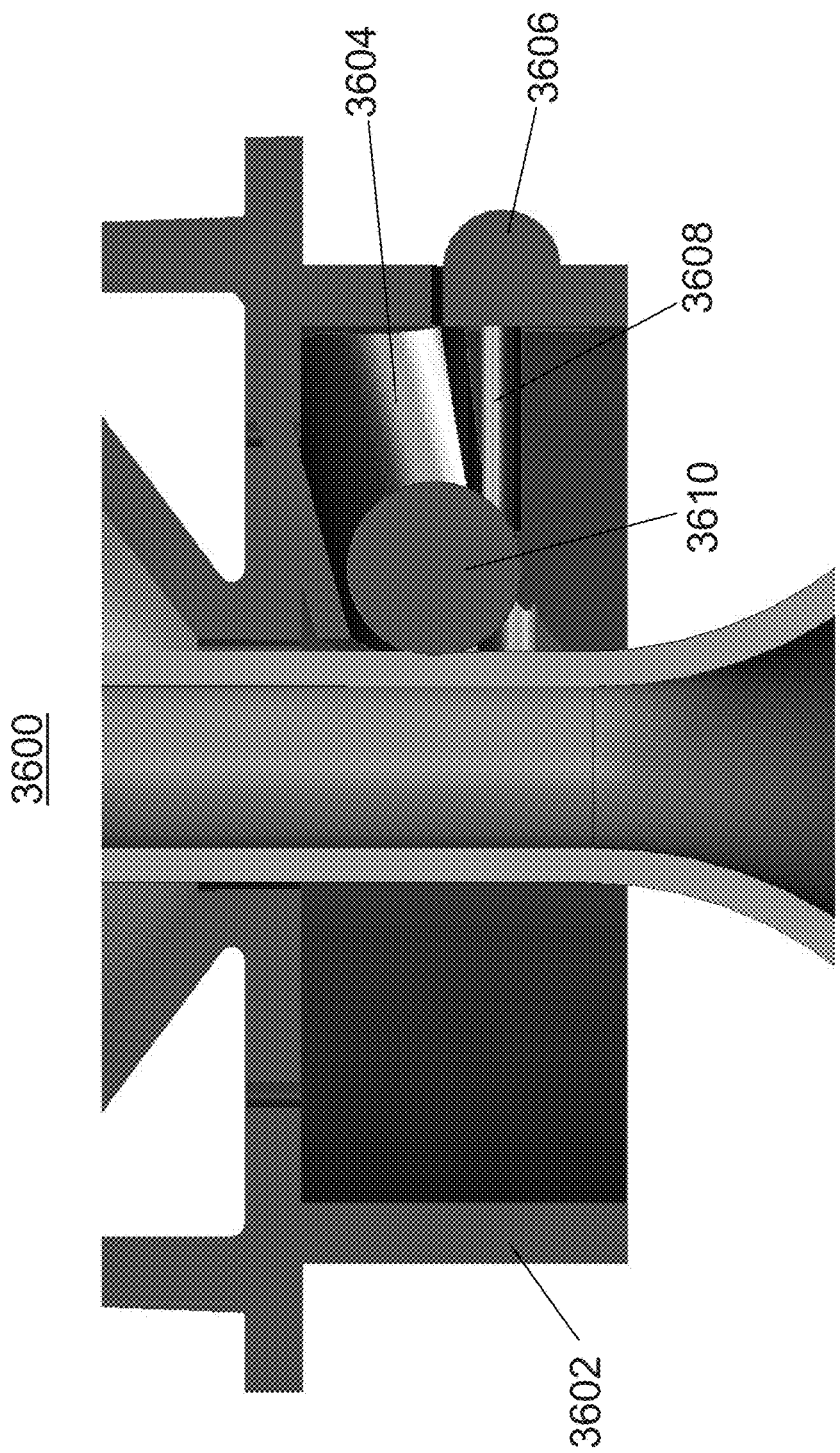
FIG. 36A-C illustrates a fifth implementation of a mechanism for securing a plunger.
Figure 36B:
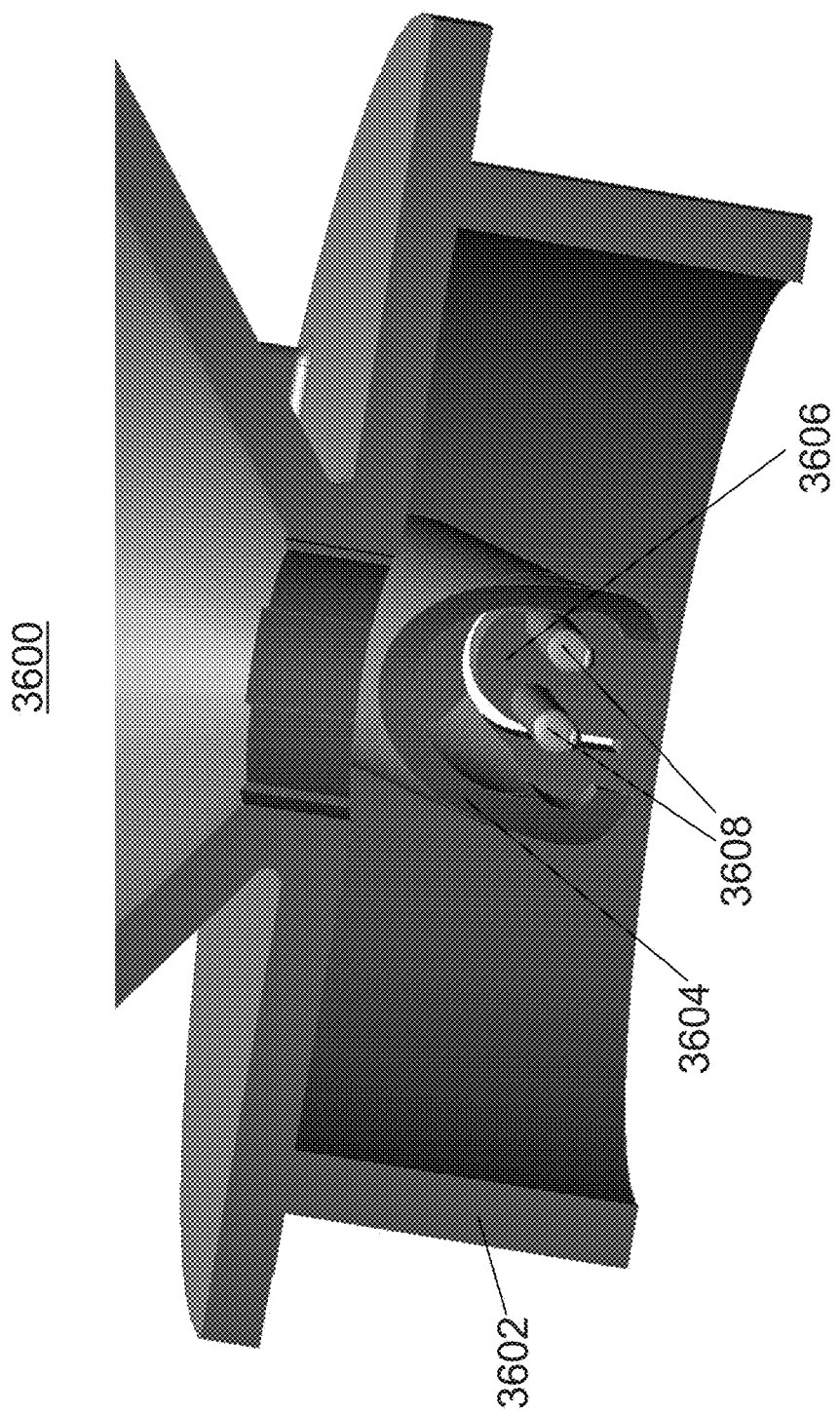

FIG. 36A depicts yet another mechanism 3600 for securing the plunger 600. The mechanism 3600 includes a housing 3602, an open cylinder 3604 and a tab 3606. The cylinder 3604 is positioned at a slight downward angle, extending inward from the edge of the housing 3602 towards its center. Extending inwards from the tab 3606 along the bottom of the cylinder 3602 are two prongs 3608. A ball 3610 sits on top of the prongs 3610 inside the cylinder 3604. In some implementations, the ball is made of a soft material, such as silicone or rubber. FIG. 36B depicts a second cross sectional view of the mechanism 3600. As shown, the end of the cylinder 3604 can have a curvature to align with the curvature of the plunger 600. The prongs 3608 can have beveled ends.

Figure 36C:
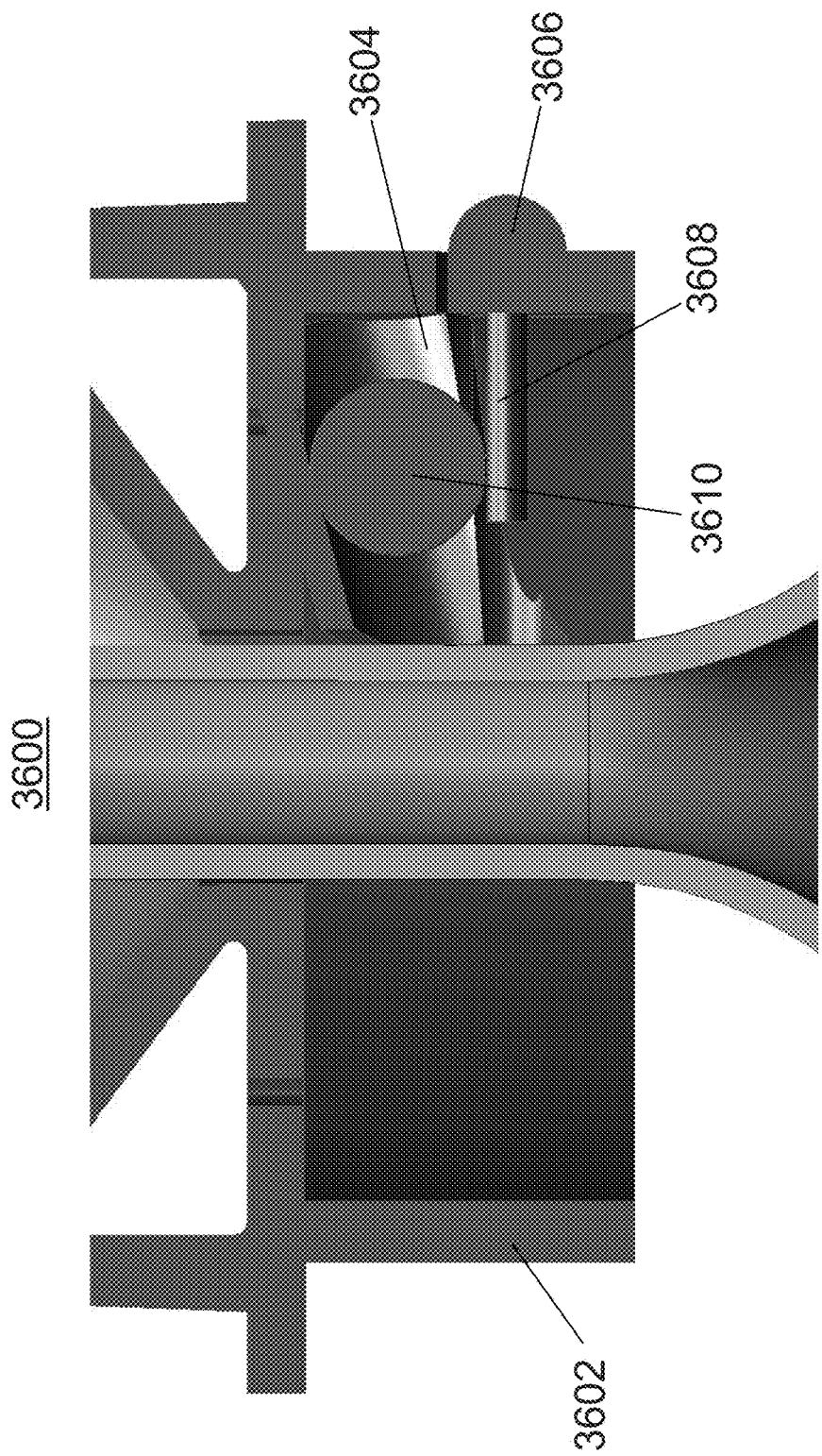

Referring again to FIG. 36A, the downward angle of the cylinder 3604 causes the ball 3610 to be positioned at the end of the cylinder 3604, in contact with the plunger 600, due to the force of gravity. The ball 3610 becomes wedged between the bottom of the cylinder 3604 and the plunger 600, preventing the plunger 600 from moving. When the tab 3606 is pressed inwards, as shown in FIG. 36C, the ball 3610 is lifted upwards in the cylinder 3604, away from the plunger 600. The plunger 600 is thus free to move. Releasing the tab 3606 causes the ball 3610 to move back towards the plunger 600. The ball will become wedged between the plunger 600 and the cylinder 3604, and the plunger 600 will be secured.

Although discussed primarily above in terms of layering a fluid such as blood on a fluid such as Ficoll-paque PLUS, the methods and apparatus discussed herein may be applied to any layering of two fluids of similar density in a vessel to prevent mixing. For example, the apparatus may be used to layer different flavors or colors of beverages, oils, alcohols, or other fluids. In embodiments where absolute sterility is not required, the apparatus may be made of durable and/or washable materials, such as glass or metal.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While the present invention has been described in connection with the preferred embodiments of the various figures, it is to be understood that other similar embodiments may be used or modifications or additions may be made to the described embodiment for performing the same function of the present invention without deviating therefrom.

Therefore, the present invention should not be limited to any single embodiment, but rather construed in breadth and scope in accordance with the recitation of the appended claims.

Other embodiments will be evident to those of skill in the art. It should be understood that the foregoing detailed description is provided for clarity only and is merely exemplary. The spirit and scope of the present invention are not limited to the above examples, but are encompassed by the following claims.

The invention claimed is:

1. A trap insert configured for insertion into a conical container, the trap insert comprising:
   a conical opening;
   a lip;
   a reservoir defined by a partial wall;
   an exit chamber;
   a cap, the cap comprising:
      a flat circular member; and
      hooks extending upwards from edges of the circular member.

2. The trap insert of claim 1 wherein the hooks are configured to interact with the lip to limit the downward motion of the cap.

3. The trap insert of claim 2 further comprising a fluid, a weight of the fluid depressing the cap and exiting through the exit chamber to fill the reservoir and part of the conical opening, a pressure from the fluid causing the cap to rise and seal off a portion of the conical container below the cap.

4. The trap insert of claim 3 wherein the fluid is blood.

5. The trap insert of claim 1, wherein an inner surface of the conical container comprises spiral notches to control a speed of a float a fluid.

6. A system comprising:
   an open-ended container; and
   a fluid layering device configured control a flow of fluid into the open-ended container, the fluid layering device comprising a trap member inserted into the open-ended container, the trap member comprising:
      a conical opening;
      a lip;
      a reservoir defined by a partial wall;
      an exit chamber;
      a cap, the cap comprising:
         a flat circular member; and
         hooks extending upwards from edges of the circular member.

7. The system of claim 6, wherein the cap comprises:
   a flat circular number; and
   hooks extending upwards from edges of the circular member.

8. The system of claim 7 where in the hooks are configured to interact with the lip to limit the downward motion of the cap.

9. The system of claim 8 further comprising a fluid, a weight of the fluid depressing the cap and exiting through the exit chamber to fill the reservoir and part of the conical opening, a pressure from the fluid causing the cap to rise and seal off a portion of the container below the cap.

* * * * *